(12) United States Patent
Shih et al.

(10) Patent No.: US 11,243,200 B2
(45) Date of Patent: *Feb. 8, 2022

(54) PIEZOELECTRIC PLATE SENSOR AND USES THEREOF

(71) Applicant: Drexel University, Philadelphia, PA (US)

(72) Inventors: Wan Y. Shih, Bryn Mawr, PA (US); Wei Wu, Philadelphia, PA (US); Wei-Heng Shih, Bryn Mawr, PA (US); Mehmet Cagri Soylu, Melikgazi (TR); Haitao Guo, Carmel, IN (US); Suresh G. Joshi, Secane, PA (US); Ceyhun Ekrim Kirimli, Thunder Bay (CA); Ying-Hsiu Su, Audubon, PA (US)

(73) Assignee: Drexel University, Philadelphia, PA (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/216,848

(22) Filed: Dec. 11, 2018

(65) Prior Publication Data
US 2019/0120833 A1    Apr. 25, 2019

Related U.S. Application Data

(63) Continuation of application No. 15/101,788, filed as application No. PCT/US2014/071555 on Dec. 19, 2014, now Pat. No. 10,197,565.
(Continued)

(51) Int. Cl.
*G01N 33/543*    (2006.01)
*G01N 29/02*    (2006.01)
(Continued)

(52) U.S. Cl.
CPC ..... *G01N 33/54373* (2013.01); *C12Q 1/6825* (2013.01); *G01N 29/022* (2013.01);
(Continued)

(58) Field of Classification Search
CPC ....... G01N 33/54373; G01N 33/54393; G01N 29/022; G01N 27/036; G01N 2291/0255;
(Continued)

(56) References Cited

U.S. PATENT DOCUMENTS 6,247,354 B1    6/2001    Vig et al.
7,084,554 B2    8/2006    Xu et al.
(Continued)

FOREIGN PATENT DOCUMENTS

WO    WO2008006060 A1    1/2008
WO    WO2008067386 A2    6/2008
(Continued)

OTHER PUBLICATIONS

Soylu et al., Insulation by Solution 3-Mercaptopropyltrimethoxysilane (MPS) Coating: Effect of pH, Water and MPS Content, American Chemical Society, vol. 52, pp. 2590-2597. (Year: 2013).*
(Continued)

*Primary Examiner* — Melanie Brown
(74) *Attorney, Agent, or Firm* — Mendelsohn Dunleavy, P.C.

(57) ABSTRACT

A piezoelectric plate sensor comprising a piezoelectric layer; two electrodes; and an insulation layer. The insulation layer is produced by soaking the piezoelectric layer and two electrodes in a mercaptopropyltrimethoxysilane solution with an amount of water from 0.1 v/v. % to about 1 v/v % and at pH from about 8 to about 150 for a period from about 8 to about 15 hours, and the mercaptopropyltrimethoxysilane solution has a concentration of mercaptopropyltrimethoxysilane from about 0.01 v/v % to about 0.5 v/v %.

(Continued)

A method of detecting a biomolecule in a sample using the piezoelectric plate sensor in particular, that of detecting a genetic marker with PCR sensitivity and specificity without the need of DNA isolation or amplification is also provided. The piezoelectric plate sensor may be used to diagnose various diseases including breast cancer, myocardial infarction, diarrhea, *Clostridium difficile* infection, and hepatitis B infection.

19 Claims, 54 Drawing Sheets
(51 of 54 Drawing Sheet(s) Filed in Color)

Specification includes a Sequence Listing.

Related U.S. Application Data

(60) Provisional application No. 61/920,194, filed on Dec. 23, 2013.

(51) Int. Cl.
*G01N 29/036* (2006.01)
*C12Q 1/6825* (2018.01)

(52) U.S. Cl.
CPC ..... *G01N 29/036* (2013.01); *G01N 33/54393* (2013.01); *G01N 2291/0255* (2013.01); *G01N 2291/0256* (2013.01); *G01N 2291/0427* (2013.01)

(58) Field of Classification Search
CPC ... G01N 2291/0256; G01N 2291/0427; C12Q 1/6825
See application file for complete search history.

(56) References Cited

U.S. PATENT DOCUMENTS

| | | | |
|---|---|---|---|
| 7,335,345 | B2 | 2/2008 | Shih et al. |
| 7,458,265 | B2 | 12/2008 | Shih et al. |
| 8,481,335 | B2 | 7/2013 | Shih et al. |
| 8,491,818 | B2 | 7/2013 | Shih et al. |
| 8,741,663 | B2 | 6/2014 | Shih et al. |
| 8,803,264 | B1* | 8/2014 | Katiyar ............ H01L 41/16 257/421 |
| 10,197,565 | B2* | 2/2019 | Shih ............ G01N 33/54373 |
| 2002/0078749 | A1 | 6/2002 | Tajika et al. |
| 2003/0118735 | A1 | 10/2003 | Wakabayashi et al. |
| 2004/0021403 | A1 | 2/2004 | Ayazi et al. |
| 2005/0112621 | A1 | 5/2005 | Kim et al. |
| 2005/0277852 | A1 | 12/2005 | Shih et al. |
| 2006/0088839 | A1* | 4/2006 | Matsui ............ C12Q 1/6825 435/6.11 |
| 2006/0153736 | A1 | 7/2006 | Kalra et al. |
| 2009/0203154 | A1 | 8/2009 | Carter et al. |
| 2009/0289529 | A1 | 11/2009 | Ito et al. |
| 2010/0068490 | A1 | 3/2010 | Shih et al. |
| 2010/0210032 | A1 | 8/2010 | Shih et al. |
| 2010/0294976 | A1* | 11/2010 | Ajayan ............ H01L 41/183 252/62.9 PZ |
| 2011/0086368 | A1 | 4/2011 | Shih et al. |
| 2011/0086435 | A1 | 4/2011 | Shih et al. |
| 2011/0256538 | A1 | 10/2011 | Su et al. |

FOREIGN PATENT DOCUMENTS

| | | |
|---|---|---|
| WO | WO2009046251 A2 | 4/2009 |
| WO | WO2009126378 A3 | 10/2009 |

OTHER PUBLICATIONS

Brito, R. et al., "Adsorption of 3-mercaptopropyltrimethoxysilane and 3-aminopropyltrimethoxysilane at platinum electrodes", J. Electroanalytical Chem., 520: 47-52 (2002).

Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).

International Search Report and Written Opinion; dated Apr. 22, 2015 for PCT Application No. PCT/US2014/071555.

Passamano, Myriam, and Monica Pighini. "QCM DNA-sensor for GMOs detection." Sensors and Actuators B: Chemical 118.1 (2006): 177-181.

Feng, Kejun, et al. "QCM detection of DNA targets with single-base mutation based on DNA ligase reaction and biocatalyzed deposition amplification." Biosensors and Bioelectronics 22.8 (2007): 1651-1657.

Park, So-Jung, T. Andrew Taton, and Chad A. Mirkin. "Array-based electrical detection of DNA with nanoparticle probes." Science 295.5559 (2002): 1503-1506.

Zhang, Guo-Jun, et al. "Morpholino-functionalized silicon nanowire biosensor for sequence-specific label-free detection of DNA." Biosensors and Bioelectronics 25.11 (2010): 2447-2453.

Gao, Zhiqiang, et al. "Silicon nanowire arrays for label-free detection of DNA." Analytical Chemistry 79.9 (2007): 3291-3297.

Hahm, Jong-in, and Charles M. Lieber. "Direct ultrasensitive electrical detection of DNA and DNA sequence variations using nanowire nanosensors." Nano letters 4.1 (2004): 51-54.

Su, Ming, Shuyou Li, and Vinayak P. Dravid. "Microcantilever resonance-based DNA detection with nanoparticle probes." Applied Physics Letters 82.20 (2003): 3562-3564.

Chang, Haixin, et al. "Electrochemical DNA biosensor based on conducting polyaniline nanotube array." Analytical chemistry 79.13 (2007): 5111-5115.

Wu, Wei, Wan Y. Shih, and Wei-Heng Shih. "Enhancing detection sensitivity of piezoelectric plate sensor by increasing transverse electromechanical coupling constant." Journal of Applied Physics 114.6 (2013): 064505.

Soylu, Mehmet Çağrı. Piezoelectric Plate Sensor for in situ Genetic Detection of Hepatitis B Virus in Serum without DNA Isolation and Amplification. Diss. Drexel University, 2013.

Su, Ying-Hsiu, et al. "Detection of Mutated K-ras DNA in Urine, Plasma, and Serum of Patients with Colorectal Carcinoma or Adenomatous Polyps." Annals of the New York Academy of Sciences 1137.1 (2008): 197-206.

\* cited by examiner

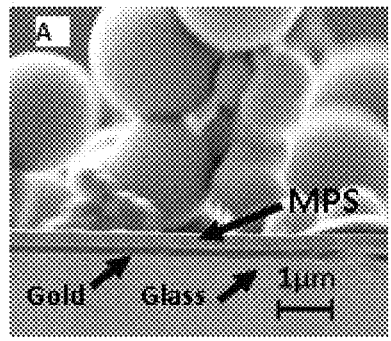 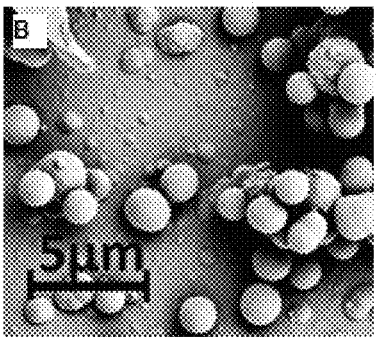 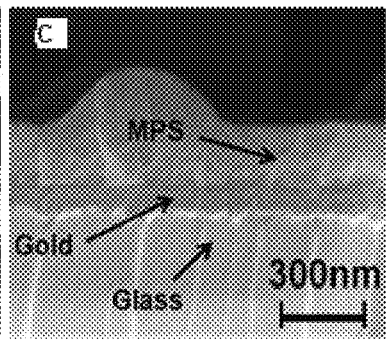
Figure 9A  Figure 9B  Figure 9C
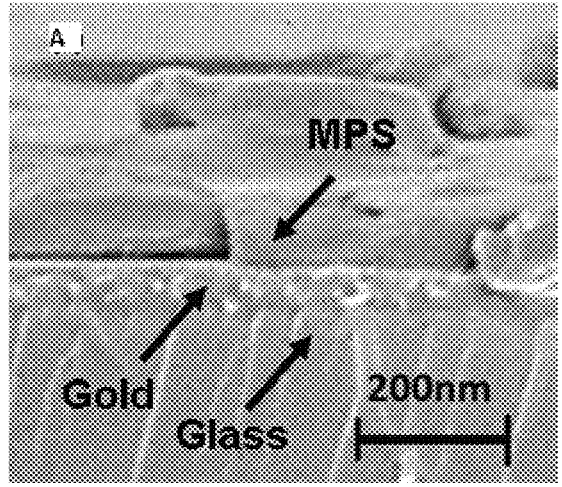 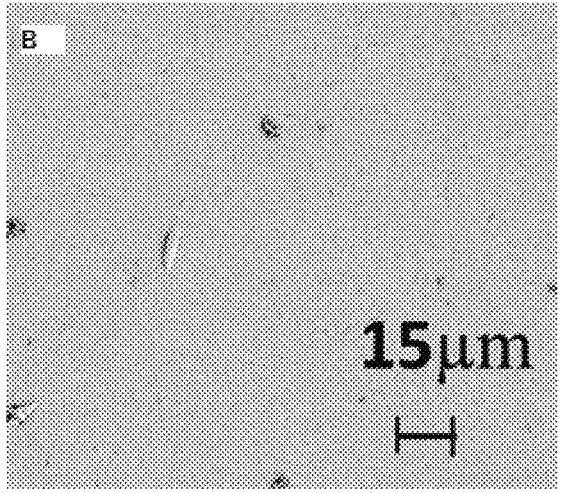
Figure 10A  Figure 10B

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: Synthetic sequence

<400> SEQUENCE: 1
ggttaatgat ctttgt                                              16

<210> SEQ ID NO 2
<211> LENGTH: 16
<212> TYPE: DNA
<213> ORGANISM: Artificial Sequence
<220> FEATURE:
<223> OTHER INFORMATION: synthetic sequence

<400> SEQUENCE: 2
ggttaaaggt ctttgt                                              16

<210> SEQ ID NO 3
<211> LENGTH: 16
<212> TYPE: DNA
<213> ORGANISM: Artificial Sequence

```
<220> FEATURE:
<223> OTHER INFORMATION: Synthetic sequence

<400> SEQUENCE: 3
acaaagatca ttaacc                                                          16

<210> SEQ ID NO 4
<211> LENGTH: 30
<212> TYPE: DNA
<213> ORGANISM: Artificial Sequence
<220> FEATURE:
<223> OTHER INFORMATION: synthetic sequence

<400> SEQUENCE: 4
acagaccaat ttatgcctac agcctcctag                                           30

<210> SEQ ID NO 5
<211> LENGTH: 30
<212> TYPE: DNA
<213> ORGANISM: Artificial Sequence
<220> FEATURE:
<223> OTHER INFORMATION: synthetic sequence

<400> SEQUENCE: 5
aatctcctcc cccaactcct cccagtcttt                                           30

<210> SEQ ID NO 6
<211> LENGTH: 26
<212> TYPE: DNA
<213> ORGANISM: Artificial Sequence
<220> FEATURE:
<223> OTHER INFORMATION: synthetic sequence

<400> SEQUENCE: 6
ccaaaatgga gtgttacaaa caggtg                                               26
```

PIEZOELECTRIC PLATE SENSOR AND USES THEREOF

CROSS-REFERENCE TO RELATED APPLICATIONS

This application filed Dec. 11, 2018 is a continuation application of U.S. patent application Ser. No. 15/101,788 (now U.S. Pat. No. 10,197,565) filed Jun. 3, 2016, which is a national stage application filed under 35 U.S.C. § 371 of International Patent application No. PCT/US1014/071555 filed Dec. 19, 2014, which claims the benefit of U.S. Provisional application No. 61/920,194 filed Dec. 23, 2013.

STATEMENT REGARDING FEDERALLY SPONSORED RESEARCH AND DEVELOPMENT

This application contains several inventions. The breast cancer detection aspect of this invention was made with government support under Contract No. W81XWH-09-1-0701 awarded by the Department of Defense, United States Army's Congressionally Directed Medical Research Programs, Breast Cancer Research Program (BCRP). The government has certain rights in the breast cancer detection invention.

INCORPORATION OF MATERIAL ASCII TEXT SEQUENCE LISTING BY REFERENCE

The sequence listing submitted herewith as a text file named "DREX-1140USCON Sequence Listing.ST25" created Oct. 2, 2021, which is 2 kilobytes in size, is hereby incorporated by reference in its entirety.

BACKGROUND OF THE INVENTION

1. Field of the Invention

The present invention is directed to the field of piezoelectric sensors and their use for detecting organic compounds. In particular, the present invention is directed to piezoelectric plate sensors capable of detecting organic compounds in a solution at very low concentrations.

2. Description of the Related Technology

There are many technologies that are capable of detecting biomolecules in a sample, such as quartz crystal microbalance-based technology, silicon microcantilever-based technology, electrochemical enzymatic immunoassays, fluorescence-based technology, laser-based or fiber-optics-based technology, amplification-based technology such as the polymerase chain reaction, and technology that tags metal particles to determine the presence of biomolecules. These technologies, however, fail to provide one or more of rapid, efficient or highly sensitive detection of biomolecules. In addition, many of them are also incapable of simultaneously detecting multiple biomolecules or being used in high throughput applications.

For example, quartz crystal microbalance-based technology, which utilizes thickness-mode resonance sensing, is one of the most commonly used biosensing technologies. Detection sensitivity of this technology is determined by its resonance frequency and the thickness of a quartz membrane. A resonance frequency of about 5 MHz, corresponding to a quartz membrane thickness of 330 µm, enables a minimum detectable mass density of about $10^{-9}$ g/cm$^2$. Sensitivity is therefore generally limited to a range of about $10^{-8}$ g/Hz, which is not sufficiently sensitive for many biomedical applications.

To increase detection sensitivity, some sensors utilize silicon-based microcantilevers, which are said to offer a sensitivity of approximately $10^{-12}$ g/Hz, about four orders of magnitude higher than the quartz crystal microbalance-based technology. Silicon microcantilevers are also commercially available and may be easily integrated with existing silicon fabrication industrial processes. Silicon microcantilevers, however, generally rely on complex external optical devices for deflection detection, and an external driving mechanism for actuation and laser alignment, which make the silicon microcantilevers complex and expensive to use. Moreover, silicon microcantilevers are inferior for in-solution detection, in comparison with piezoelectric sensors.

Piezoelectric cantilevers, in comparison, are much simpler and easier to operate than the silicon-based microcantilever sensors. Piezoelectric cantilevers are typically constructed from lead zirconate titanate (PZT) and use electrical means for detection of biomolecules. Piezoelectric cantilevers may be millimeter-size cantilevers made by bonding a commercial PZT film to a non-piezoelectric substrate such as stainless steel, titanium or glass. Piezoelectric cantilevers have a number of advantageous properties, such as the capability of electrical self-excitation and self-sensing for in-situ electrical detection. Furthermore, piezoelectric cantilevers, when coated with an insulation layer, are capable of preventing conduction in liquid media, rendering the piezoelectric cantilevers suitable for detection of biomolecules in liquids.

US 2011/0086368 discloses a piezoelectric microcantilever sensor for assessing a patient's immunological response by measuring a resonance frequency shift of the sensor caused by binding of an immunological response factor to a corresponding receptor on the surface of the sensor. The microcantilever sensor may have a piezoelectric layer at its center, two electrodes, an encapsulating insulation layer and a receptor layer on the insulation layer. The microcantilever sensor may be treated with a mercaptopropyltrimethoxysilane (MPS) solution in ethanol at a pH of 4.5 to form the encapsulating insulation layer. The pH of the MPS solution may be adjusted to 4.5 using glacial acetic acid. In one embodiment, an epidermal growth factor receptor is attached to the MPS insulation layer through a bi-functional linker such as sulfo-SMCC (sulfosuccinimidyl-4-(N-maleimidomethyl)cyclohexane-1-carboxylate). The microcantilever sensor is then exposed to a fluid for detection of epidermal growth factor in the fluid. An antibody may be bound to the microcantilever sensor for detecting an antigen.

WO 2009/126378 discloses a piezoelectric microcantilever sensor having enhanced detection sensitivity. The piezoelectric sensor includes a piezoelectric layer positioned between two conductive elements. For applications involving detection of a target in liquids, the sensor may be coated with an electrical insulating layer. The insulating layer may be either a coating of parylene(poly-para-xylylene) or self-assembled monolayers of methyltrimethoxysilane. U.S. Pat. No. 7,084,554 discloses a microcantilever, which comprise a piezoelectric thin PZT film of about 1-10 µm in thickness for the purpose of increasing the working frequency range of micro-electro-mechanical dimensioned systems. The patent further teaches that the piezoelectric thin film may be fabricated by thin film fabrication methods such as a sol-gel method, sputtering, hydrothermal methods, chemical vapor deposition or another thin film fabrication method, followed by low temperature annealing and dry etching, plasma etching or patterning by wet chemical etching.

Recent advances in thin-film piezoelectric PZT microcantilevers incorporate an electrical insulation layer that prevents liquid damping. US 2005/0112621 discloses a sensor system comprising a cantilever with a piezoelectric film and having one end fixed on a substrate, a piezoelectric capacitor for self-sensing and actuating on at least one side of an upper surface and a lower surface of the cantilever, a lower electrode formed at a lower surface of the piezoelectric film and an upper electrode formed at an upper surface of the piezoelectric film, an electric pad for applying electricity to the lower electrode and the upper electrode, and a molecular recognition layer formed at least one surface of the cantilever. The cantilever is taught to have an insulation layer surrounding the cantilever in order to prevent conduction in liquid media.

Piezoelectric plate sensors have been used to detect acceleration for the purpose of automotive posture control and seismic detection. US 2002/0078749 discloses an acceleration sensor comprising a first piezoelectric plate, a second piezoelectric plate bonded to the first piezoelectric plate by direct bonding, a first external electrode provided on the main surface of the first piezoelectric plate and a second external electrode provided on the main surface of the second piezoelectric plate. The first piezoelectric plate and second piezoelectric plates are bonded together with their polarization axes reversed relative to each other. The piezoelectric plate sensors however are not suitable for detecting biomolecules from a liquid sample.

Current piezoelectric-based sensors may lack the desired detection sensitivity necessary for many biomedical applications, particularly in-situ biosensing applications. These sensors typically have piezoelectric properties, characterized by a low piezoelectric coefficient $d_{31}$ of less than 20 pm/v. The detection sensitivity of piezoelectric cantilever sensors, which may be viewed as simple harmonic oscillators, is correlated to the resonance frequency shift capability of the sensor. The resonance frequency shift capability in turn is dependent upon the sensor's ability to respond to changes in the effective spring constant and effective mass of the sensor. Available piezoelectric-based sensors, such as piezoelectric microcantilevers constructed from bulk PZT of relatively large thickness, are only useful for detecting relatively large changes in the effective spring constant of the sensor.

Improving sensitivity, accuracy and efficiency of piezoelectric sensors for detecting biomolecules is important to the development of sensitive and reliable assays in the healthcare field for early detection and prevention of diseases. For example, early diagnosis of breast cancer, especially when the tumor is still small is important to the prognosis of the patient. However, diagnosis of early breast cancer by mammography is frequently inadequate and often produces false positives leading to unnecessary biopsies and stress to misdiagnosed patients. Diagnosing breast cancer using breast cancer biomarkers, such as HER2 in serum has gained significant attention. Therefore early detection methods for various cancers and other diseases that allow accurate, effective and non-invasive identification and quantification of disease biomarkers and pathogens are needed.

To address these issues, in one embodiment, the present invention provides a piezoelectric plate sensor (PEPS) capable of in-solution detection of biomolecules with a zeptomolar or higher sensitivity.

In addition, there remains a need for an array of sensors with high sensitivity and that is capable of simultaneous detection of multiple biomolecules in a sample.

SUMMARY OF THE INVENTION

In one aspect, the present invention relates to a PEPS comprising a piezoelectric layer; two electrodes positioned one on each side of the piezoelectric layer; and an insulation layer encompassing the piezoelectric layer and the electrodes.

In another aspect, the invention relates to a method of providing an insulation layer to a PEPS by treating the piezoelectric layer and two electrodes with a mercaptopropyltrimethoxysilane (MPS) solution in ethanol with an amount of water from 0.1 v/v. % to about 1 v/v % and at a pH from about 8 to about 10 for a period from about 8 to about 150 hours.

In another aspect, the PEPS of the present invention further comprises a non-piezoelectric layer bonded to the piezoelectric layer.

In yet another aspect, the PEPS of the present invention further comprises at least one recognition molecule bound to the surface thereof.

In yet another aspect, the PEPS of the present invention further comprises a bovine serum albumin coating on its surface.

In yet another aspect, the present invention provides a method of detecting a biomolecule in a sample of interest using the PEPS disclosed herein, the method including the steps of contacting the PEPS having a recognition molecule bound thereto with a sample; and measuring a resonance frequency shift of the PEPS due to binding of a biomolecule to the recognition molecule.

In yet another aspect, the method of the present invention further comprises the step of calibrating the resonance frequency shift of the PEPS with concentrations of the biomolecule.

In yet another aspect, the method of the present invention further comprises the step of binding a tag to the biomolecule that is bound on the surface of the piezoelectric plate sensor. The tag may be selected from, for example, a secondary antibody and a receptor.

In yet another aspect, the method of the present invention further comprises the step of refurbishing the PEPS for reuse.

In yet another aspect, the method of the present invention is employed for diagnosis of breast cancer.

In yet another aspect, the method of the present invention is employed for diagnosis of acute myocardial infarction.

In yet another aspect, the method of the present invention is employed for diagnosis of diarrheal disease.

In yet another aspect, the method of the present invention is employed for diagnosis of *Clostridium difficile* infection.

In yet another aspect, the method of the present invention is employed for diagnosis of Hepatitis B viral infection.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described various embodiments of the invention.

BRIEF DESCRIPTION OF THE DRAWINGS

The application file contains at least one drawing executed in color. Copies of this patent application publication with color drawings will be provided by the Office upon request and payment of the necessary fee.

FIGS. 9A and 9B are scanning electron microscope (SEM) micrographs showing respectively a cross-sectional view and a top-view of an MPS insulation layer produced by coating for 36 hours using a 1% MPS solution in ethanol with 1% DI water at pH=9.0.

FIG. 9C is a SEM micrograph showing a cross-sectional view of an MPS insulation layer produced by coating for 36 hours using a 1% MPS solution in ethanol with 1% DI water at pH=8.0.

FIG. 10A is a SEM micrograph showing a cross-sectional view of an MPS insulation layer produced by coating for 36 hours using a 0.1% MPS solution in ethanol with 0.5% DI water at pH=9.

FIG. 10B is a SEM micrograph showing a top view of an MPS insulation layer produced by coating for 36 hours using a 0.1% MPS solution in ethanol with 0.5% DI water at pH=9.

and $k_{31}$=0.21-0.23 (full triangles). Also plotted is the absorbance versus concentration of ELISA (open squares) for comparison.

Figure 21:
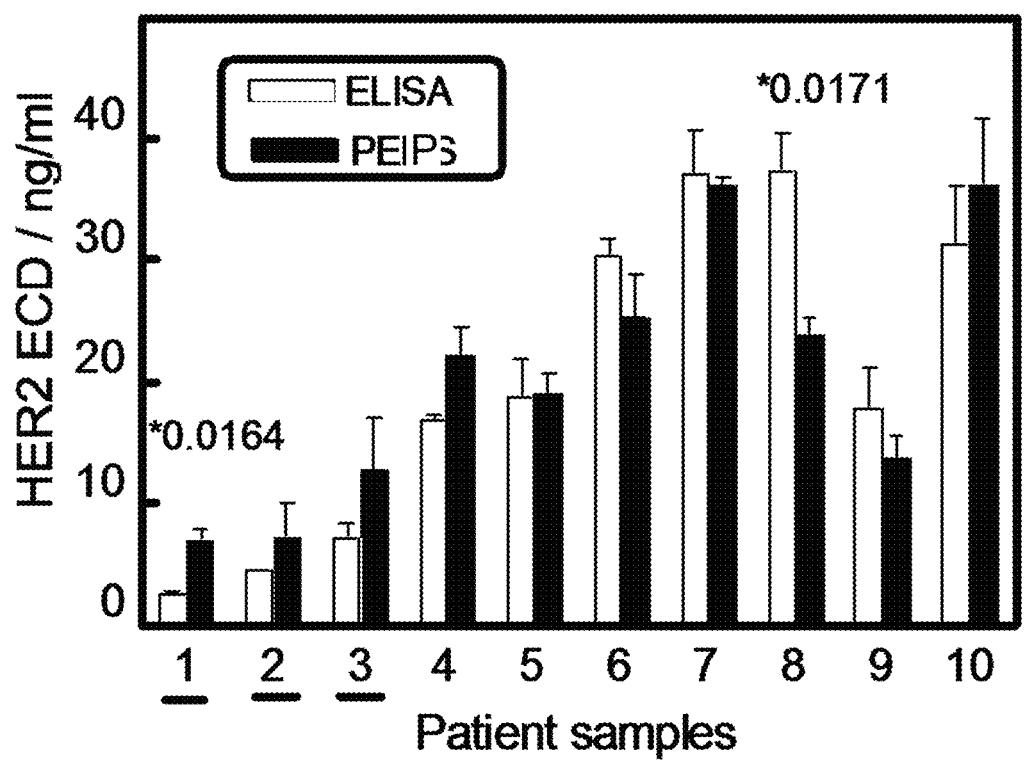

FIG. 21 shows comparison of detecting HER2 in the serum of breast cancer patients and healthy controls by HER2 ELISA and piezoelectric plate sensors (PEPS) functionalized with anti-HER2 antibody. Negative control serum samples (#s 1-3, underlined) and serum samples from patients with HER2 positive breast cancer (#4-10) were used.

Figure 22:
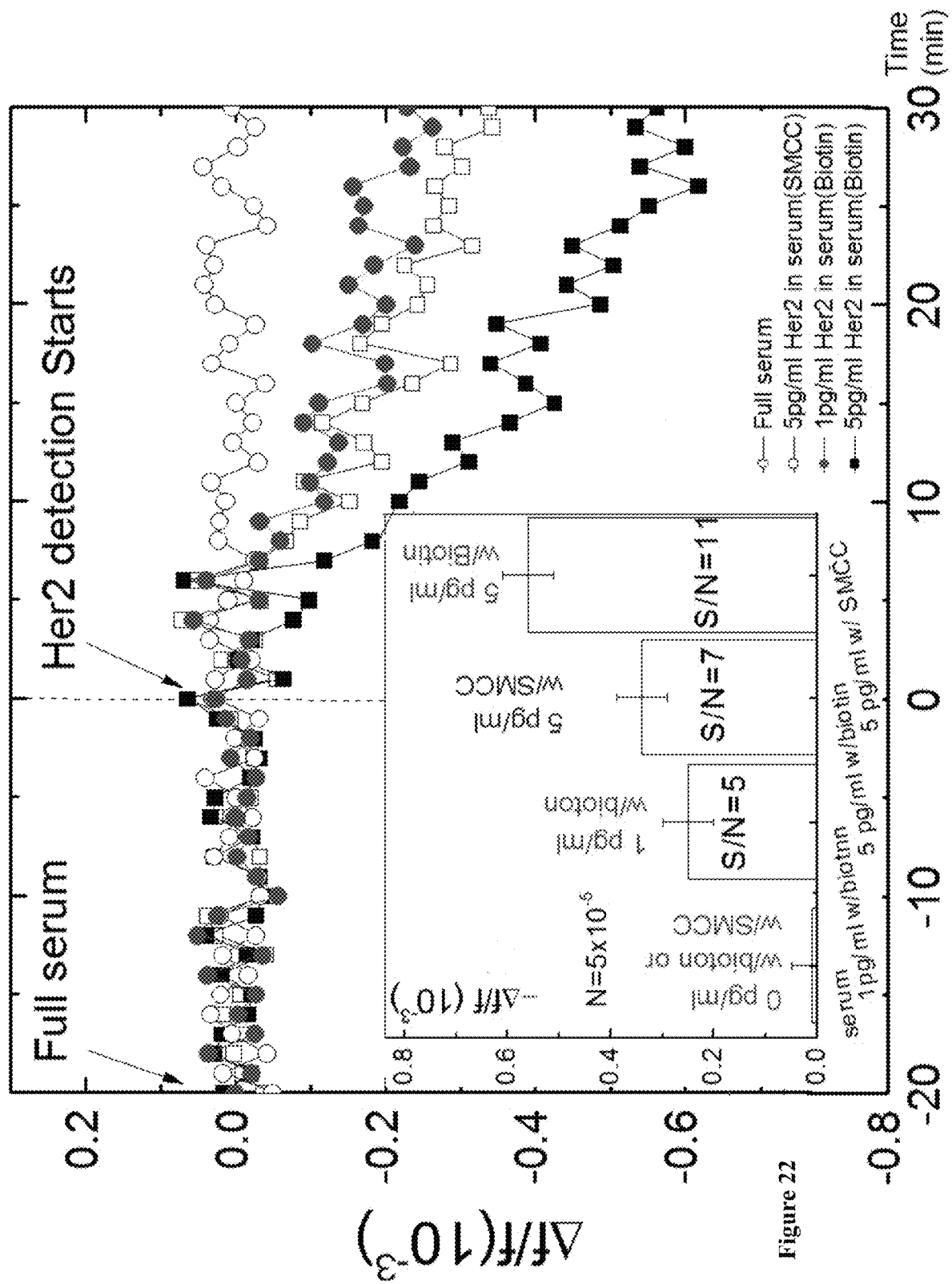

FIG. 22 shows $\Delta f/f(10^{-3})$ versus time for HER2 detection in full serum using piezoelectric plate sensors functionalized with biotin at 0 (open circles), 1 (full circles), and 5 (full squares) pg/ml of HER2 in the serum and the same sensors functionalized with sulfo-SMCC at 5 pg/ml HER2 in the serum.

Figure 23:
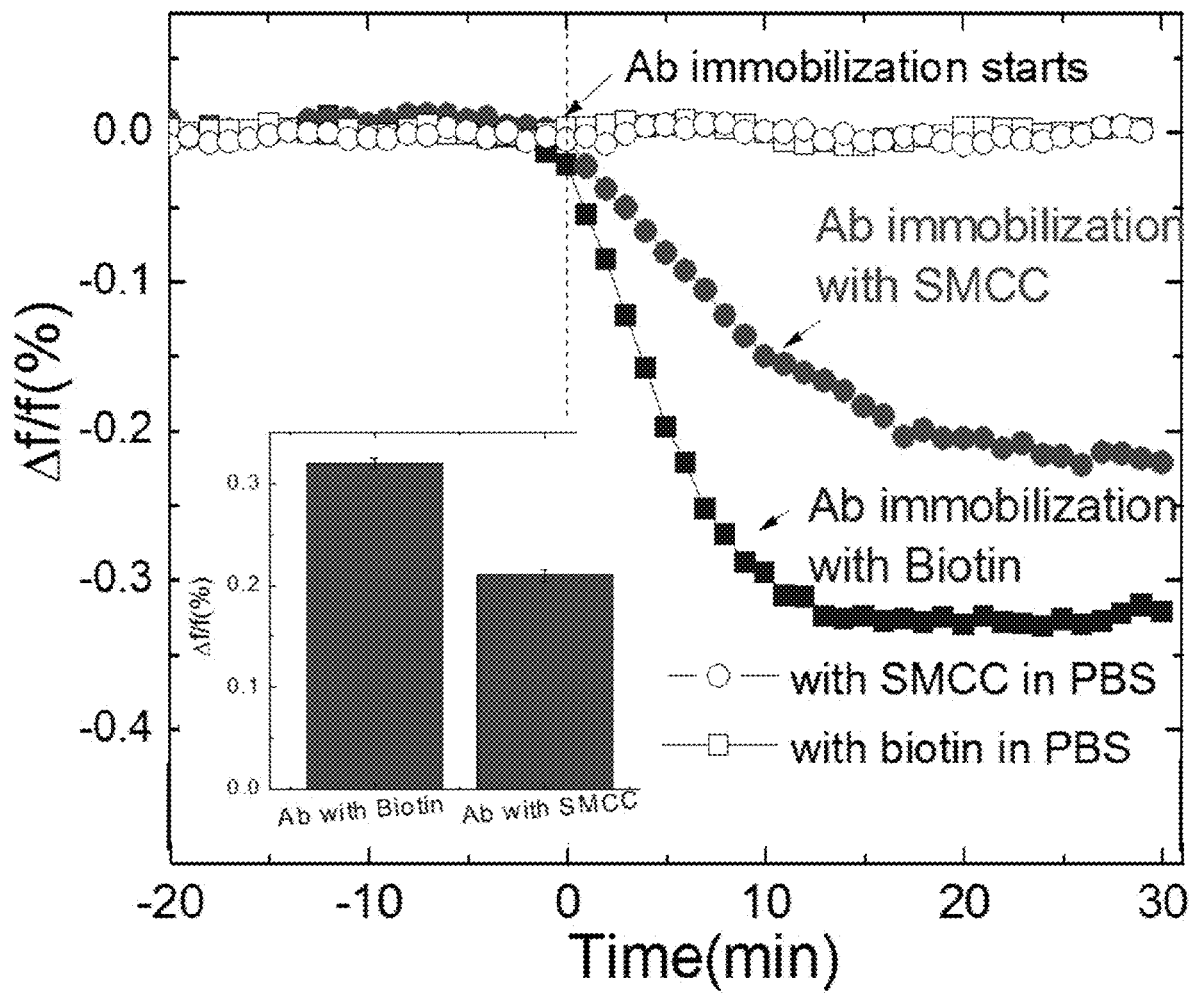

FIG. 23 shows $\Delta f/f$ (%) versus time during antibody binding on piezoelectric plate sensors with a $k_{31}$=0.32 functionalized with sulfo-SMCC (solid circles) and with biotin (solid squares). The hollow circles and hollow squares represent sulfo-SMCC- and streptavidin-functionalized sensors in PBS respectively.

Figure 24:
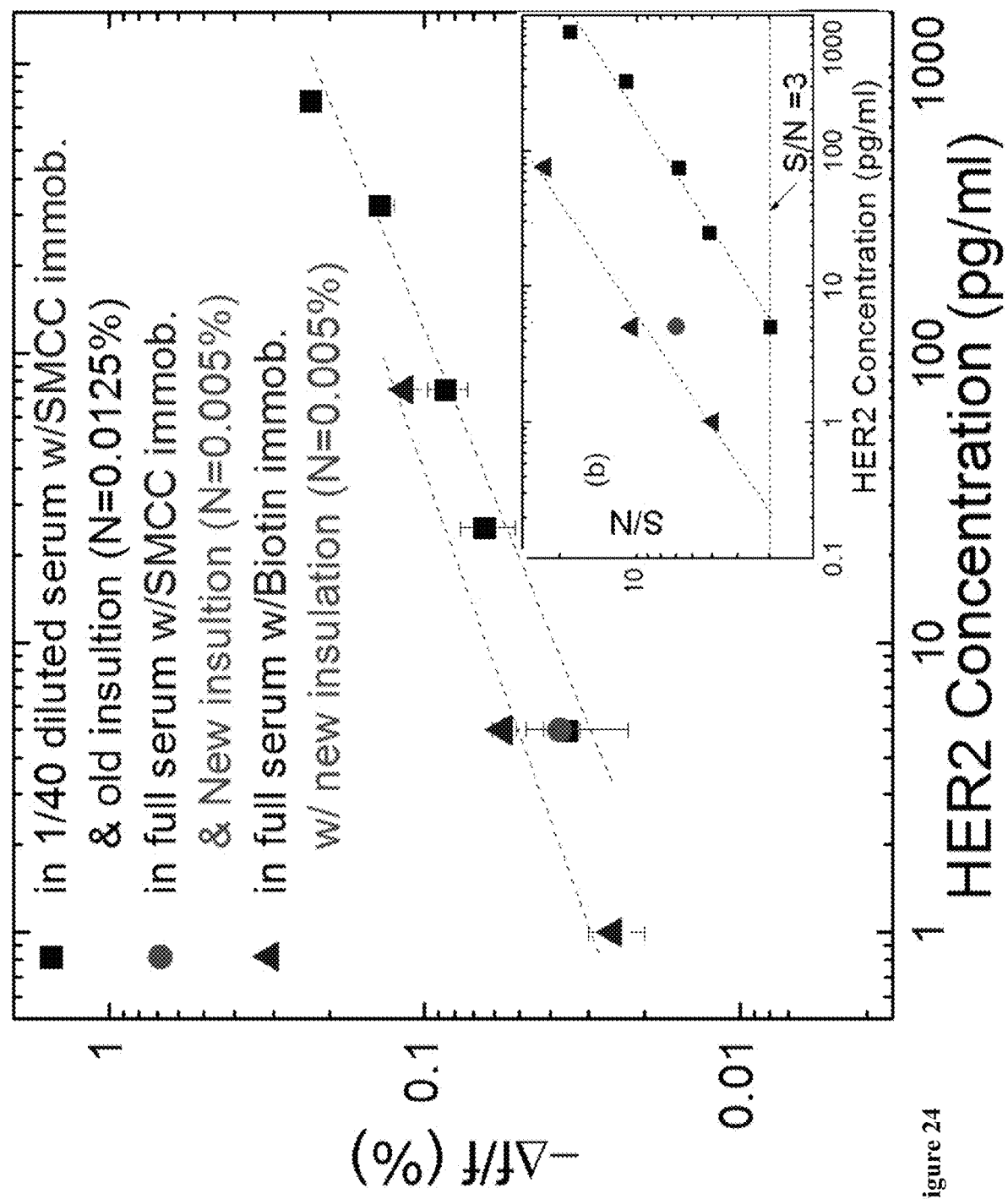

FIG. 24 is a summary plot of $-\Delta f/f$ (%) versus HER2 concentration using piezoelectric plate sensors with various insulation and binding conditions in various serums. The insert shows the corresponding S/N versus HER2 concentration.

Figure 25:
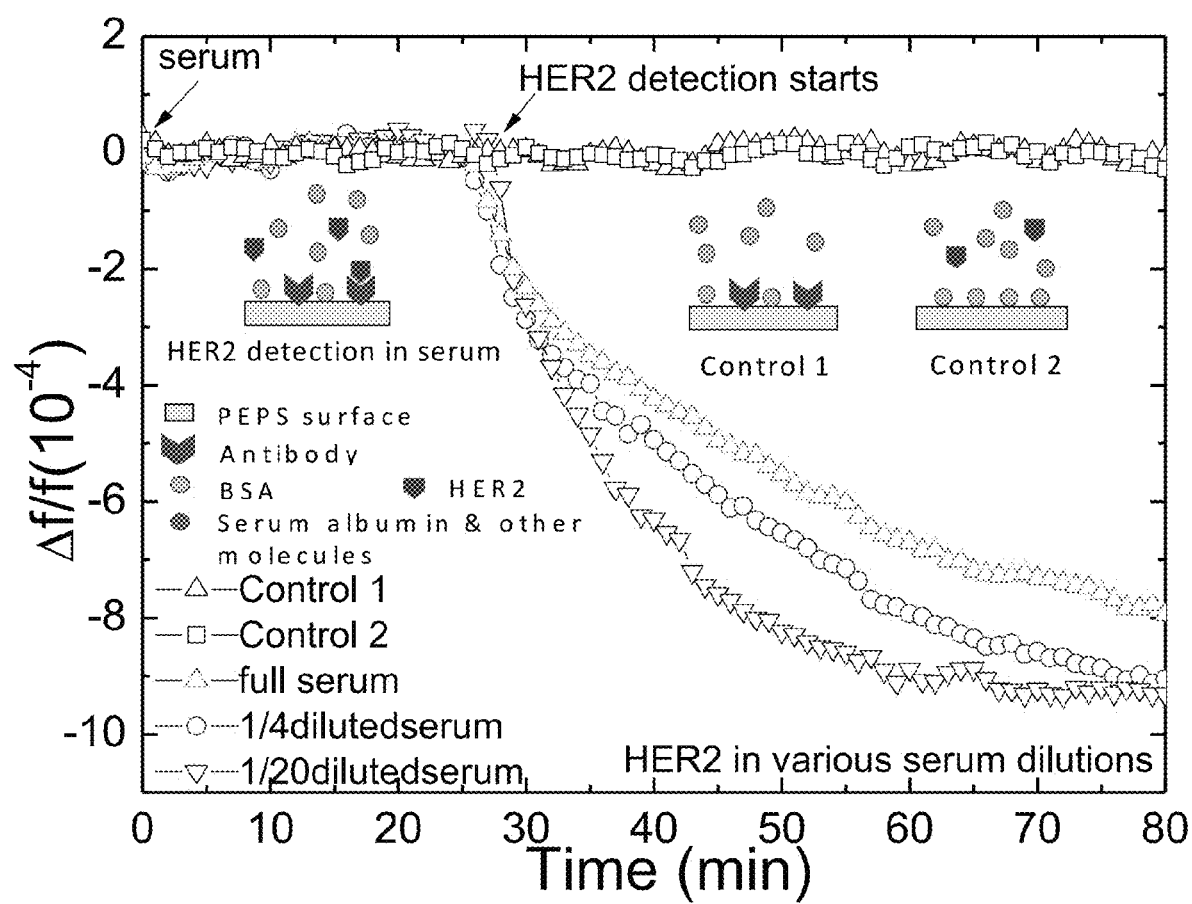

FIG. 25 shows $\Delta f/f(10^{-4})$ versus time using piezoelectric plate sensors for detecting 75 pg/ml HER2 in various diluted sera. A schematic of the detection scheme is shown in the insert. Control 1 and control 2 used detection with antibody-coated PEPS in blank full serum and detection with PEPS with no antibody at 75 pg/ml HER2 in full serum, respectively.

Figures 26A, 26B:
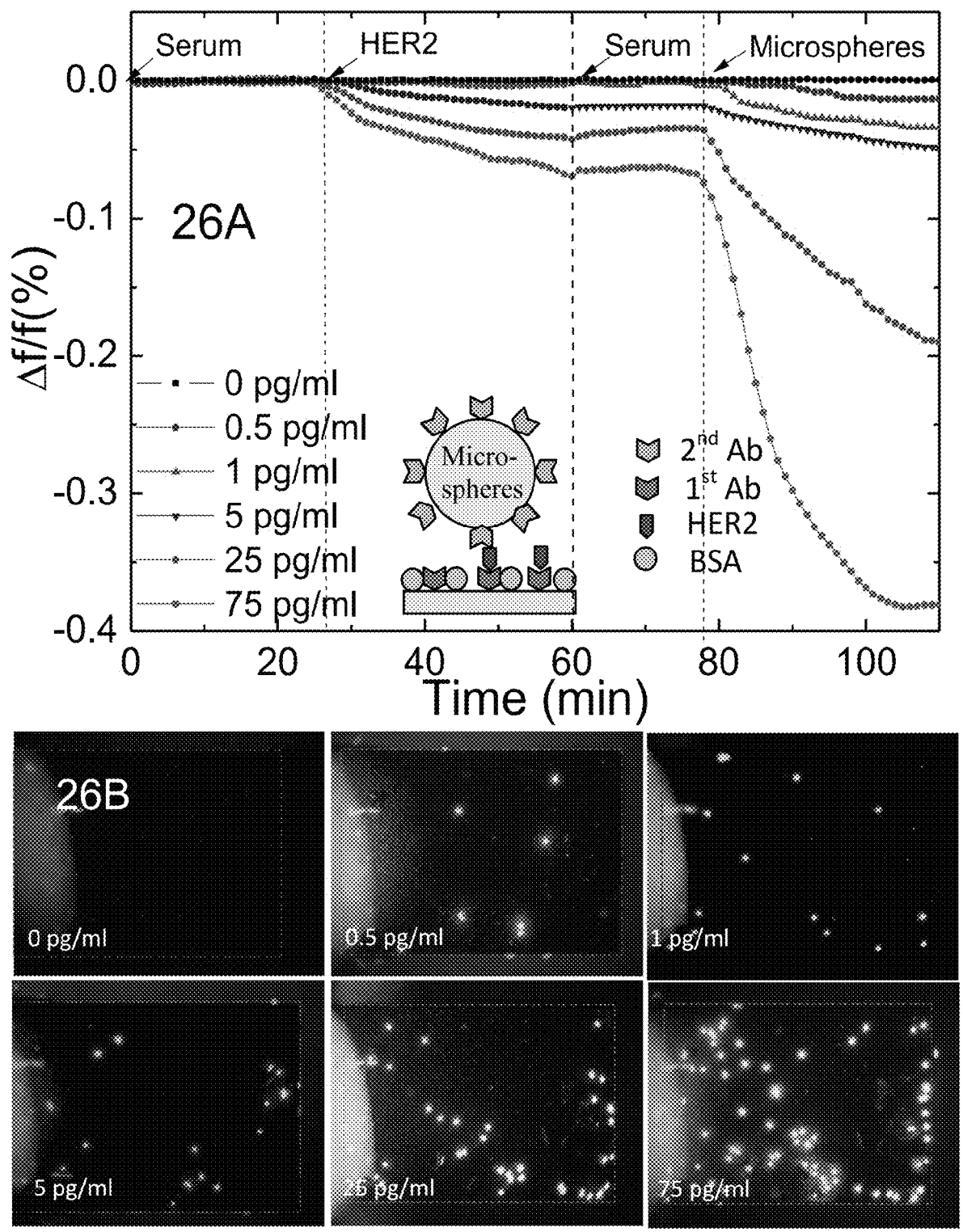

FIG. 26A shows $\Delta f/f$ (%) versus time for HER2 detection at 0-75 pg/ml in 1-in-40 diluted serum using piezoelectric plate sensors with $k_{31}$=0.32 for 30 minutes followed by 18 minutes of diluted serum rinsing and 28 minutes of in situ microsphere validation detection.

FIG. 26B shows fluorescent images of the piezoelectric plate sensors showing binding of HER2 on the surface of the sensors.

Figure 27:
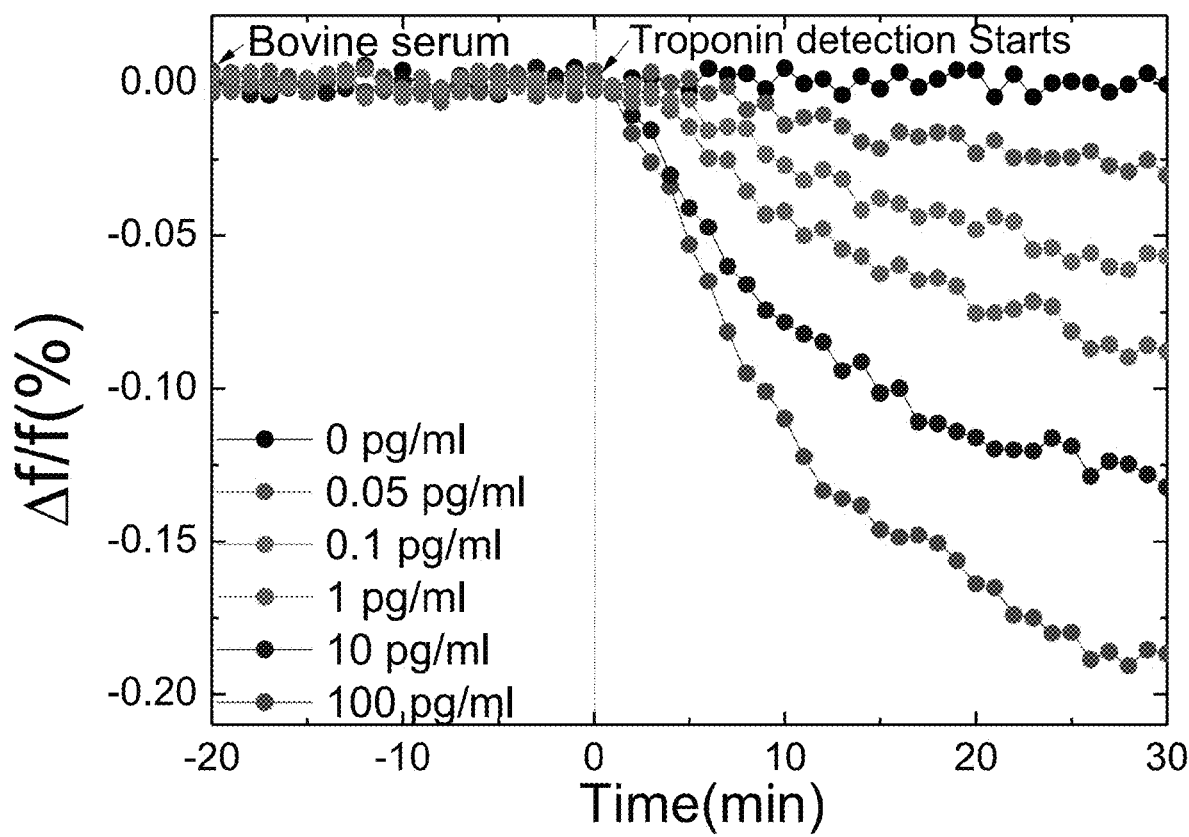

FIG. 27 shows $\Delta f/f$ (%) versus time at various troponin I concentrations spiked in full bovine serum.

Figure 28:
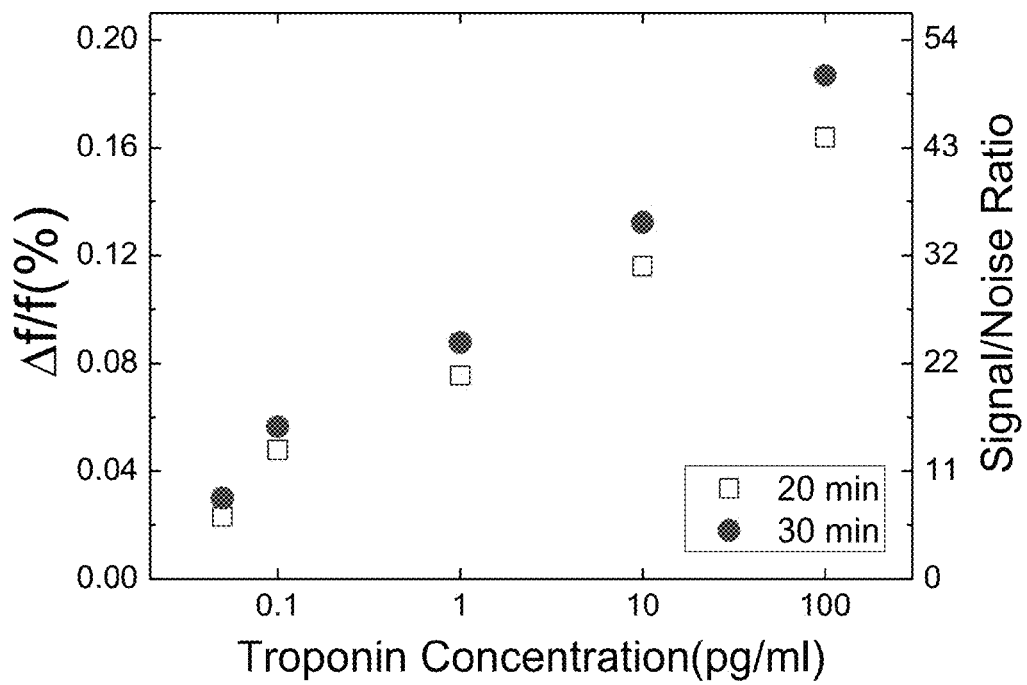

FIG. 28 shows $\Delta f/f$ (%) at 30 minutes (solid circles) and 20 minutes (hollow squares) versus troponin I concentration. Also shown is the signal/noise (S/N) ratio as labeled on the right y-axis.

Figure 29:
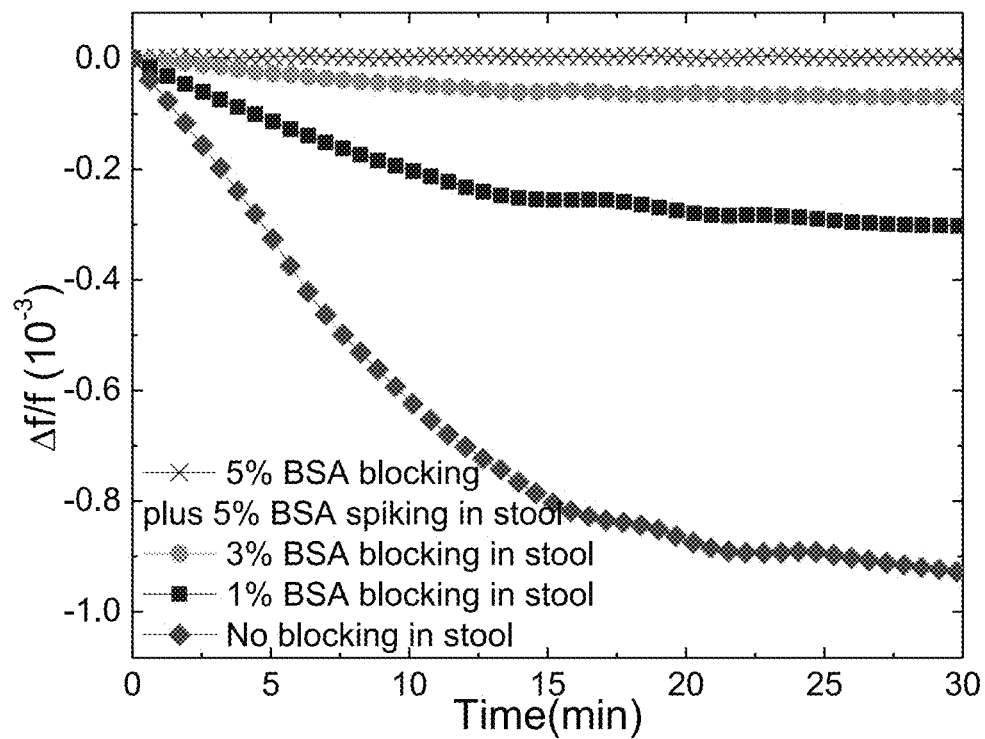

FIG. 29 shows $\Delta f/f$ versus time using piezoelectric plate sensors with different bovine serum albumin (BSA) blocking schemes: 0% (diamonds), 1% (squares) and 3% (circles) BSA blocking in stool and 5% BSA blocking in stool spiked with 5% BSA (crosses).

Figure 30:
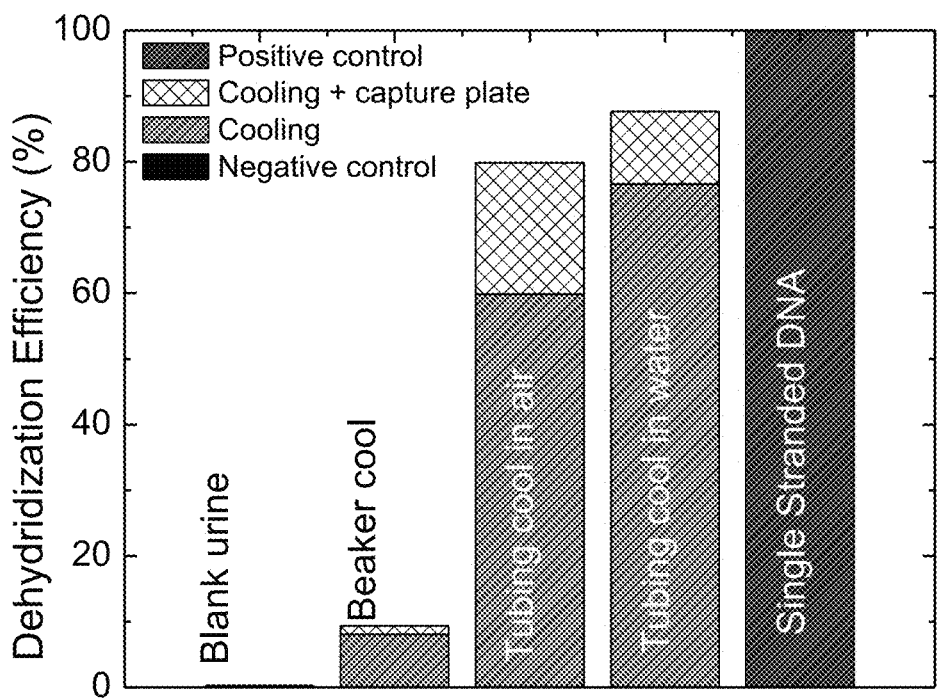

FIG. 30 shows $\Delta f_{bacterial\ DNA}/\Delta f_{ssDNA}$ using piezoelectric plate sensors.

Figure 31A:
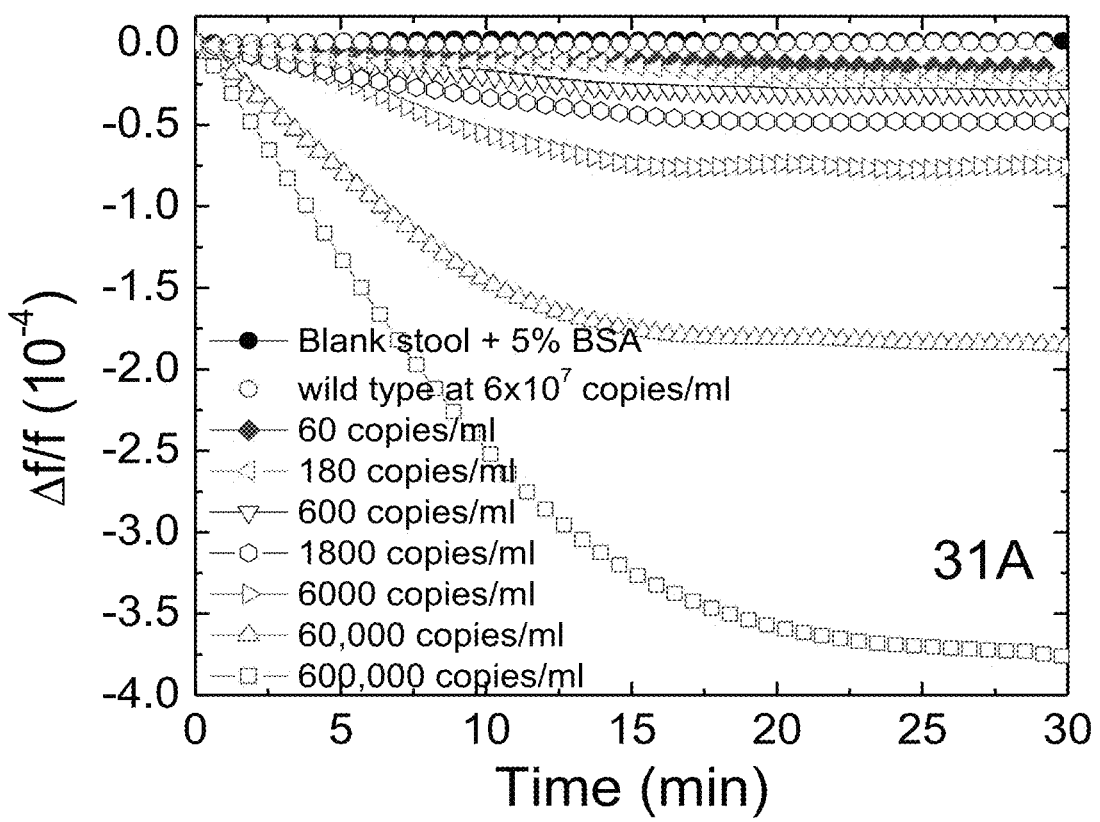

FIG. 31A shows $\Delta f/f$ versus time for detection of double-stranded bacterial DNA in stool at 50° C. at various concentrations—also included are the negative control (blank stool with 5% BSA) (solid circles) and the wild type at $6\times10^7$ copies/ml (hollow circles).

Figure 31B:
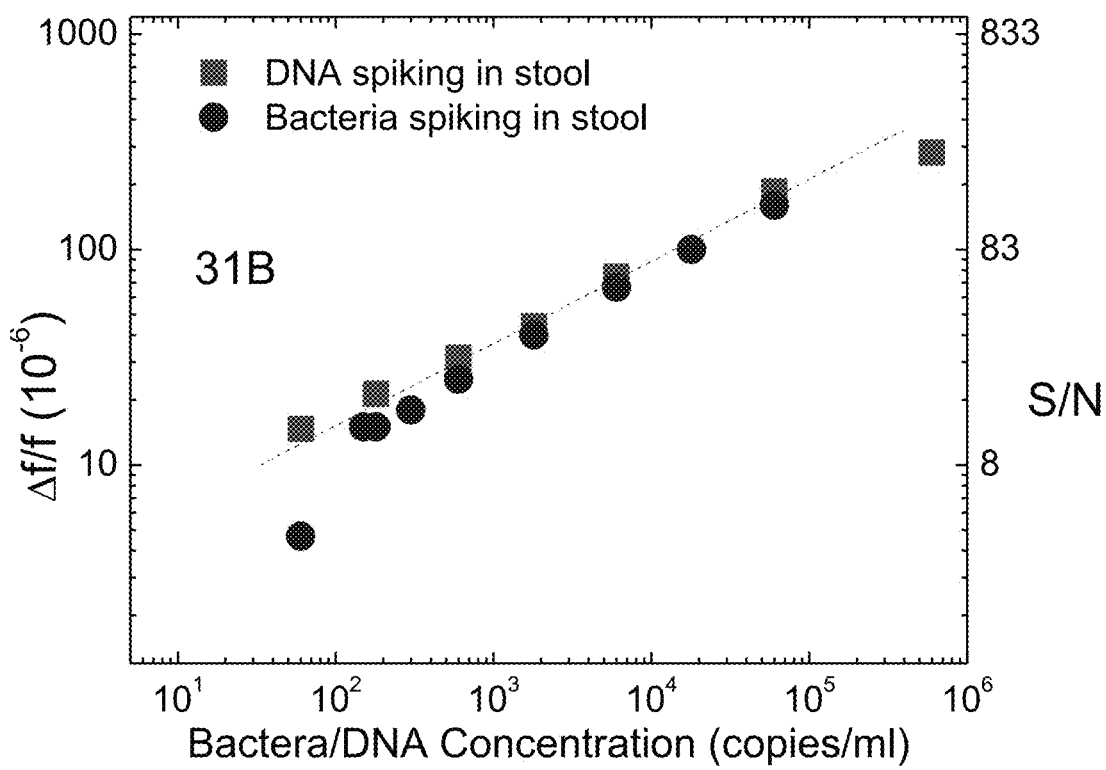

FIG. 31B shows $-\Delta f/f$ and S/N versus bacterial DNA concentration in stool samples.

Figures 32A, 32B:
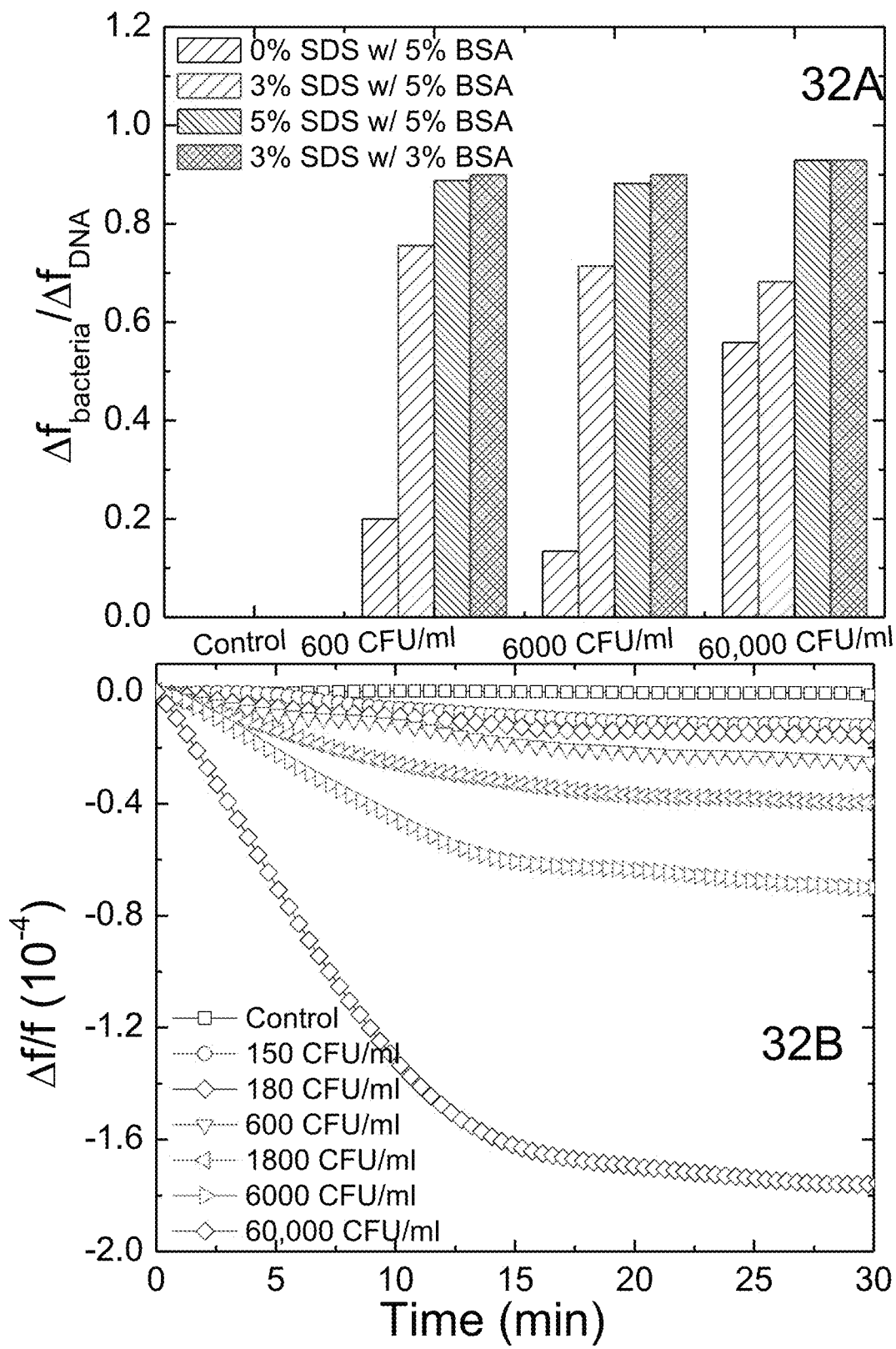

FIG. 32A shows $\Delta f_{bacteria}/\Delta f_{DNA}$ with various BSA & SDS (sodium dodecyl sulfite) spiking conditions in stool samples.

FIG. 32B shows $\Delta f/f(10^{-4})$ versus time for detection of E. coli bacteria at different concentrations with 5% BSA and 3% SDS blocking and 3% BSA and 3% SDS spiking in stool.

Figure 33:
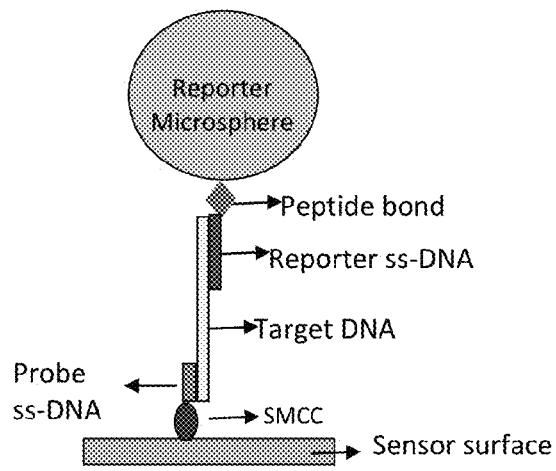

FIG. 33 shows a schematic diagram of a device for measuring target DNA using piezoelectric plate sensors with a reporter microsphere.

Figure 34:
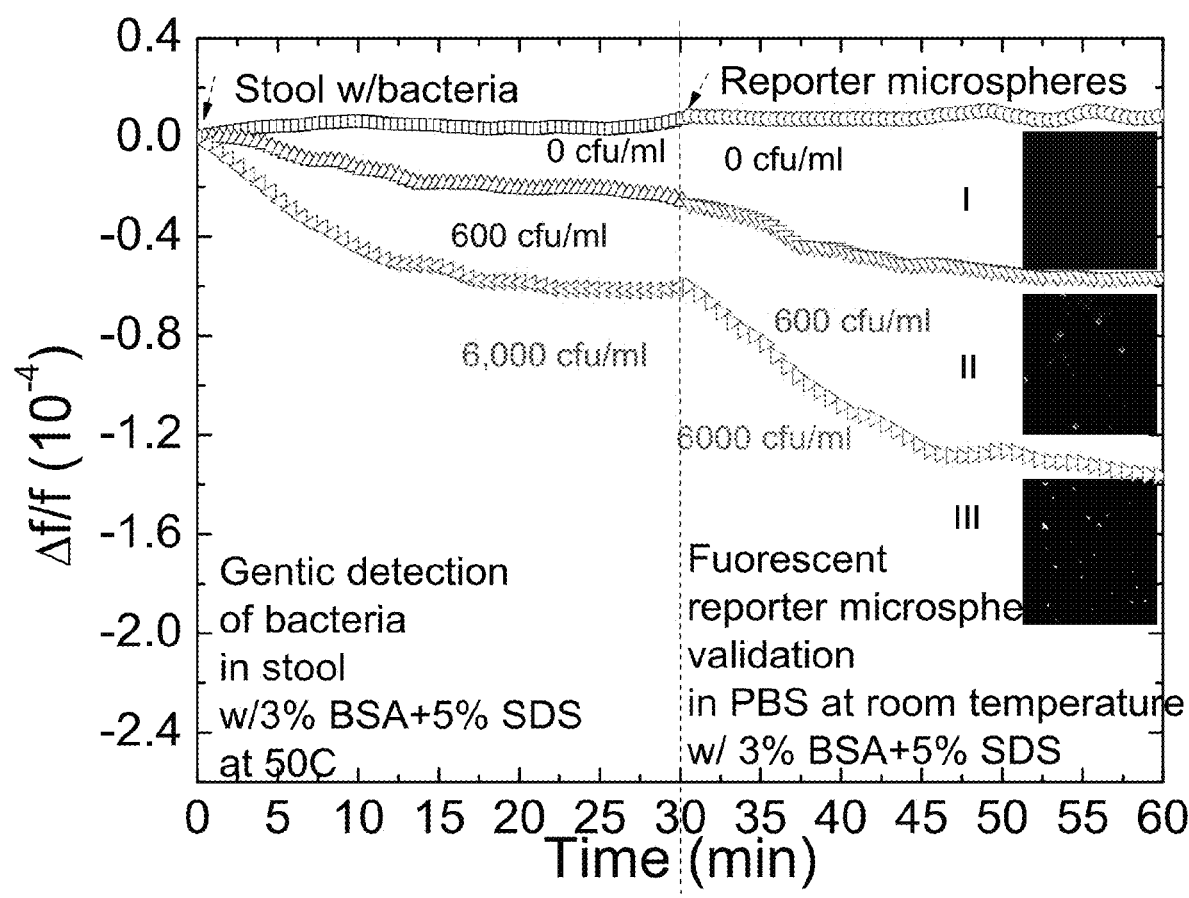

FIG. 34 shows $\Delta f/f(10^{-4})$ versus time for detection of a bacterial genetic signature in stool for 30 minutes followed by 30 minutes of in situ binding using a reporter microsphere detection. The inserts show the images of the fluorescent reporter microsphere captured on the PEPS surface.

Figure 35A:
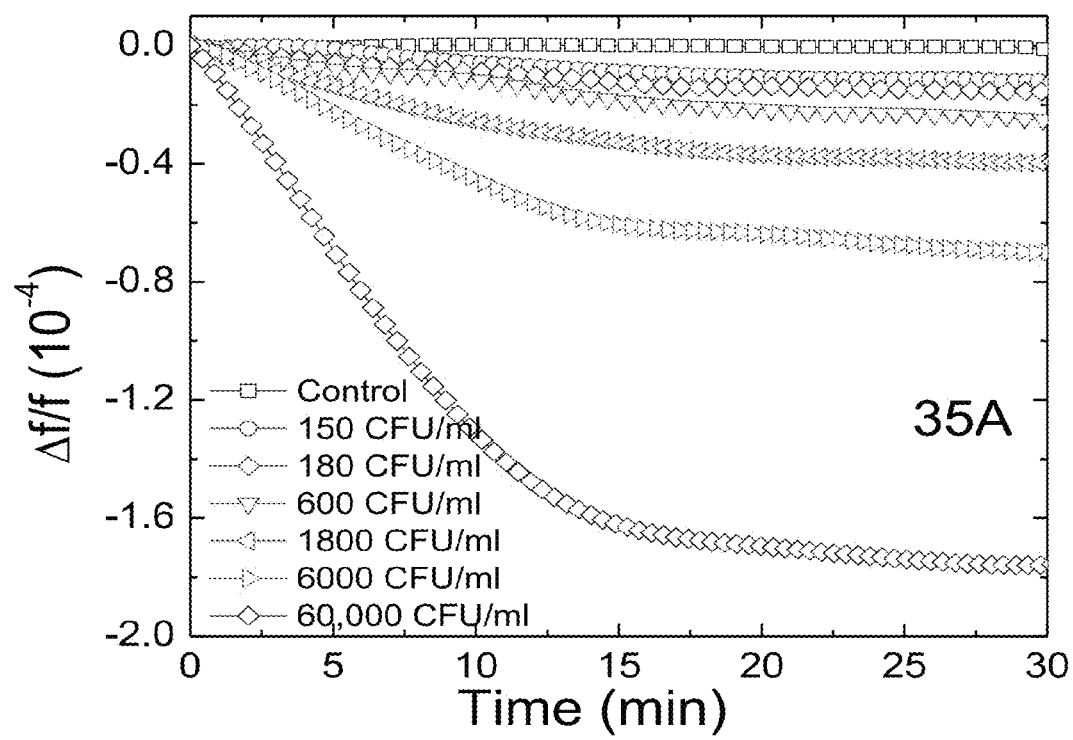

FIG. 35A shows $\Delta f/f(10^{-4})$ versus time in detecting the genetic signature of E. coli O157:H7 spiked in stool.

Figure 35B:
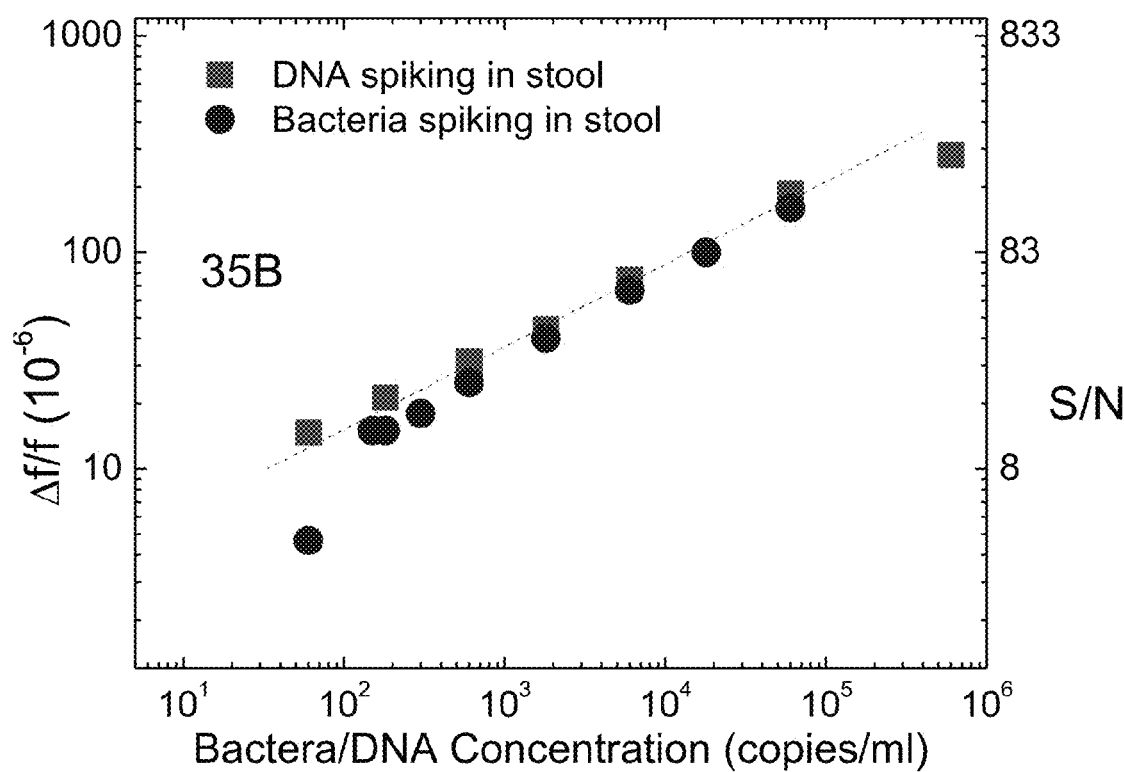

FIG. 35B shows $-\Delta f/f$ at t=30 min versus E. coli concentration in stool. Also shown are $-\Delta f/f$ at t=30 min of detection of E. coli DNA spiked in stool versus the DNA concentrations.

Figure 36:
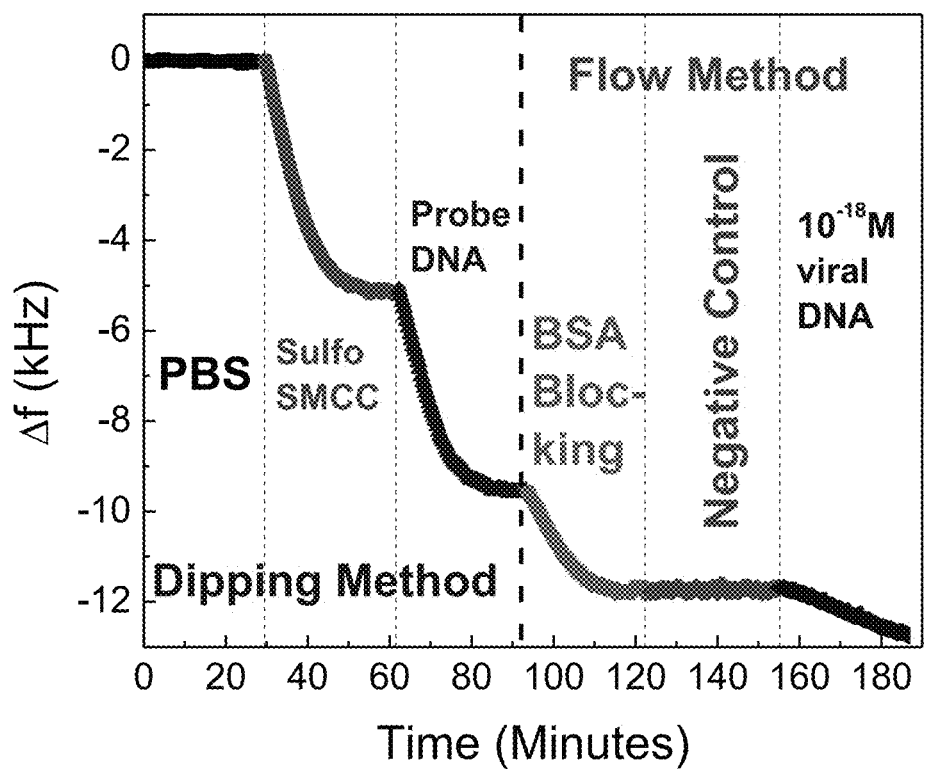

FIG. 36 shows $\Delta f(kHz)$ versus time for sensors using various binding and blocking steps and detection of double stranded viral DNA spiked at $1\times10^{-18}$M in simulated serum.

Figure 37A:
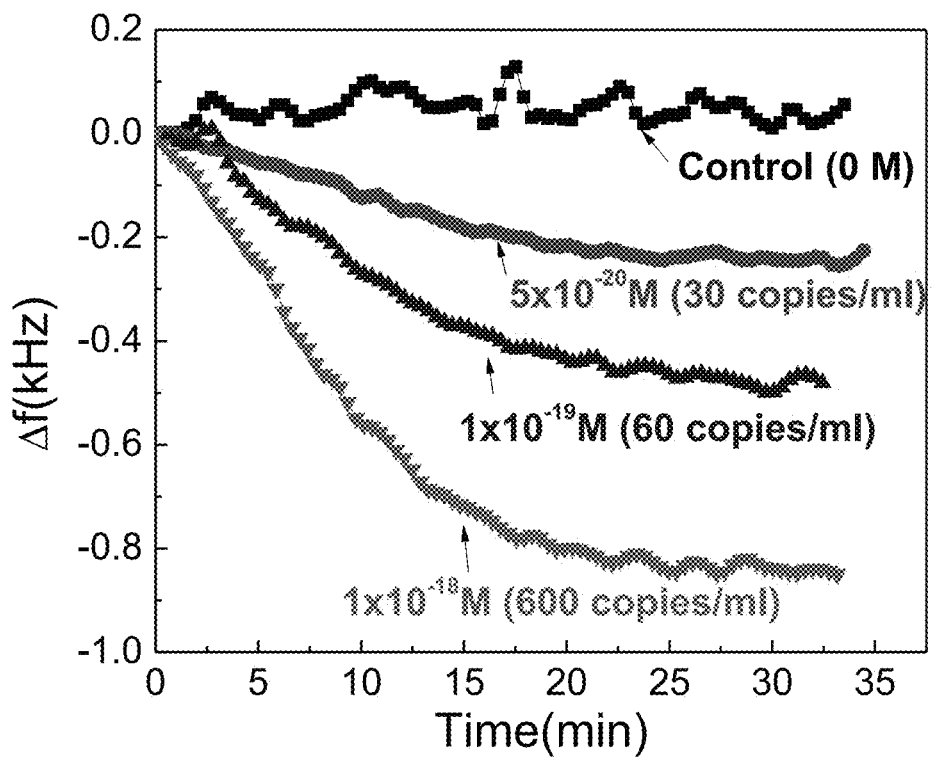

FIG. 37A shows $\Delta f(kHz)$ versus time for detection of viral DNA at various concentrations in simulated serum.

Figure 37B:
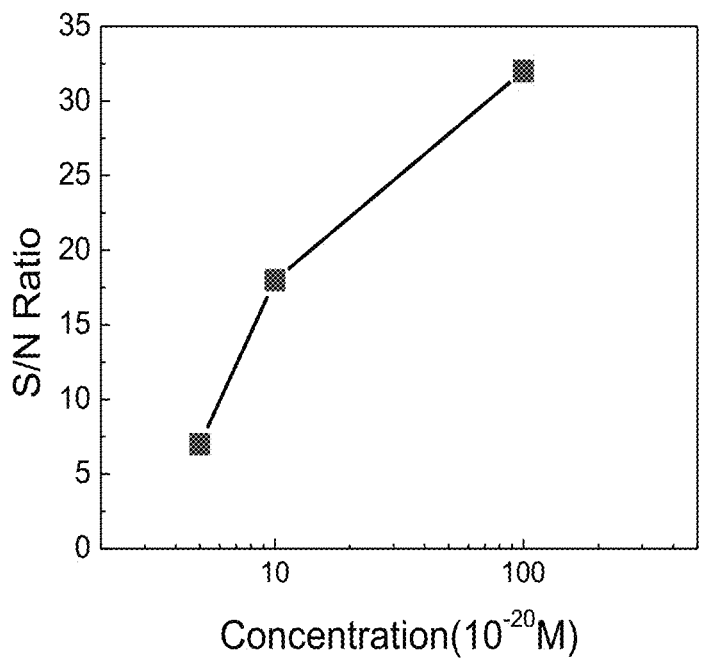

FIG. 37B shows the signal to noise ratio versus viral DNA concentration in simulated serum.

Figure 38:
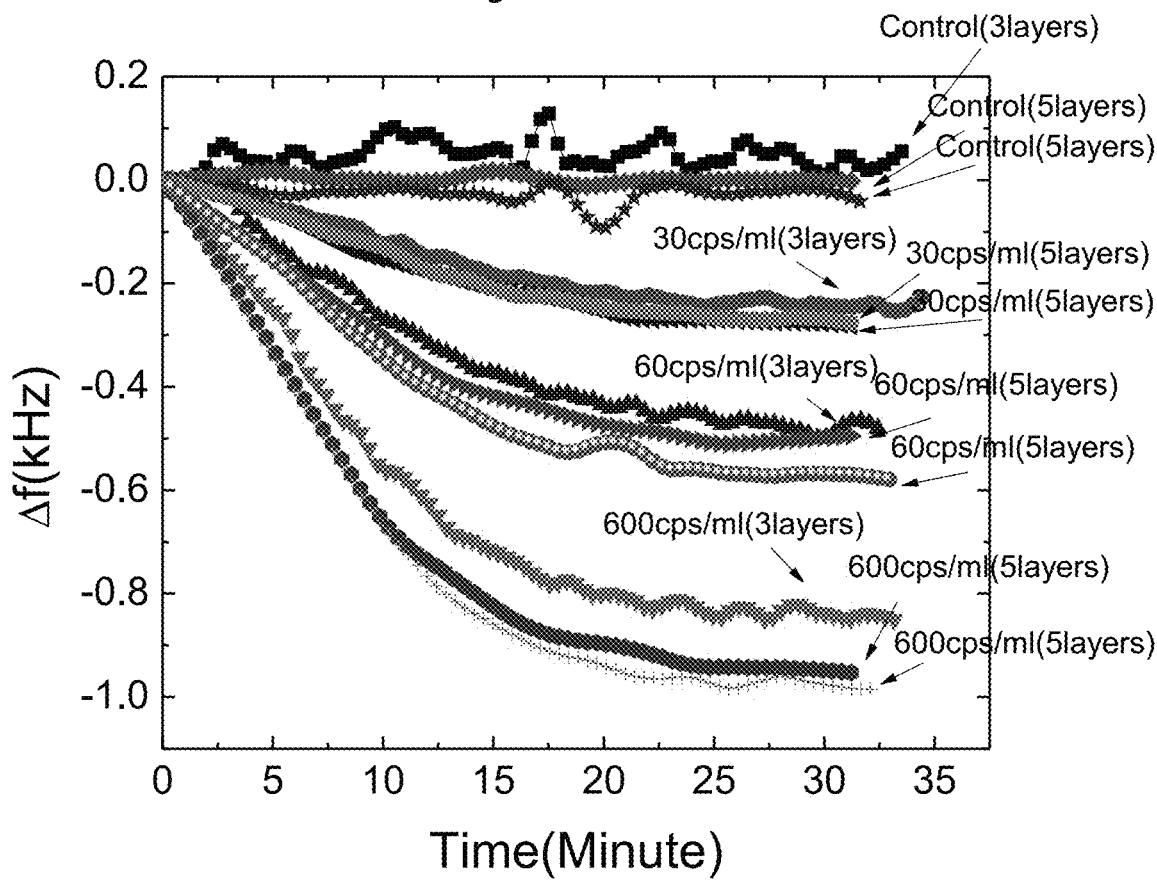

FIG. 38 shows $\Delta f$ (kHz) versus time using piezoelectric plate sensors with either 3 or 5 insulation layers in the detection of viral DNA in serum.

Figure 39A:
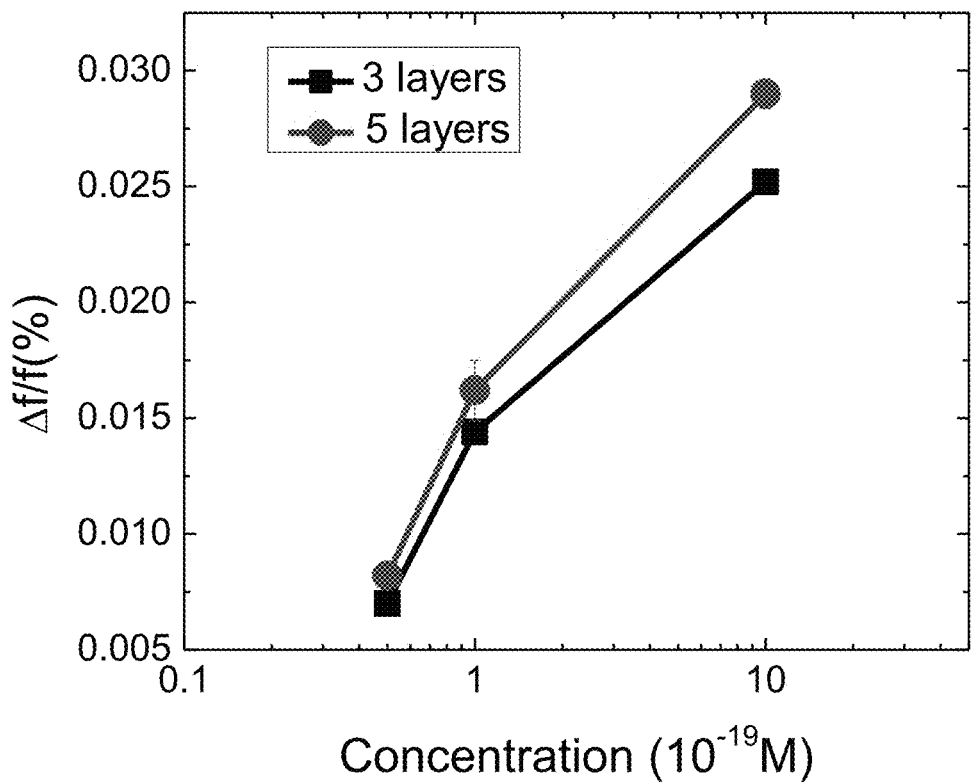

FIG. 39A shows $\Delta f/f$ (%) versus viral DNA concentration using piezoelectric plate sensors with 3 insulation layers (squares) and 5 insulation layers (circles).

Figure 39B:
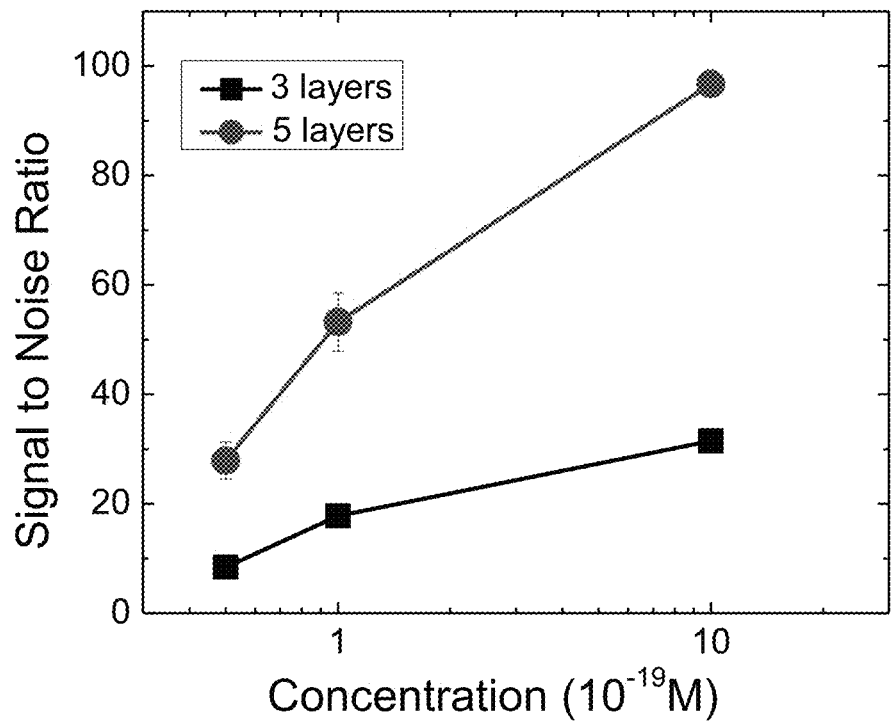

FIG. 39B shows the signal to noise ratio versus viral DNA concentration using piezoelectric plate sensors with 3 insulation layers (squares) and 5 insulation layers (circles).

Figure 40:
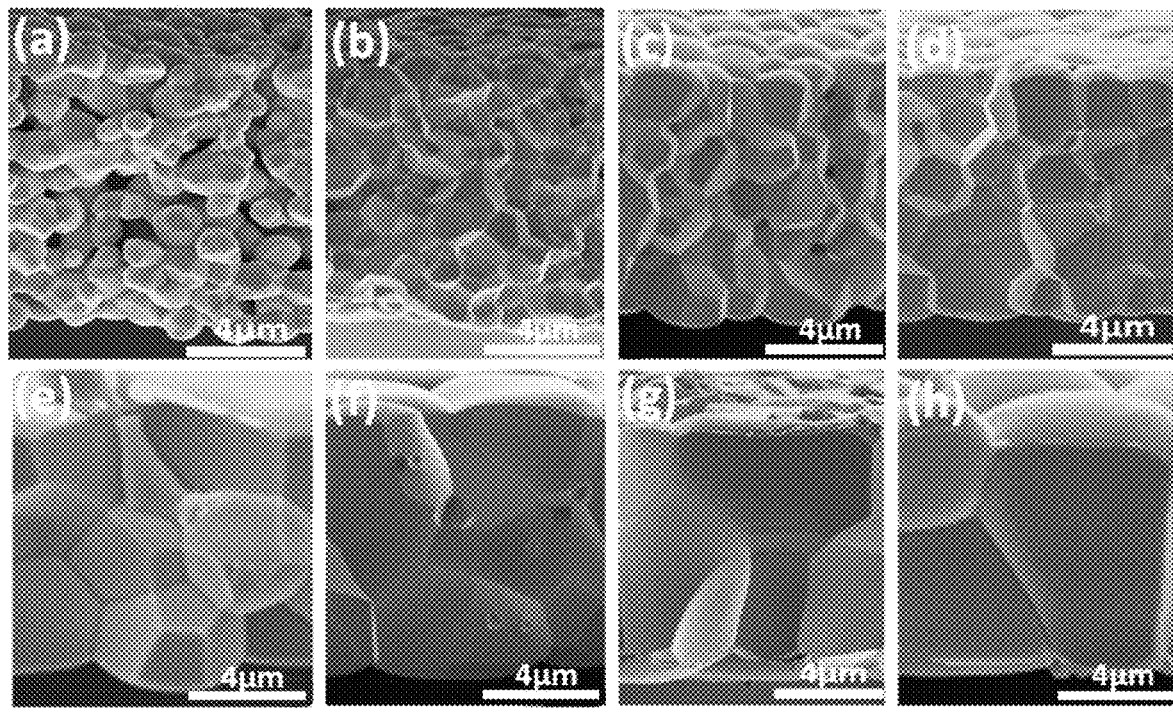

FIG. 40 shows scanning electron microscopy (SEM) images of cross-sections of different 8 μm thick lead magnesium niobate-lead titanate (PMN-PT) piezoelectric plate sensor having different grain sizes.

Figure 41:
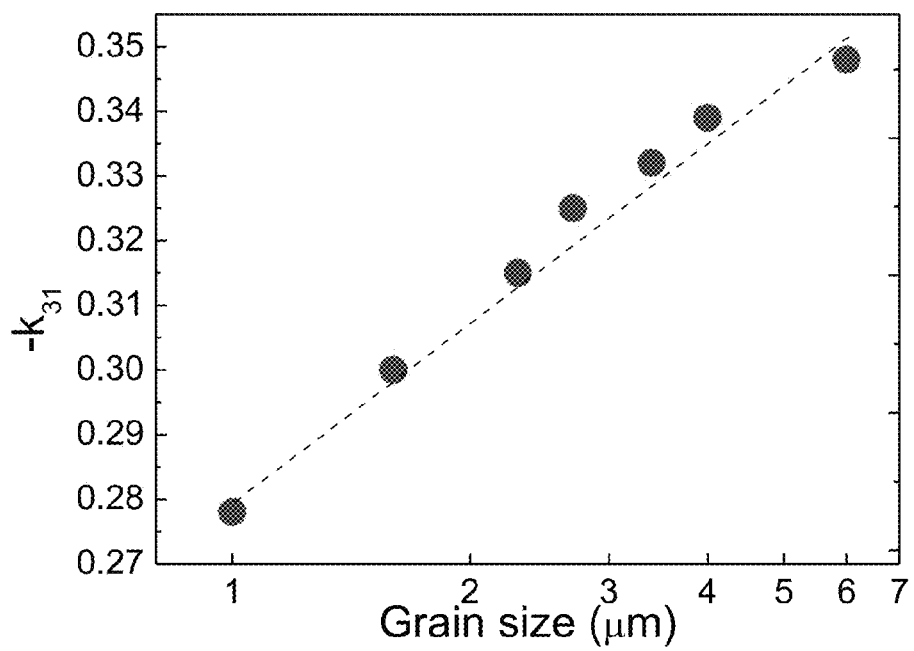

FIG. 41 shows the detection $-k_{31}$ verses grain size of an 8-μm thick PMN-PT piezoelectric plate sensor demonstrating that the $-k_{31}$ of the sensor increased with an increasing grain size.

Figure 42A:
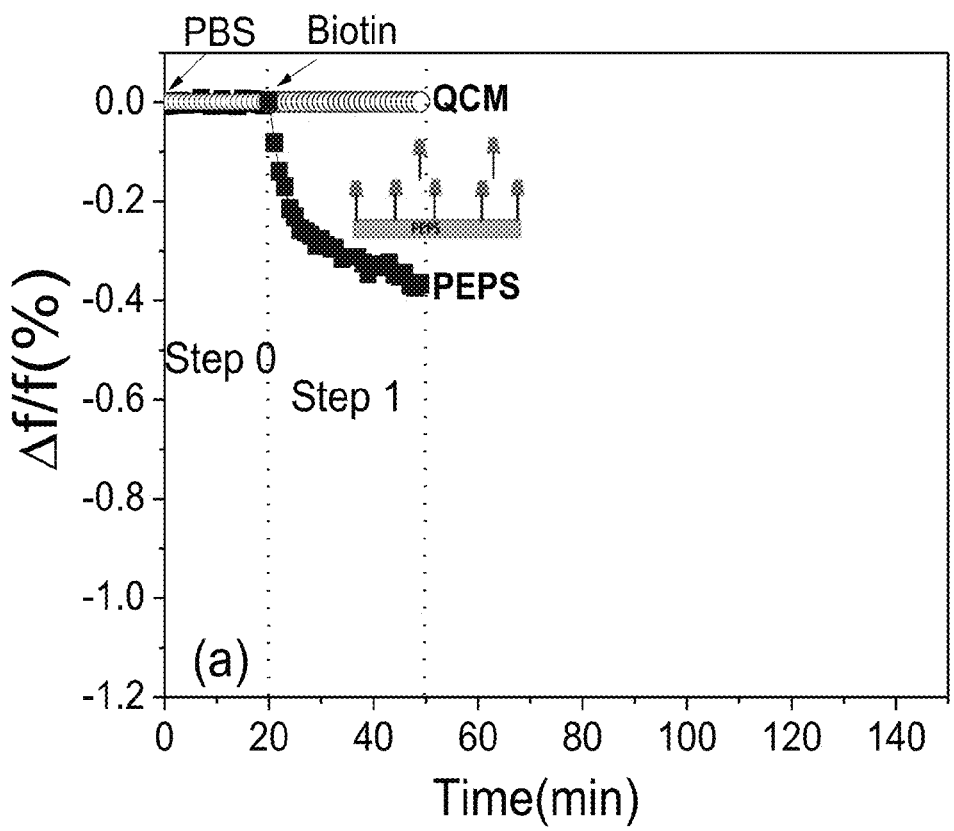
Figure 42B:
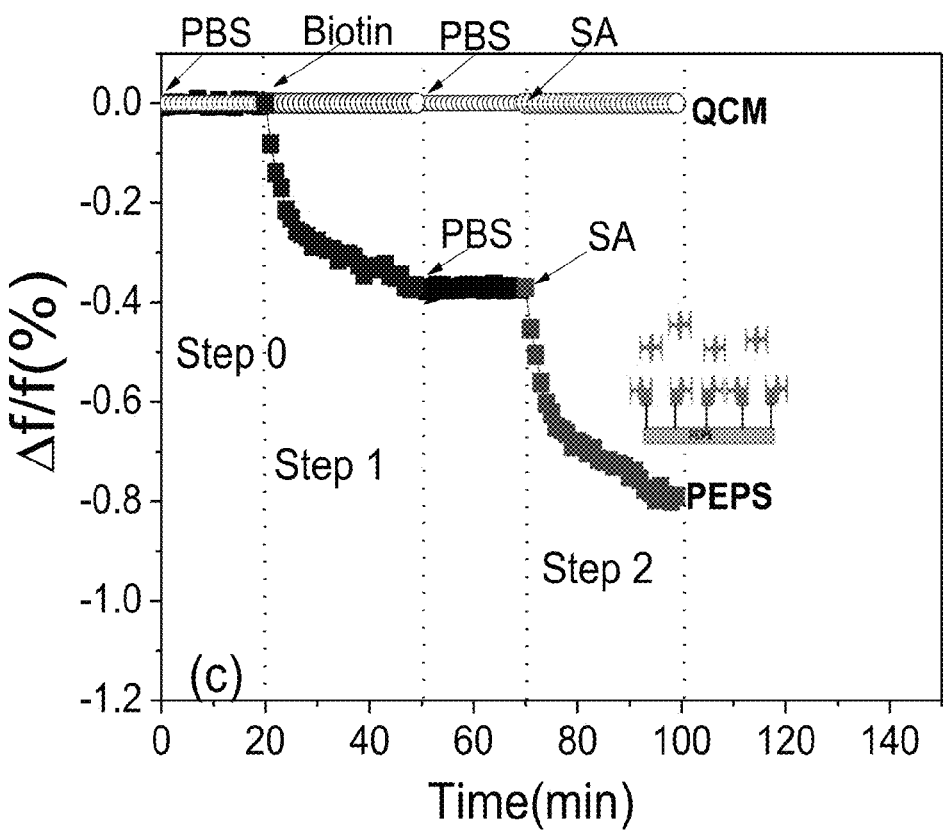
Figure 42C:
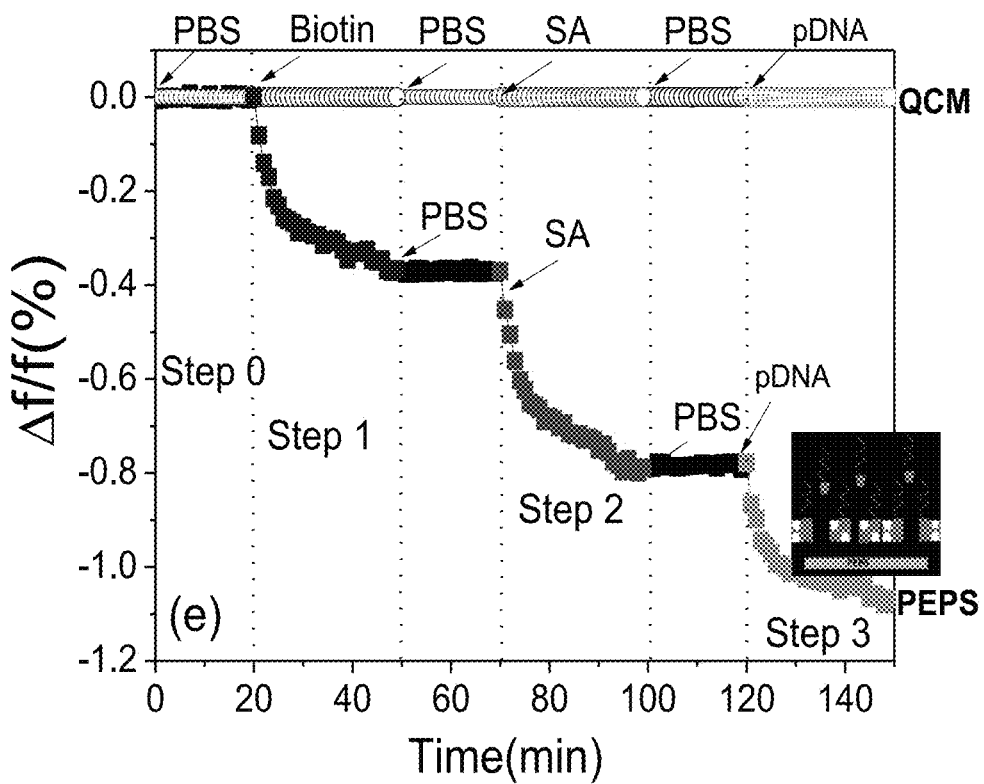

FIGS. 42A-42C show $-\Delta f/f$ versus time of an 8-μm piezoelectric plate sensor having a $-k_{31}$ of about 0.32 during the biotin, streptavidin(SA), and biotinylated probe DNA (pDNA) immobilization steps.

Figure 43A:
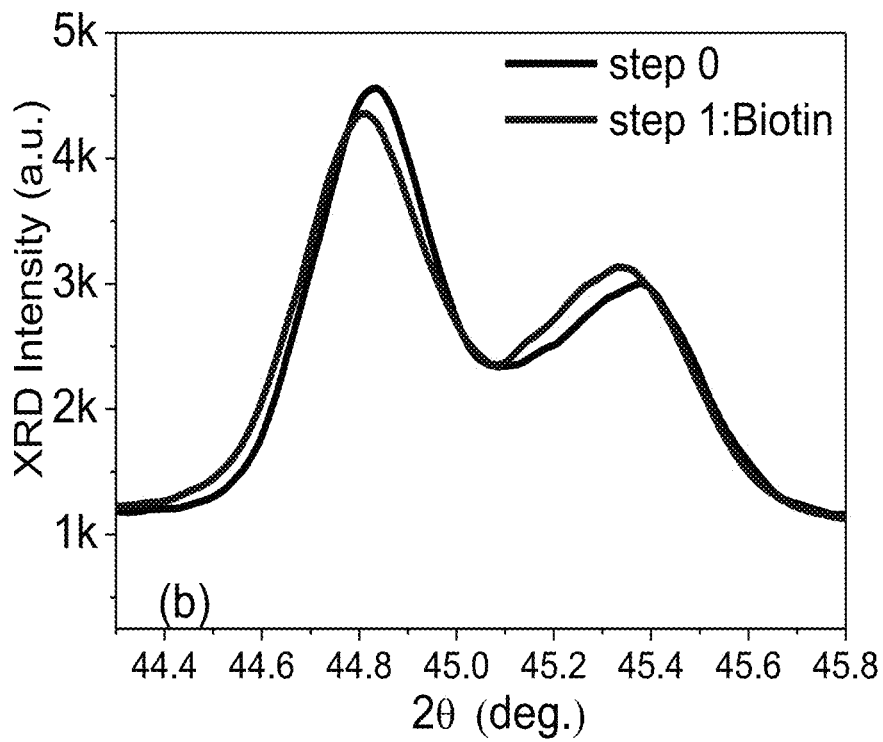
Figure 43B:
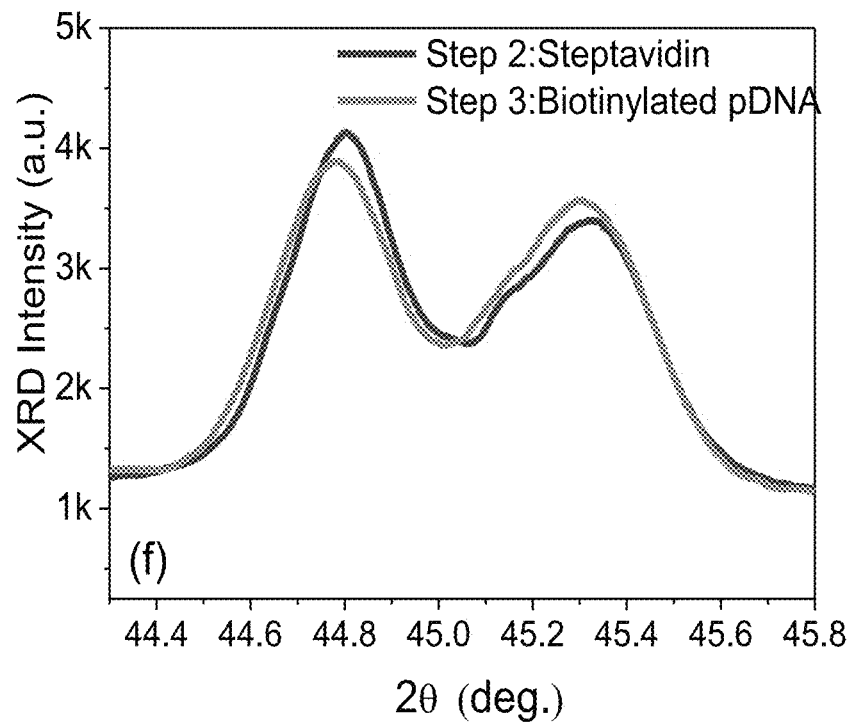
Figure 43C:
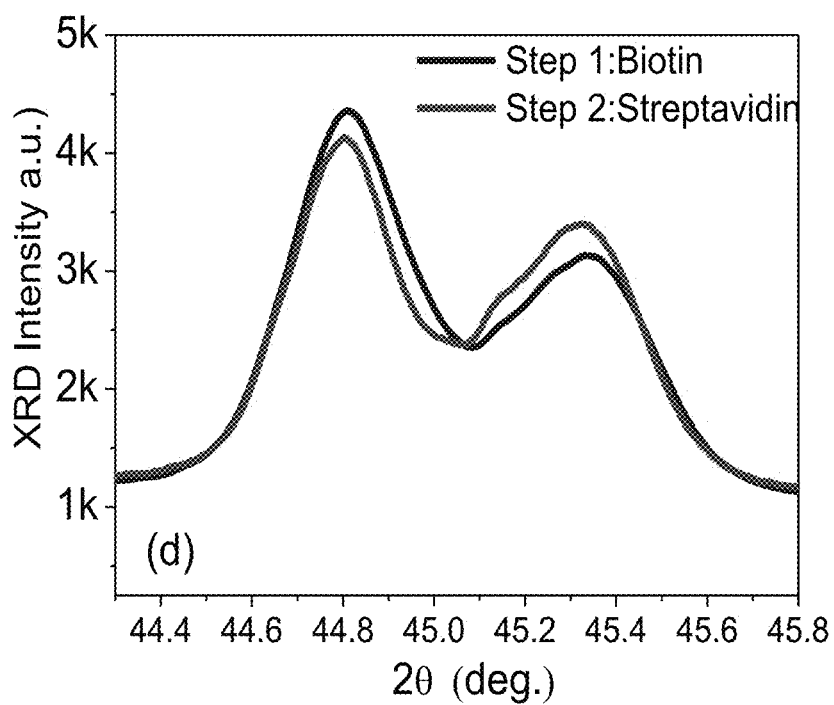

FIGS. 43A-43C show X-ray diffraction patterns of an 8-μm thick PMN-PT surrogate layer of about 1 cm×1 cm of the same sensor for the same biotin, SA, and biotinylated pDNA immobilization steps as shown in FIGS. 42A-42C.

Figure 44A:
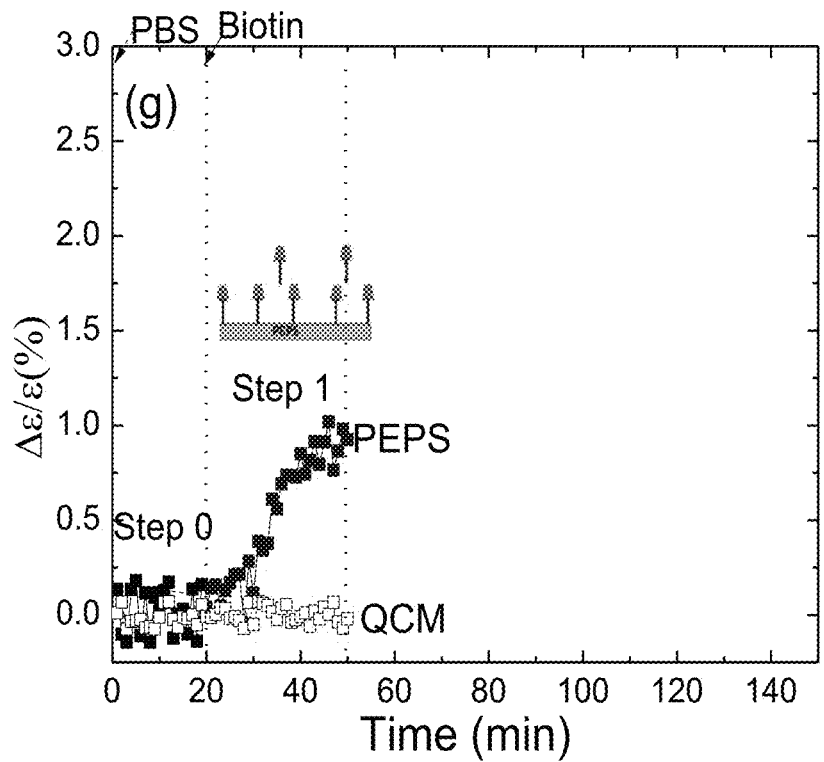
Figure 44B:
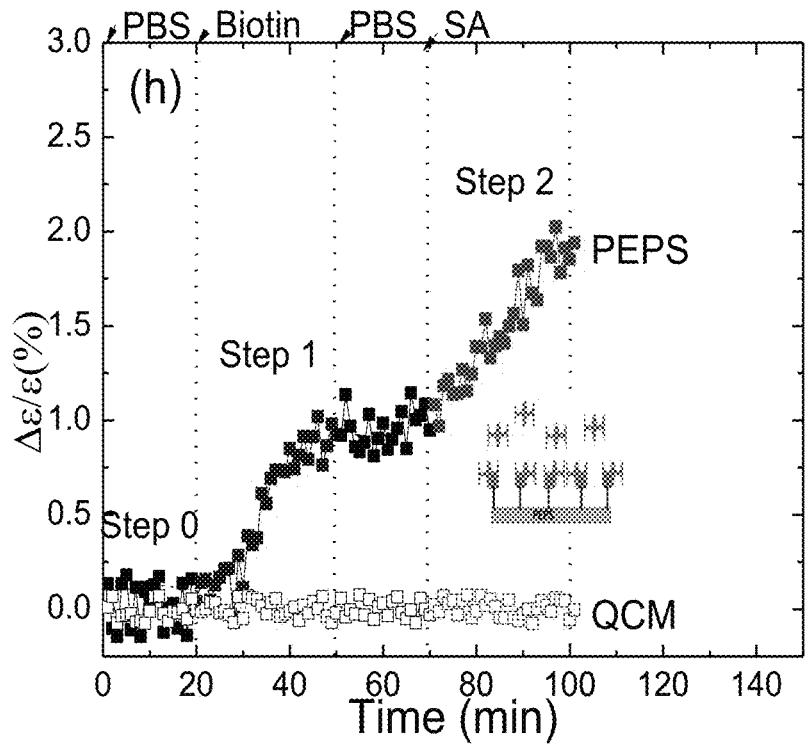
Figure 44C:
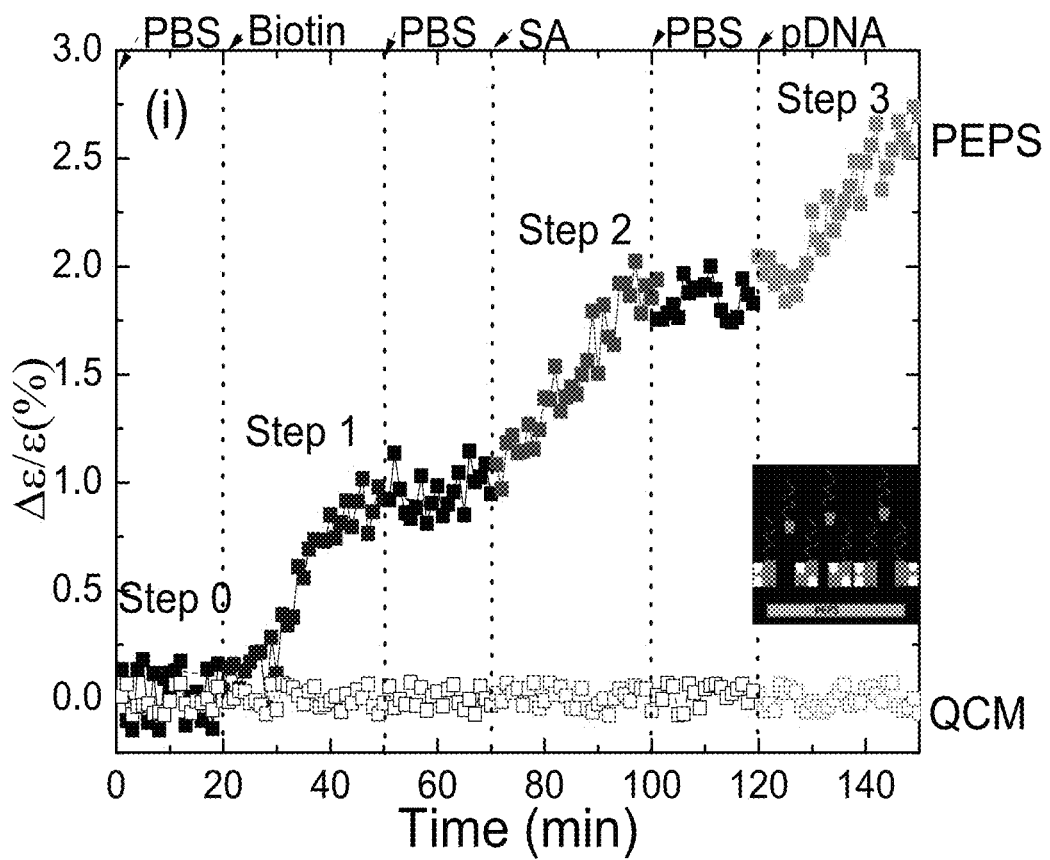

FIGS. 44A-44C show the relative dielectric constant, $-\Delta_{\varepsilon/\varepsilon}$ versus time of the sensor during the same immobilization steps as shown in FIGS. 42A-42C.

Figure 45:
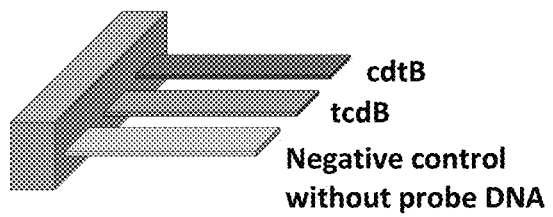

FIG. 45 is a schematic representation of a piezoelectric plate sensor array for detecting Clostridium difficile in a sample. The tcdB and cdtB represent PEPS functionalized with probes binding to toxin genes tcdB and cdtB of Clostridium difficile, respectively.

Figure 46:
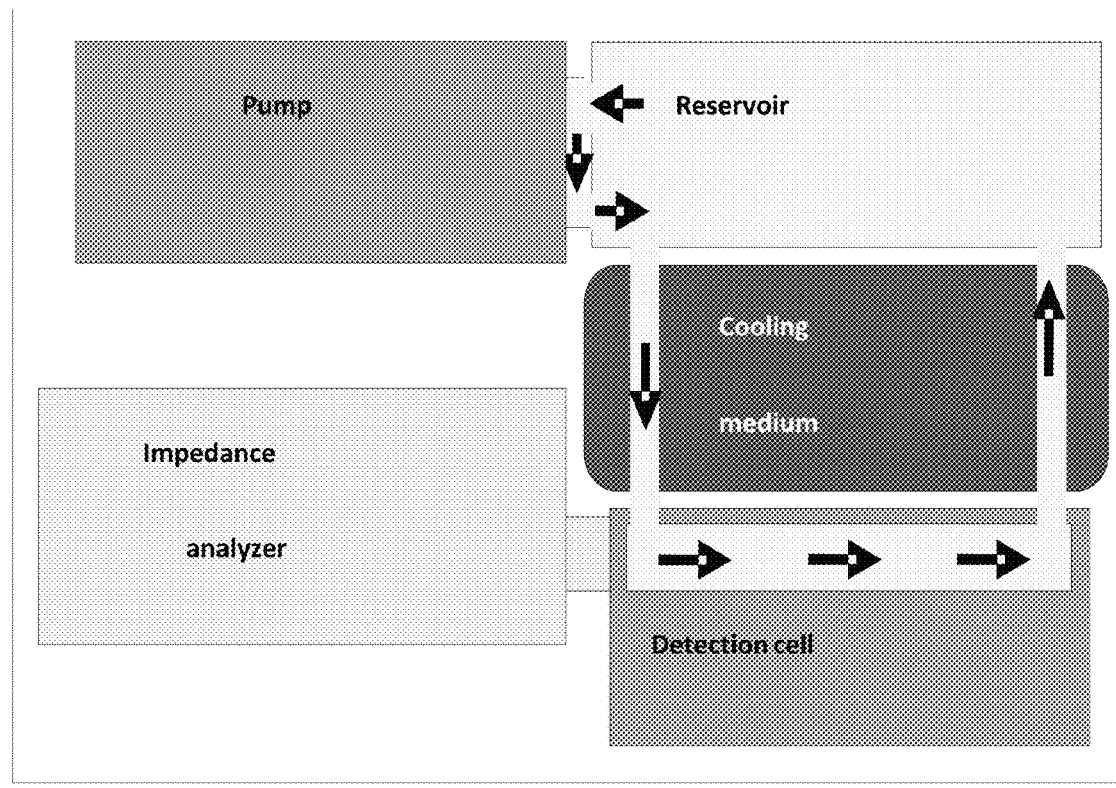

FIG. 46 is a schematic of the continuous flow detecting system including a high-temperature reservoir where viruses and bacteria are lysed, viral/bacterial DNA is released and denatured, a fast cooling module where the sample temperature is lowered while the DNA remains denatured, and a detection cell where the piezoelectric plate sensor of the present invention is located for in situ detection of the target viral/bacterial DNA directly from patient serum, urine, or stool samples without the need for DNA isolation or amplification.

Figure 47:
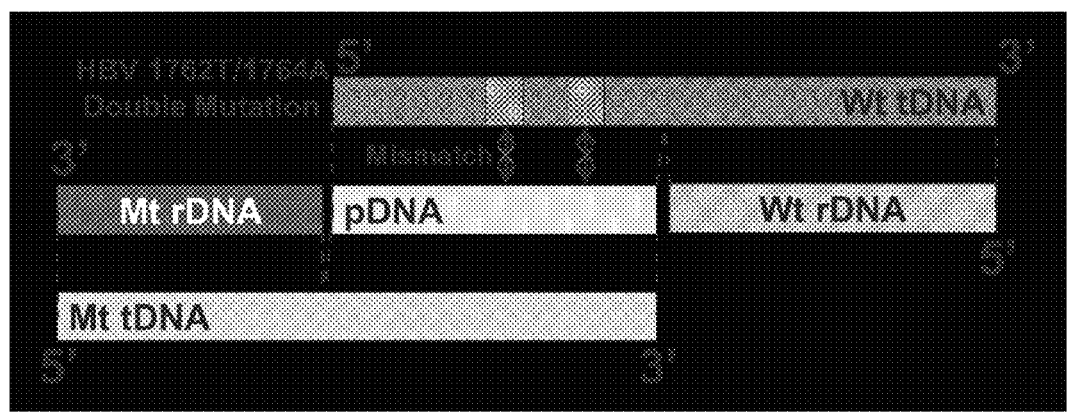

FIG. 47 is a schematic representation of the relationship between probe DNA (pDNA), mutant (MT) target DNA (tDNA), wild type (WT) tDNA, MT reporter DNA (MT rDNA), and WT rDNA (WT rDMA) for the hepatitis B viral (HBV) 1762/1764 double mutation.

Figure 48A:
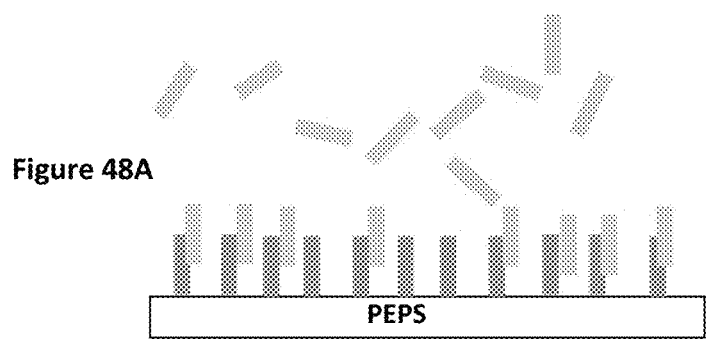

FIG. 48A is a schematic representation of MT tDNA binding to a probe on the surface of a PEPS.

Figure 48B:
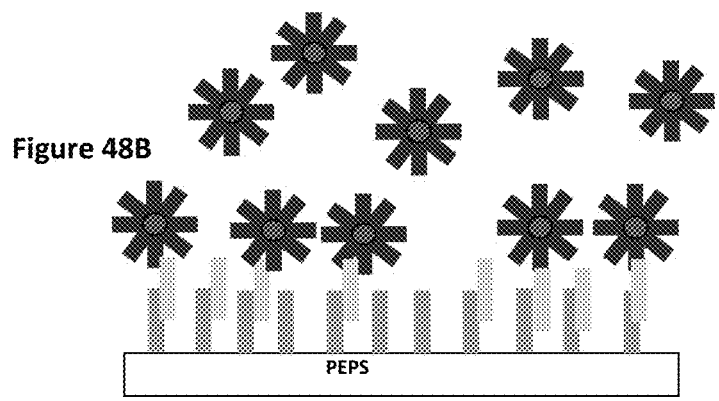

FIG. 48B is a schematic representation of an MT tDNA specific fluorescent reporter microsphere (MT FRM) that binds to the MT tDNA already bound on the probe on the surface of a PEPS.

Figure 48C:
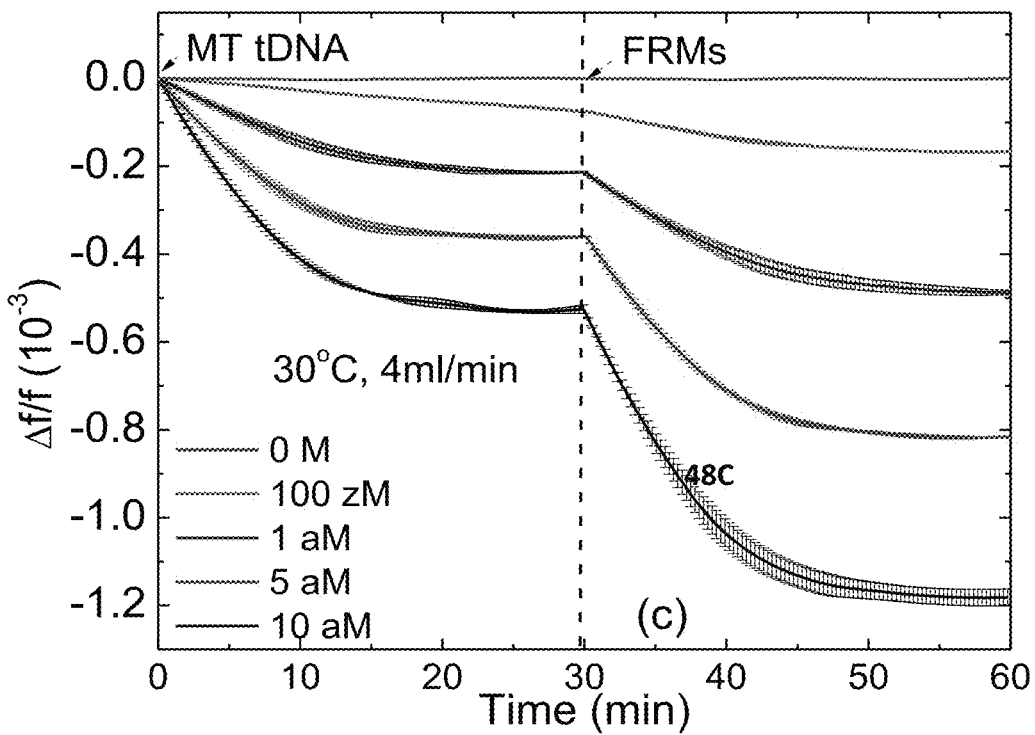

FIG. 48C is a plot showing $\Delta f/f$ versus time of MT tDNA detection, including binding of the MT FRMs to the MT tDNA on the PEPS surface.

Figure 49:
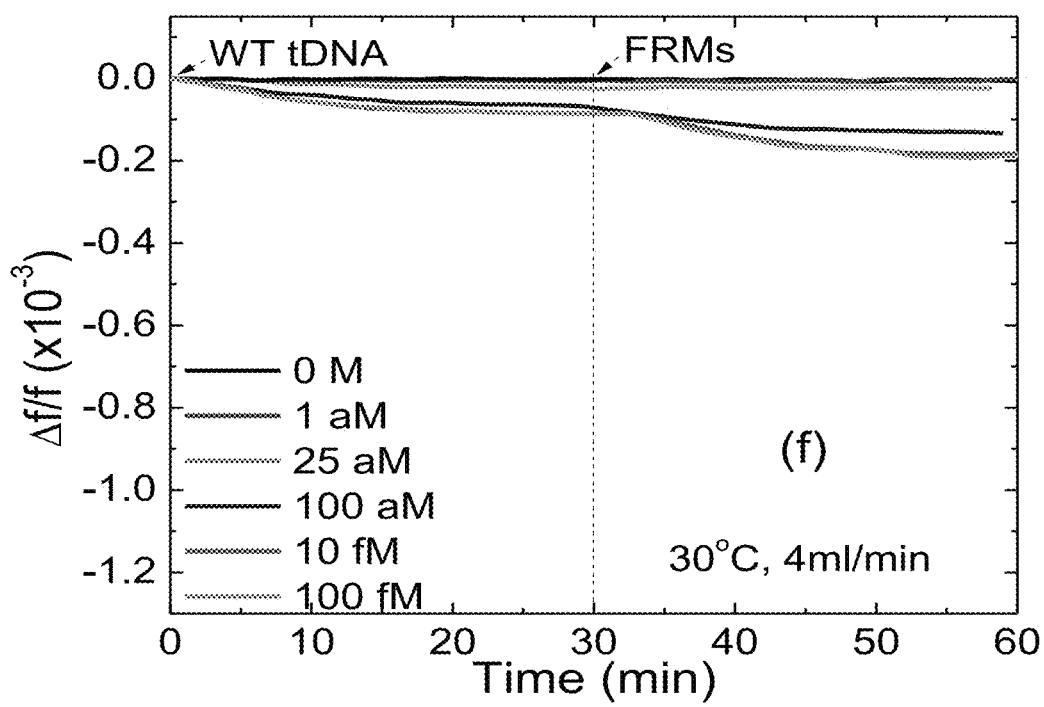

FIG. 49 is a plot showing $\Delta f/f$ versus time of WT tDNA detection, including binding of the WT FRMs to the WT tDNA on the PEPS surface.

Figure 50:
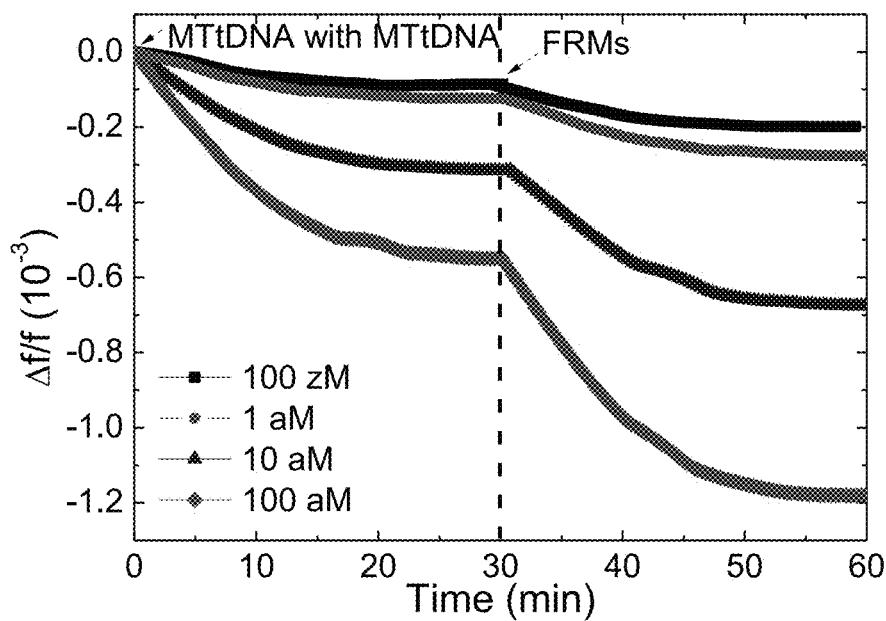

FIG. 50 is plot showing the relative resonance frequency shift, $\Delta f/f$ versus time of a PEPS detecting MT tDNA in a mixture with 250 times more WT tDNA than the MT tDNA at various MT tDNA concentrations followed by addition of both MT FRMs and WT FRMs at a concentration of $10^5$ FRMs/ml in PBS. The detection was carried out at 30° C. and at a flow rate of 4 ml/min.

Figure 51:
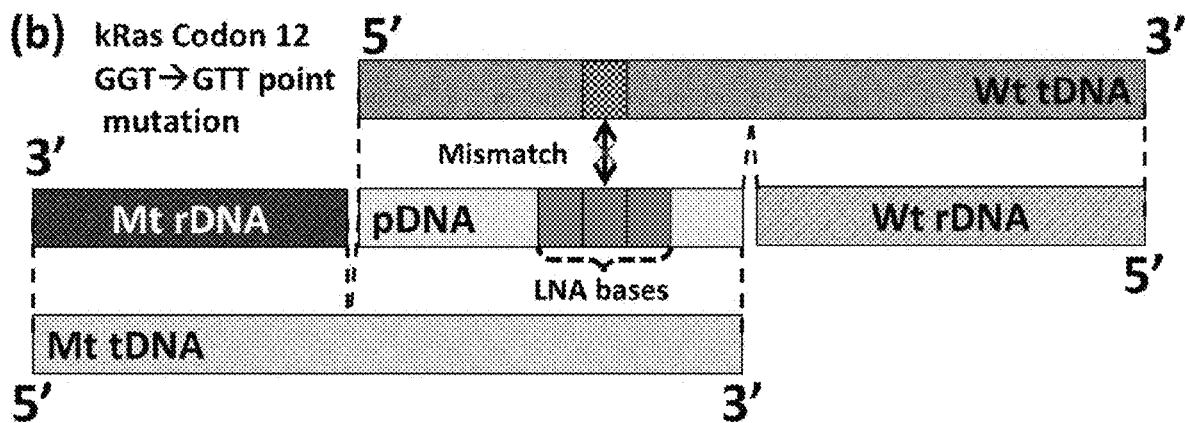

FIG. 51 is a plot representing the number of MT FRMs (circles) and that of MT FRMs (squares) versus $-\Delta f/f$ at t=30 min obtained from PEPS tDNA detection.

Figure 52:
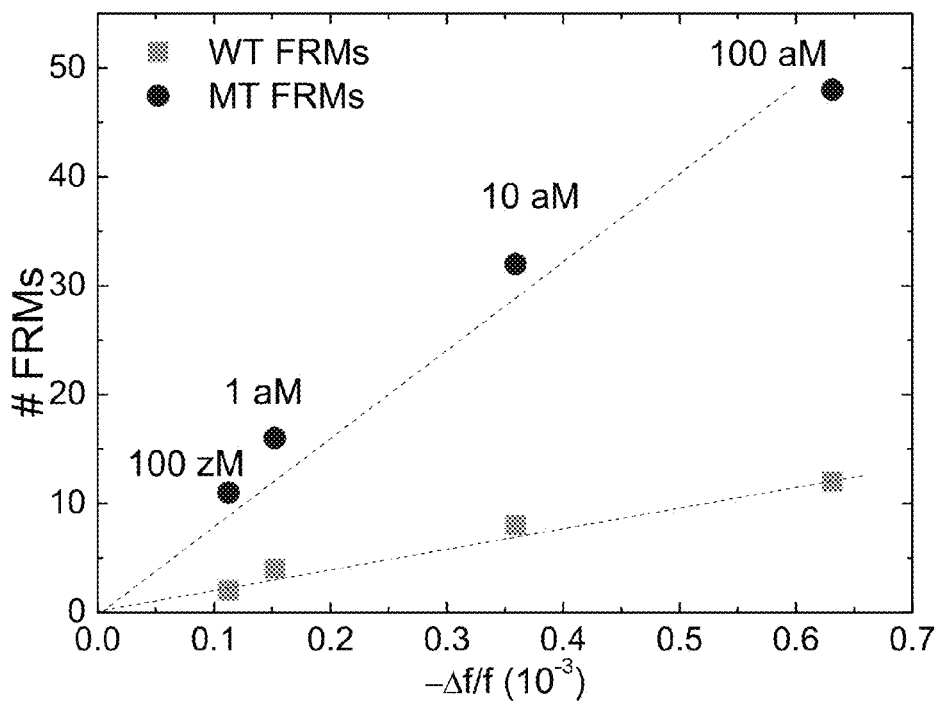

FIG. 52 is a schematic representation of the relationship between probe DNA (pDNA), mutant (MT) target DNA (tDNA), wild type (WT) tDNA, MT reporter DNA (MT rDNA), and WT rDNA (WT rDMA) for an kRas codon 12 point mutation.

Figure 53:
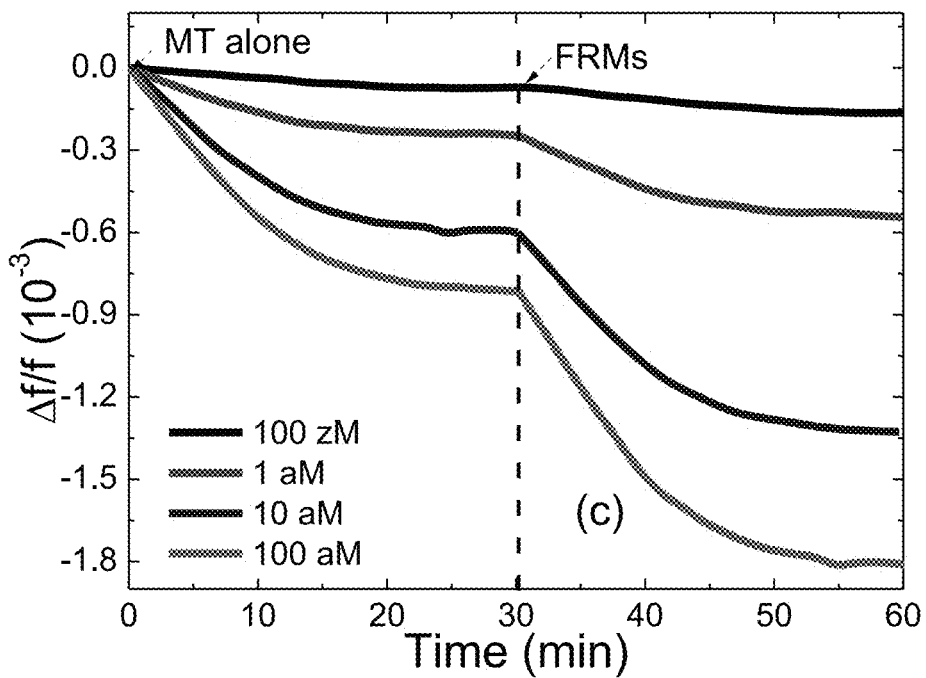

FIG. 53 is a plot showing $\Delta f/f$ versus time of MT tDNA detection, including binding of the MT FRMs to the MT tDNA on the PEPS surface.

Figure 54:
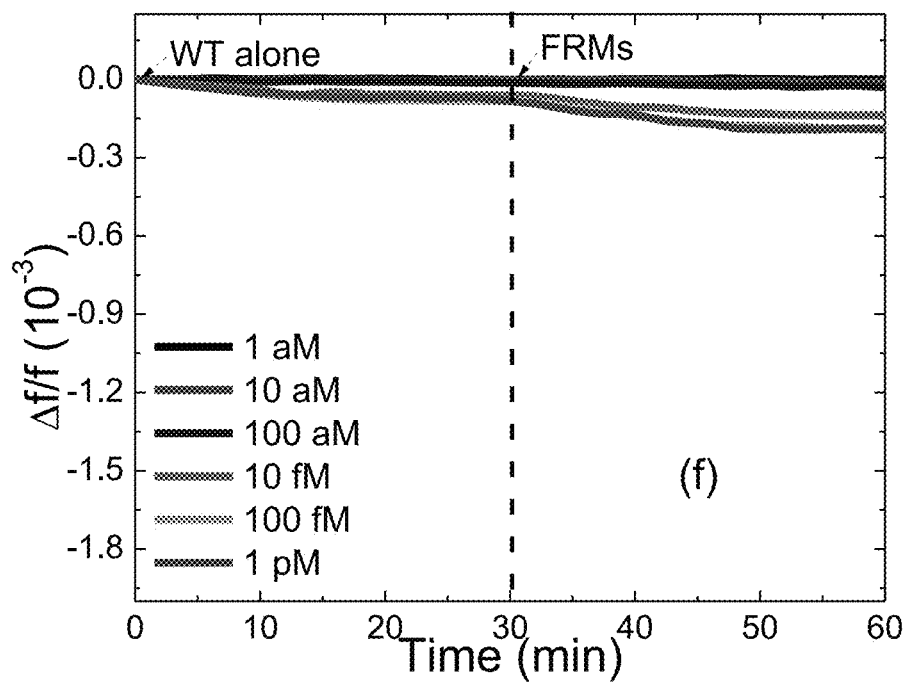

FIG. 54 is a plot showing $\Delta f/f$ versus time of WT tDNA detection, including binding of the WT FRMs to the WT tDNA on the PEPS surface.

Figure 55:
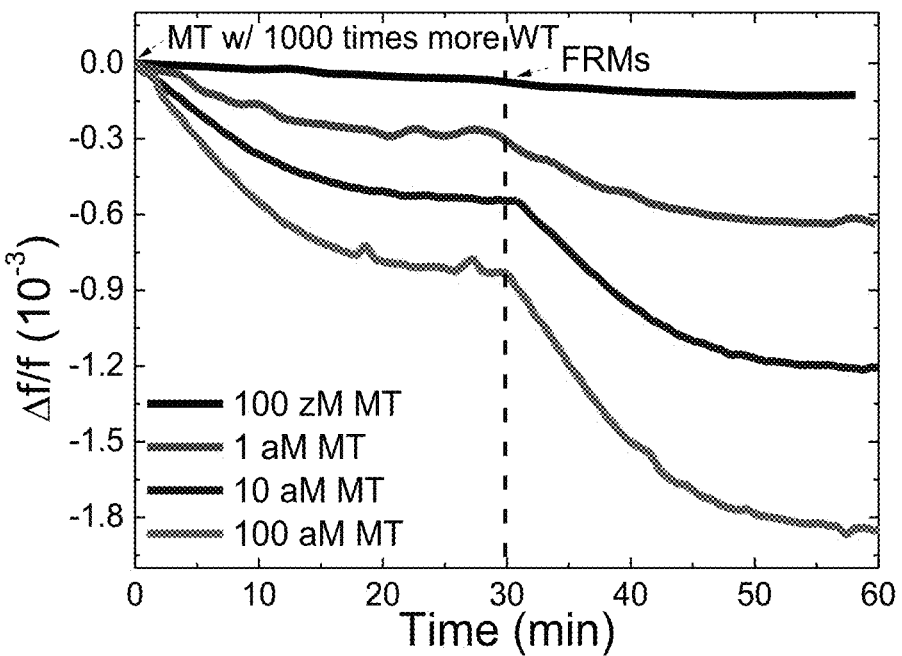

FIG. 55 is a plot representing relative resonance frequency shift, MN versus time of a PEPS detection of MT tDNA in a mixture with 200 times more WT tDNA at various MT tDNA concentrations followed by addition of both MT FRMs and WT FRMs at a concentration of $10^5$ FRMs/ml in PBS. The detection was carried out at 30° C. and at a flow rate of 4 ml/min.

Figure 56:
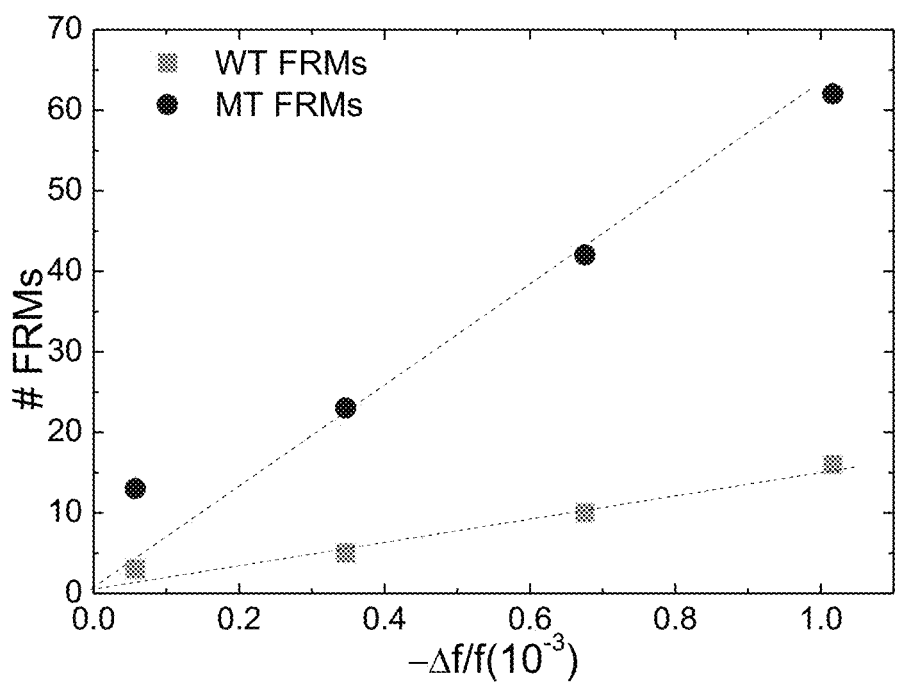

FIG. 56 is a plot representing the number of MT FRMs (circles) and that of MT FRMs (squares) versus $-\Delta f/f$ at t=30 min detected by PEPS tDNA detection.

Figure 57:
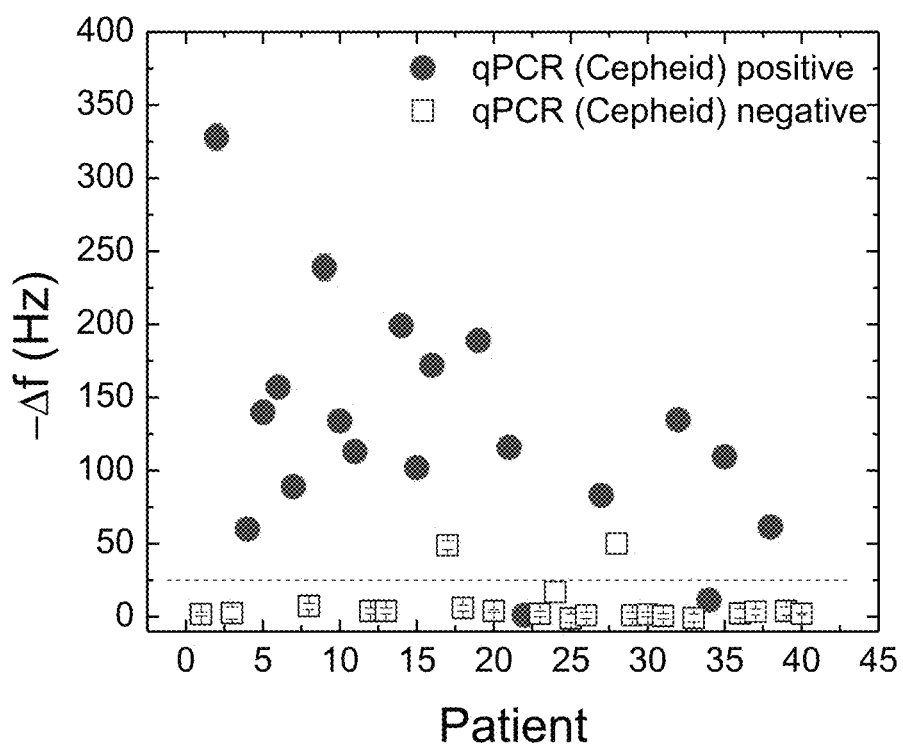

FIG. 57 shows the average detection $-\Delta f$ at 25-30 minutes of *Clostridium difficile* detection in 40 stool samples. Red circles indicate qPCR positive and open blue squares indicate qPCR negative.

Figure 58A:
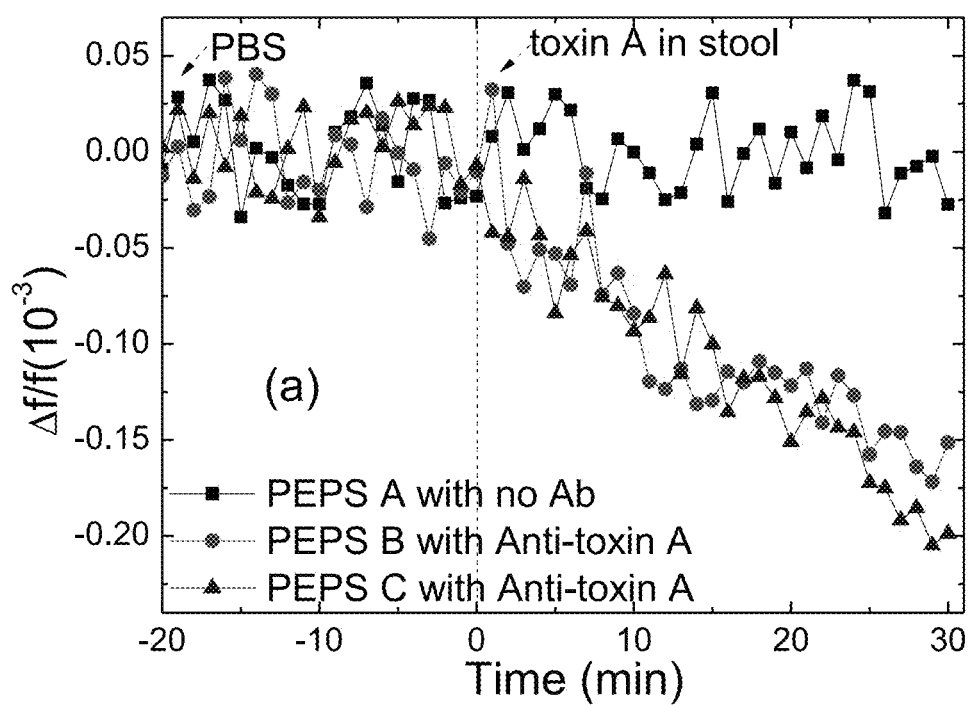

FIG. 58A shows the $\Delta f/f$ versus time of detection of spiked toxin A in stool at 25 pg/ml.

Figure 58B:
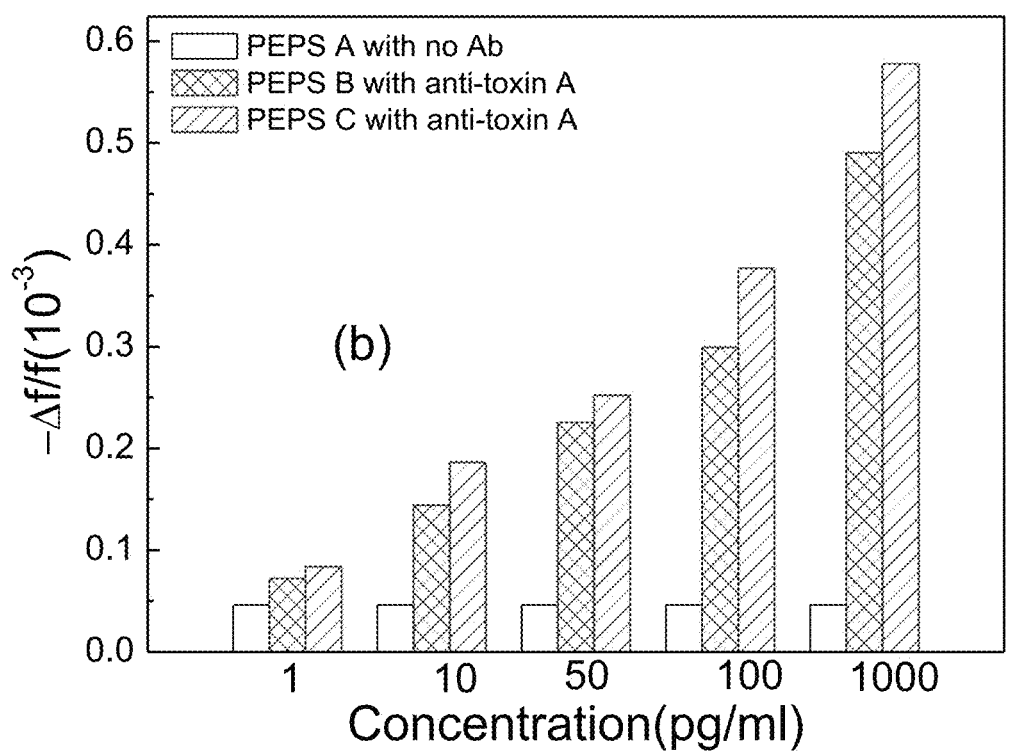

FIG. 58B shows the average $-\Delta f/f$ at 25-30 min of spiked toxin A detection in stool using an array of three PEPSs: PEP A as control, PEPS B and PEPS C both being functionalized with anti-toxin A to detect toxin A.

Figure 59:
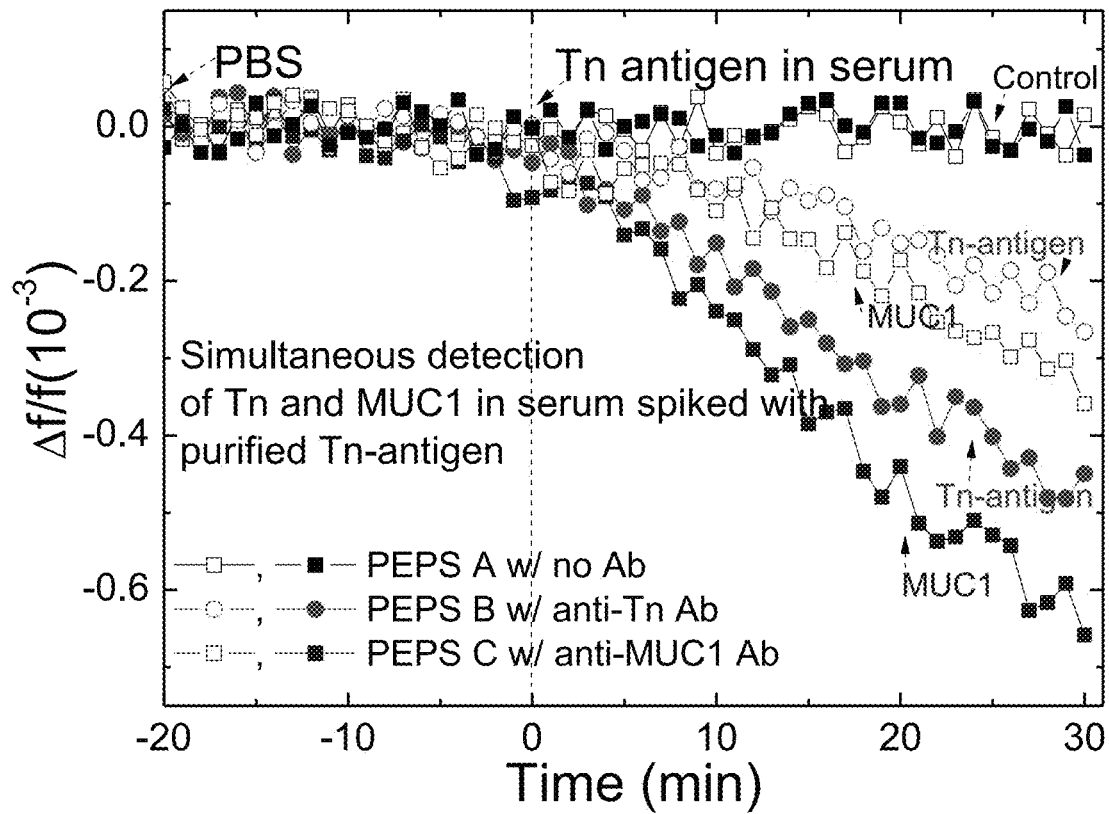

FIG. 59 shows the $\Delta f/f$ versus time of detection of spiked purified Tn antigen in bovine serum at concentrations of 10 pg/ml (hollow symbols) and 100 pg/ml (solid symbols) using an array of three PEPS: PEP A as control, PEPS B functionalized with anti-Tn antibody to detect Tn, and PEPS C functionalized with anti-MUC1 antibody to detect MUC1.

Figure 60:
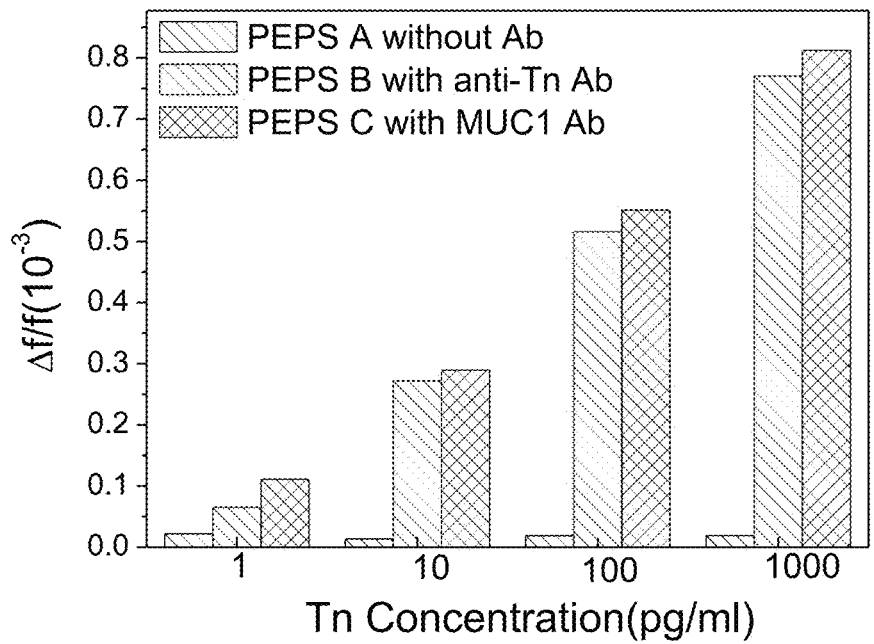

FIG. 60 shows $-\Delta f/f$ at 25-30 min for detecting spiked Tn antigen at different concentrations in serum using a 3-PEPS array: PEPS A with no antibody to serve as control, and PEPS B and C both functionalized with anti-Tn antibody to detect Tn at the same time.

Figure 61:
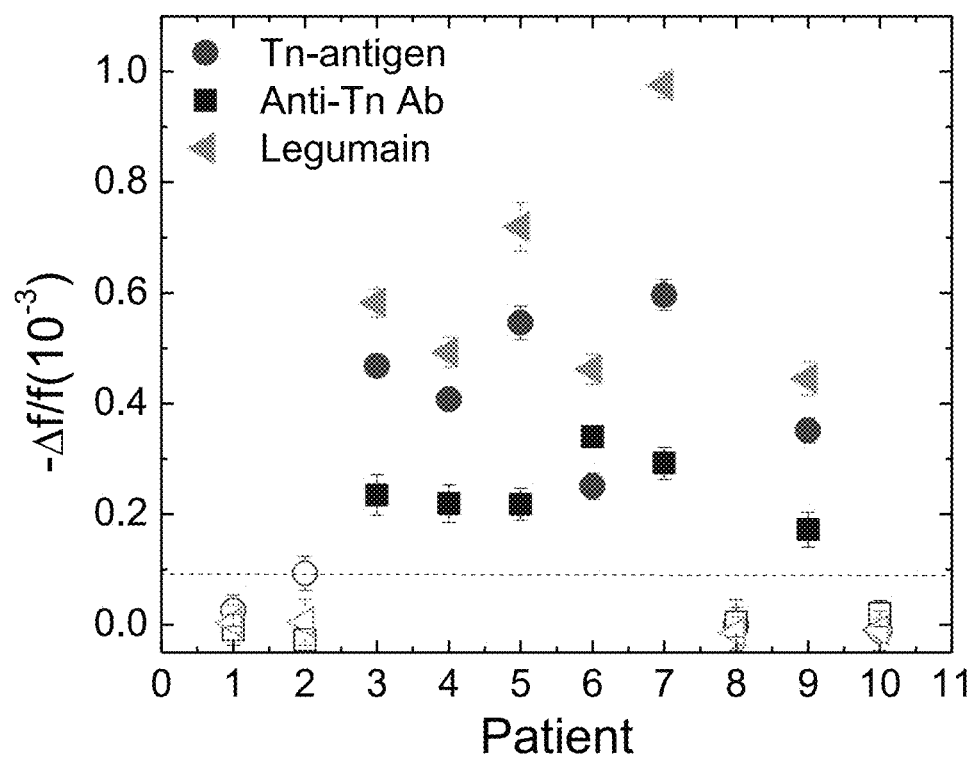

FIG. 61 shows the average $-\Delta f/f$ at t=25-30 minutes for simultaneous detection of Tn antigen, Anti-Tn antibody, and legumain in 10 blinded patient sera where the solid symbols indicate results from cancer patients and hollow symbols from non-cancer patients.

Figure 62:
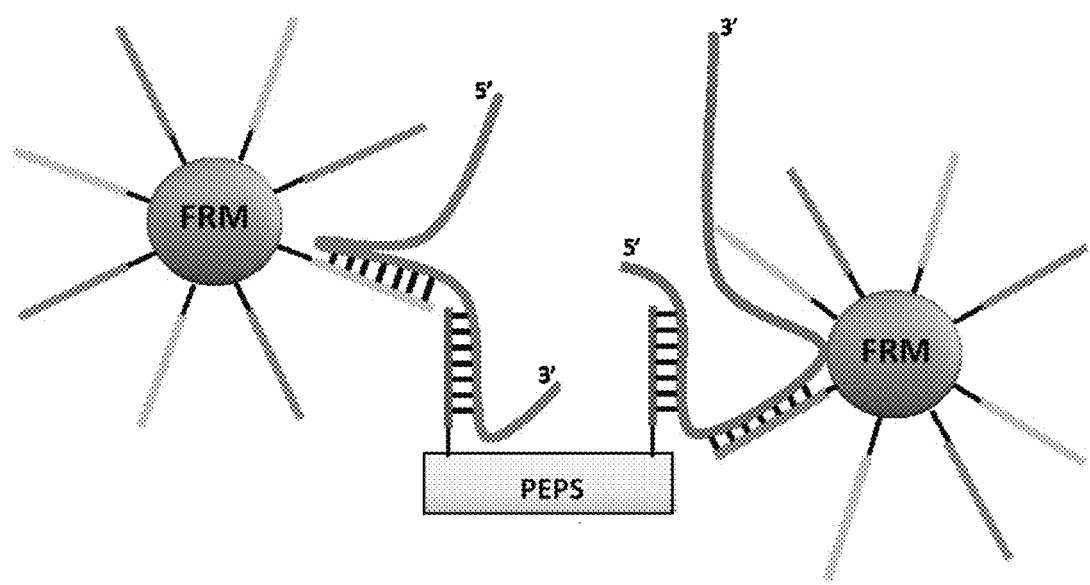

FIG. 62 is a schematic representation of the relationship between probe DNA (pDNA), the target hepatitis B (HB) viral DNA (tDNA, long curved lines), and the blue fluorescent microspheres (FRMs). The probe DNA is functionalized on the PEPS surface.

Figure 63A:
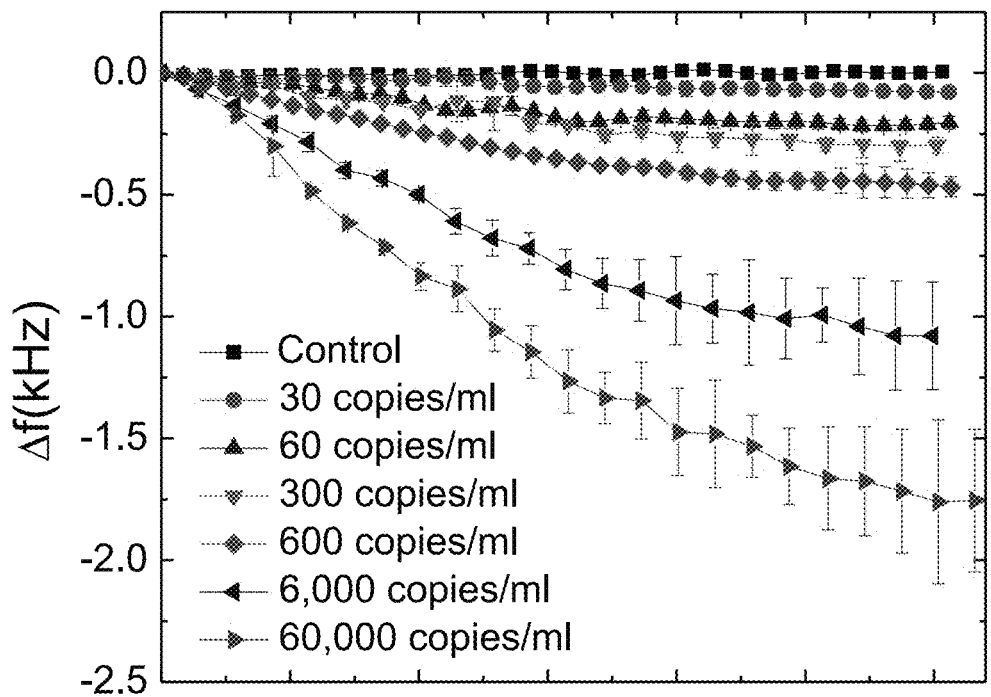

FIG. 63A shows $\Delta f$ versus time for detection of purified viral DNA spiked in simulated sera using the flow detection system of FIG. 46. The concentration of SDS used was 5%.

Figure 63B:
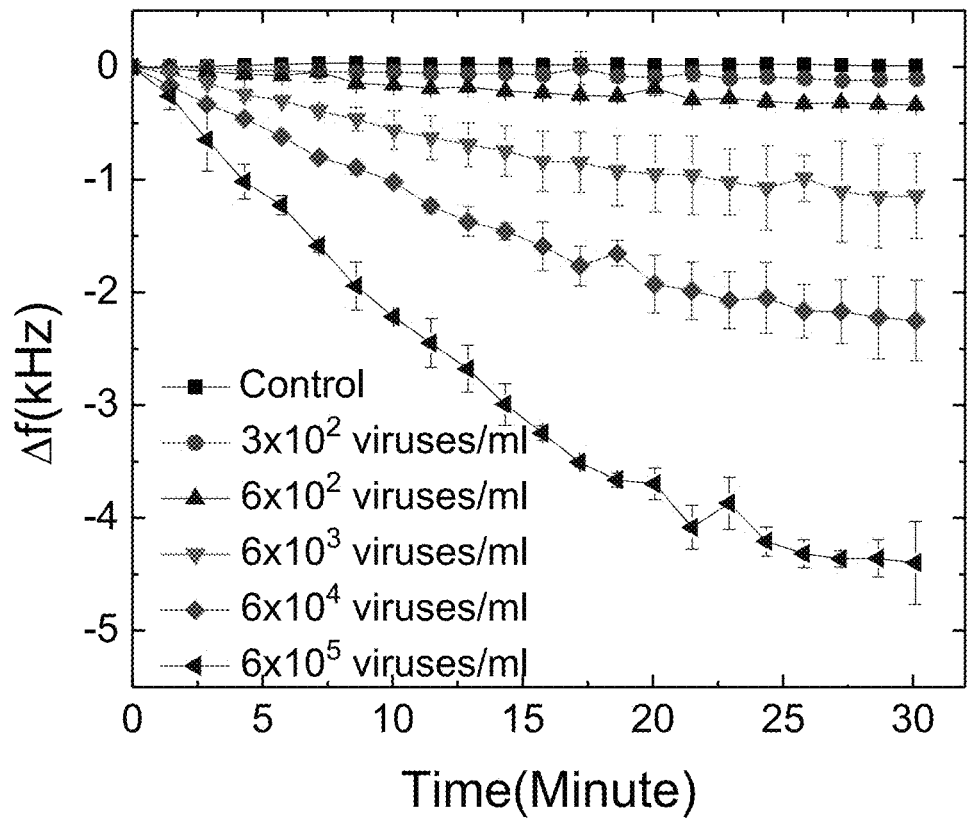

FIG. 63B shows $\Delta f$ versus time for detection of HB viral particles spiked in simulated sera using the flow detection system of FIG. 46. The concentration of SDS used was 10%.

Figure 64:
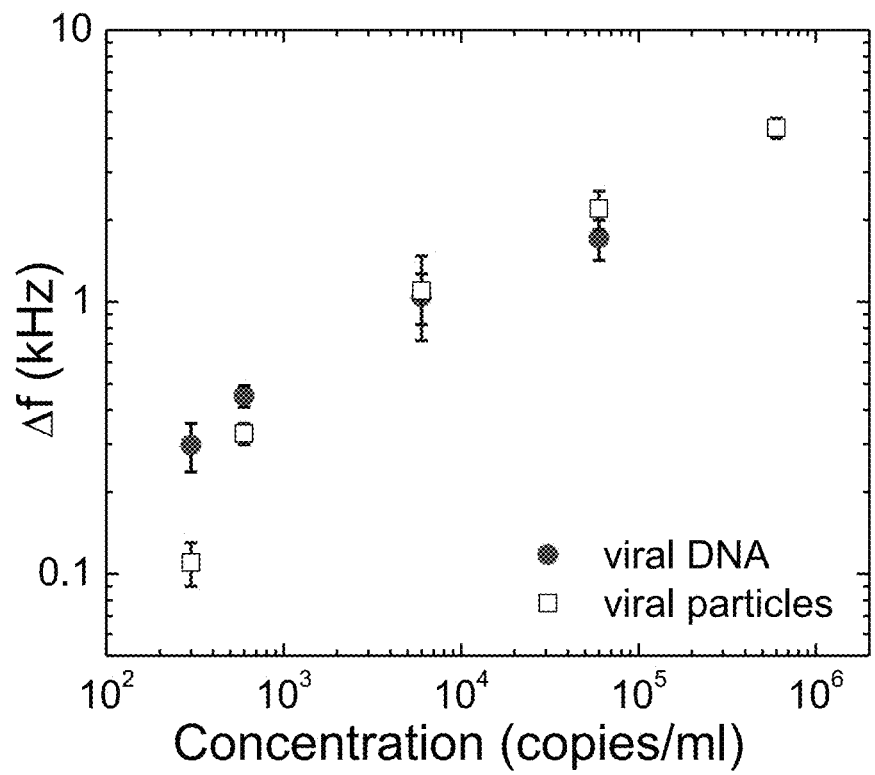

FIG. 64 is a plot comparing $-\Delta f$ 25-30 min between detection of purified viral DNA in simulated sera (circles) and detecting HB viral particles in sera (squares).

Figure 65:
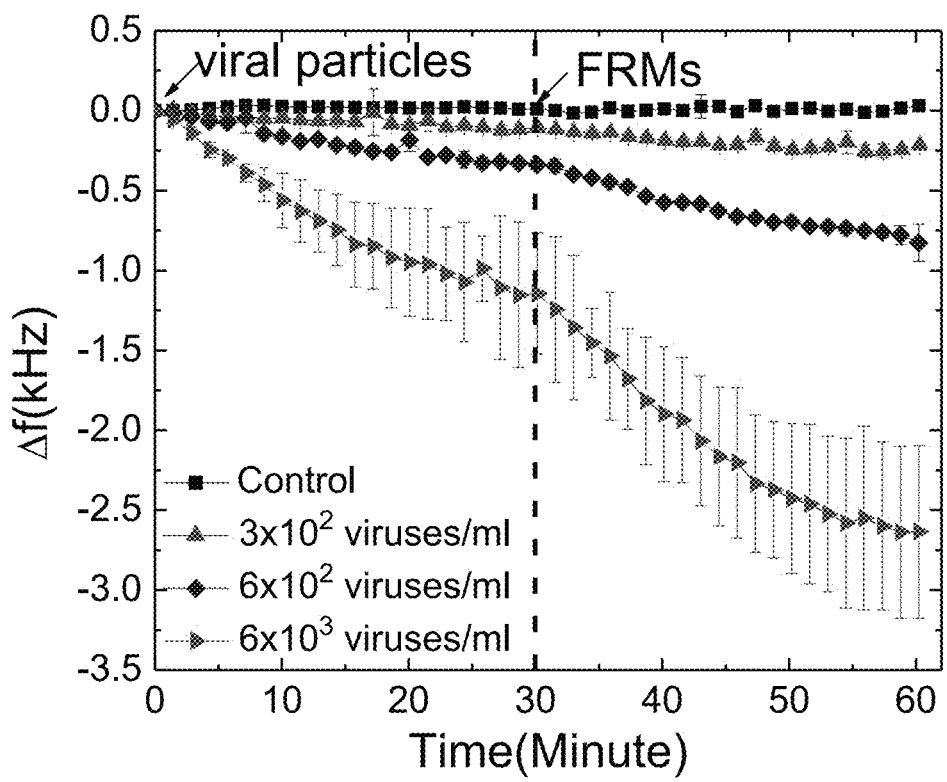

FIG. 65 is plot showing $\Delta f$ versus time for detecting HB viral particles followed by binding of FRMs.

Figures 66A, 66B, 66C:
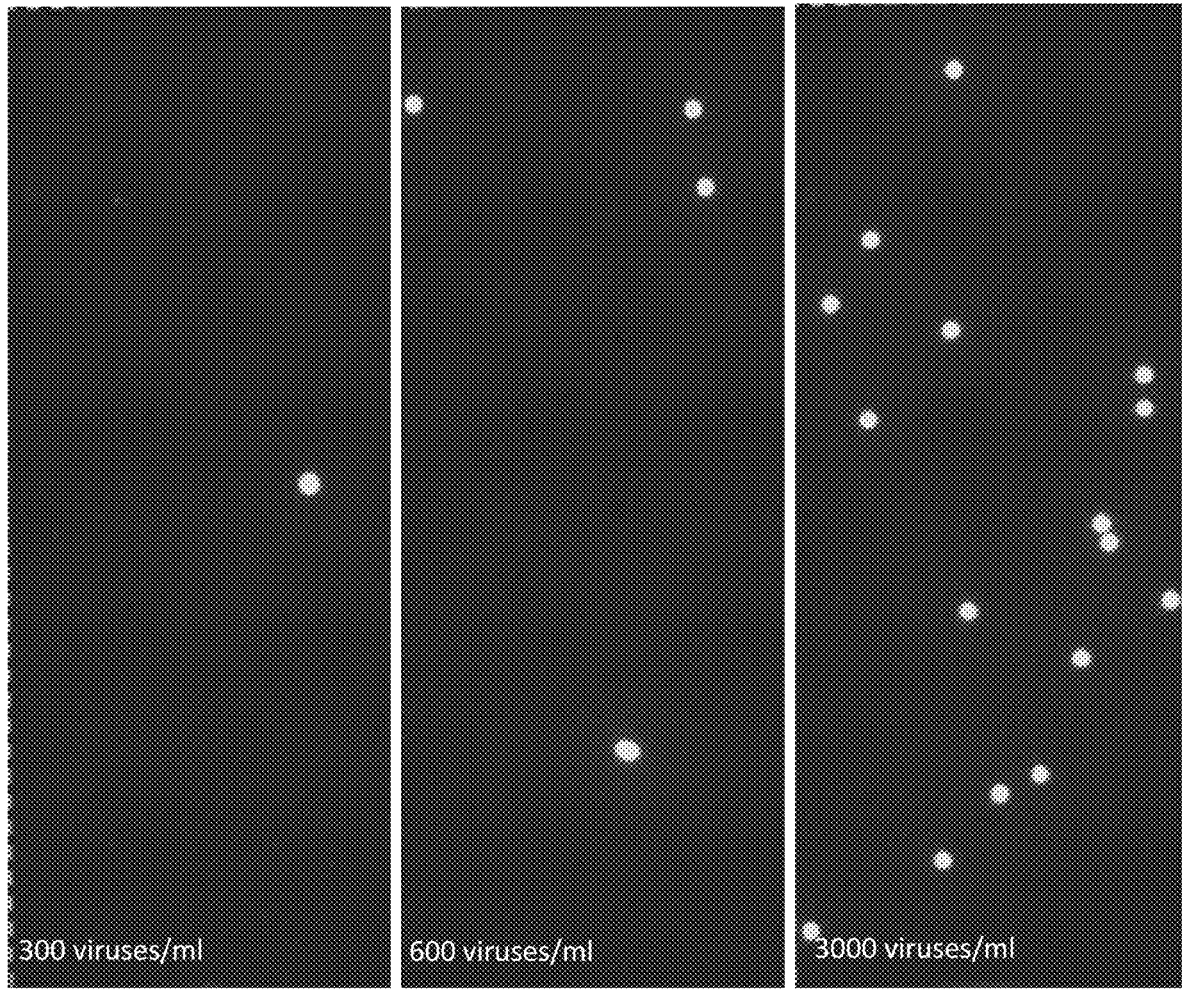

FIGS. 66A-66C show fluorescent images of the PEPS after HB viral particles detection at concentrations of 300, 600, and 3,000 viral particles/ml, respectively, followed by binding of FRMs.

Figure 67:
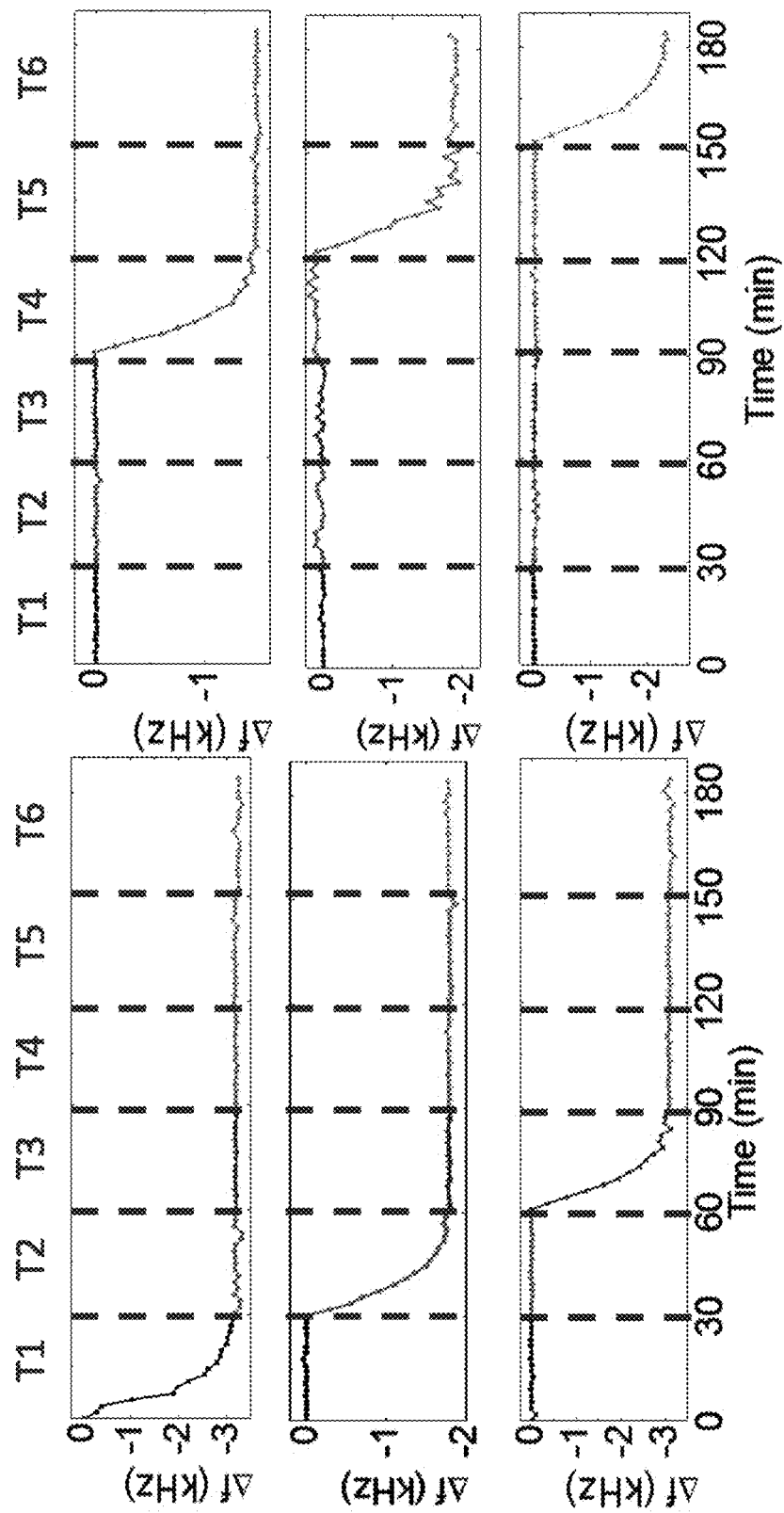

FIG. 67 shows $\Delta f$ versus time in detection of six different mutation sites in codon 12 of the Kras gene using an array of six PEPSs. Each PEPs in the array was functionalized with a probe to specifically target one of the six mutation sites.

DEFINITIONS

The term "sample" as used herein refers to a bodily fluid or other material taken from or derived from the body. In some embodiments, the sample comprises milk, blood, serum, plasma, ascites, cyst fluid, pleural fluid, peritoneal fluid, cerebral spinal fluid, tears, urine, stool, saliva, sputum, or combinations thereof.

The term "disease" as used herein refers to any physiological or psychological ailment, disorder, impairment or abnormality.

The term "biomarker" as used herein refers to a biomolecule in a sample that has a predictive value for human diseases. Biomarkers may be polypeptides, polynucleotides (DNA and RNA), metabolites, microbes. The presence, absence, reduction, and/or up-regulation of the biomarker may indicate a risk factor of a particular disease. Determination of the level or activity of a biomarker in the sample may comprise detection and quantitation of the biomarker itself or of a precursor, derivative or metabolite thereof. Biomarkers may also be associated with a specific state of a biological environment including but not limited to a phase of cellular cycle, or health and disease state.

The terms "diagnosis" as used herein refer to methods by which a person skilled in the art can estimate and even determine whether or not a subject is suffering from or susceptible to a given disease or condition. The skilled person often makes a diagnosis on the basis of one or more diagnostic indicators, such as for example a biomarker (e.g., a protein, an antibody), the amount (including presence or absence) of which is indicative of the presence, severity, or absence of the disease or condition.

The term "diagnosing" as used herein includes further the making a prognosis, which can provide for predicting a clinical outcome (with or without medical treatment), selecting an appropriate treatment (or whether treatment would be effective), or monitoring a current treatment and potentially changing the treatment, based on the measure of a substance of interest in a sample.

The term "treatment" as used herein refers to any herbal, homeopathic, immunotherapy, gene therapy, pharmaceutical, physical therapy, surgical or other medical intervention. Exemplary treatments may include administration of drugs or monoclonal antibodies, surgical removal of tissue, tissue or organ transplants, cancer immunotherapies, chemotherapy or vaccinations.

The term "subject" as used herein includes both human and animal subjects.

The term "complementary or matched" as used herein means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a nonspecific protein can be described as specifically binding to the antigen. Similarly, a nucleic acid probe can be described as specifically binding to a nucleic acid target if it forms a specific duplex with the target by base pairing interactions.

The term "detect" or "detection" as used herein refers to determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified.

The term "complementary sequences" as used herein refers to nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to nucleic acid probes disclosed herein, the nucleic acid probe can be 100% complementary with the target polynucleotide sequence. However, the nucleic acid probe need not necessarily be completely complementary to the target polynucleotide along the entire length of the target polynucleotide so long as the nucleic acid probe can bind with the target polynucleotide with specificity and capture it from the sample.

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into/onto a molecule, such as a polynucleotide.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using any of the well known methods in the art. An Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds. An Fv fragment is defined as a genetically engineered fragment containing the variable region of a light chain and the variable region of a heavy chain expressed as two chains.

Antibody may also be "single-chain antibody," which refers to a polypeptide comprising a VH domain and a VL domain in polypeptide linkage, generally liked via a spacer peptide, and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily, most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The term "nucleic acid probe" as used herein refers to a probe comprising a polynucleotide that contains a nucleic acid sequence that complementary to the sequence of a target nuclei acid molecule. The polynucleotide regions of probes may be composed of DNA, and/or RNA, and/or synthetic nucleotide analogs.

The terms "binding" or "bound" as used herein means to combine with, form a chemical bond with, or be taken up by. Binding or bound includes chemical bonding, as well as other methods of attaching to the substrate such as impregnation in a coating.

DETAILED DESCRIPTION OF THE PREFERRED EMBODIMENT(S)

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods. Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Figure 1:
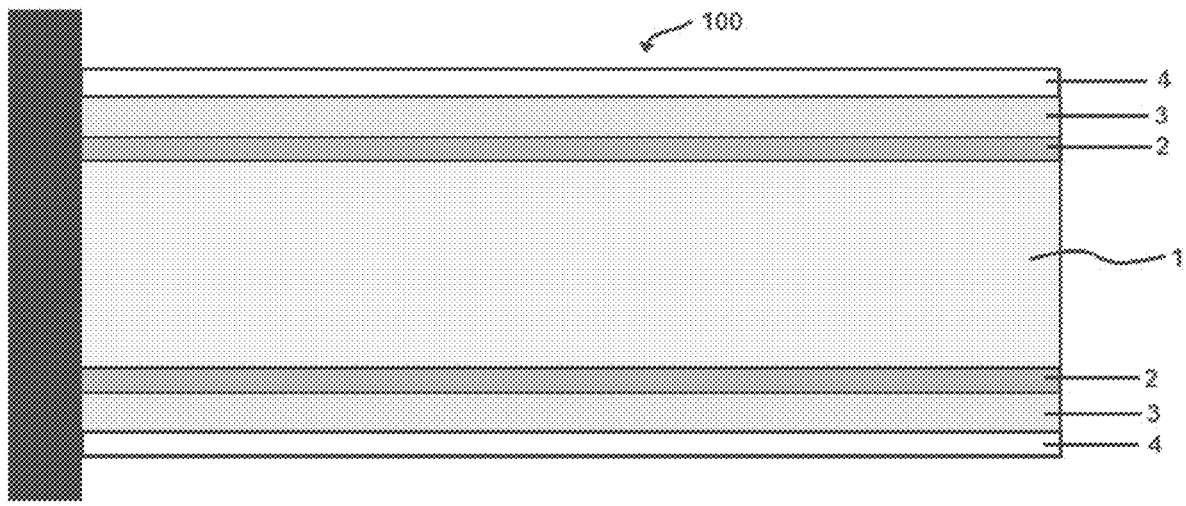
FIG. 1 shows a PEPS according to an embodiment of the present invention.

In one aspect, as shown in FIG. 1, the present invention provides a piezoelectric plate sensor (PEPS) 100, comprising a piezoelectric layer 1, two electrodes 2 positioned one on each side of the piezoelectric layer 1, an insulation layer 3 encompassing the piezoelectric layer 1 and two electrodes 2, and bound receptors 4 bound to the surface of the insulation layer 3 of the PEPS 100 for binding a biomolecule of interest.

Piezoelectric layer 1 is positioned between electrodes 2, functioning to enable electrical detection and actuation within the PEPS 100. Piezoelectric layer 1 may function as a driving element, vibrating element, sensing element, or a combination thereof. Applying an alternating current (AC) voltage across piezoelectric layer 1 as an input induces bending and vibration of piezoelectric layer 1, which in turn induces a change in an output voltage that provides readily detectable changes in the magnitude and phase of the output voltage. The resonance frequency of the PEPS 100 may be obtained, for example, by monitoring the maximum of the phase shift of the output voltage. This measurement may be accomplished all-electrically, i.e. using both electrical actuation and electrical sensing.

Piezoelectric layer 1 may be fabricated from any piezoelectric material, such as $(Na_{0.5}K_{0.5})_{0.945}Li_{0.055}Nb_{0.96}Sb_{0.04}O_3$ (hereinafter "Sb—NKNLN"), $Sb—(Na_{0.5}K_{0.5})NbO_3—LiTaO_3$ (hereinafter "Sb—NKNLT"), $Sr—(Na_{0.5}K_{0.5})NbO_3—LiTaO_3$ (Sr—NKNLN), $Sr—Na_{0.5}K_{0.5}NbO_3—LiTaO_3$ (Sr—NKNLT), $SbSr—(Na_{0.5}K_{0.5})NbO_3—LiTaO_3$ (SrSb—NKNLN), $SrSb—Na_{0.5}K_{0.5})NbO_3—LiTaO_3$ (SbSr—NKNLT), solid solutions with $(Bi_{0.5}K_{0.5})TiO_3$, $(Bi_{0.5}Na_{0.5})TiO_3$, $Ba(Zr_xTi_{1-x})O_3$, $BaTiO_3$ (hereinafter "BT"), $(Bi_{1/2}K_{1/2})TiO_3$ (hereinafter "BKT"), $(Bi_{1/2}Na_{1/2})TiO_3$ (hereinafter "BNT"), $Ba(Zr_xTi_{1-x})O_3$ (hereinafter "BZT"), $Bi(Zn_{1/2}Ti_{1/2})O_3$ (hereinafter "BiZT"), $(Na_xK_{1-x})NbO_3$ (hereinafter "NKN"), $BiScO_3—PbTiO_3$ $BaTiO_3—(Bi_{1/2}K_{1/2})TiO_3$ (hereinafter "BKBT"), $(B_{1/2}Na_{1/2})TiO_3—(Bi_{1/2}K_{1/2})TiO_3$ (hereinafter "BNKT"), $(Bi_{1/2}Na_{1/2})TiO_3—BaTiO_3$ (hereinafter "BNBT"), $(Bi_{1/2}Na_{1/2})TiO_3—Ba(Zr_xTi_{1-x})O_3$ (hereinafter "BNBZT") and $(Bi_{1/2}Na_{1/2})TiO_3—BaTiO_3—(Bi_{1/2}K_{1/2})TiO_3$ (hereinafter "BNBK").

In some embodiments, the piezoelectric layer 1 is fabricated from highly piezoelectric lead magnesium niobate-lead titanate films (hereinafter "PMN-PT"), such as $(Pb(Mg_{1/3}Nb_{2/3})O_3)_{1-x}—(PbTiO_3)_x$ $(PMN_{1-x}—PT_x)$ films, where $0.3<x<0.4$, or $(Pb(Mg_{1/3}Nb_{2/3})O_3)_{0.65}—(PbTiO_3)_{0.35}$ $(PMN_{0.65}—PT_{0.35})$; sodium potassium niobate-lithium niobate solid solutions (NKN-LN); highly piezoelectric lead zirconate titanate (PZT) films; or high piezoelectric lead-free films.

In an exemplary embodiment, piezoelectric layer 1 may be fabricated from any highly piezoelectric material with a high $-d_{31}$ coefficient in the range of from about 20 pm/V to about 5000 pm/V, or from about 200 pm/V to about 5000 pm/V, or from about 500 pm/V to about 5000 pm/V, or from about 2000 pm/V to about 5000 pm/V. In another exemplary embodiment, the $-d_{31}$ coefficient may be greater than about 20 p m/V. Additionally, piezoelectric layer 1 may have a piezoelectric coefficient $d_{33}$ greater than about 40 pm/V.

In one embodiment, piezoelectric layer 1 is made from highly piezoelectric lead magnesium niobate-lead titanate films, e.g. $(Pb(Mg_{173}Nb_{273})O_3)_{0\ 65}—(PbTiO_3)_{035}$ $(PMN_{0\ 65}—PT_{0\ 35})$ (PMN-PT), highly piezoelectric lead zirconate titanate (PZT) films or high piezoelectric lead-free films.

Piezoelectric layer 1 may be in any form. In one embodiment, piezoelectric layer 1 is fabricated from a free standing film for enhancing domain wall motion and piezoelectric performance. When the piezoelectric material is PMN-PT, piezoelectric layer 1 may be fabricated using a precursor-suspension method. Submicron crystalline PMN powder is first prepared by dispersing $Mg(OH)_2$—coated $Nb_2O_5$ particles in a lead acetate/ethylene glycol solution followed by calcination at about 800° C. The crystalline PMN powder is subsequently suspended in a lead titanate (PT) precursor solution containing lead acetate and titanium isopropoxide in ethylene glycol to form a PMN-PT precursor powder, which can be sintered at a temperature as low as about 900° C.

Piezoelectric layer 1 may have any structural configuration or dimensions. Thus, piezoelectric layer 1 may be rectangular, triangular, circular, elliptical, or any other geometric shape. Piezoelectric layer 1 may have a thickness of from about 0.5 μm to about 127 μm, or from about 0.5 μm to about 100 μm, or from about 0.5 μm to about 70 μm, or from about 0.5 μm to about 50 μm, or from about 1 μm to about 30 μm. Piezoelectric layer 1 may have a length of from about 1 μm to about 3 mm and a width of from about 1 μm to about 5 mm. Piezoelectric layer 1 may have a length of from about 10 μm to about 5 mm and a width of from about 0.5 μm to about 5 mm.

Electrodes 2 of the PEPS 100 may be manufactured from a material capable of conducting an electrical signal from the piezoelectric layer 1 to a device for detecting that signal. In some embodiments, electrodes 2 are constructed from a conductive material selected from Ag, Au, Cu, Pt, Ir, Al, Fe, Cr, Ni, C, In, C, Sn, Ti and an alloy of these metals. In one embodiment, one electrode 2 is constructed from Au/Cr or Pt/Ti and subsequently patterned in several regions. In some embodiments, electrode 2 may be constructed from $Pt/TiO_2$ on $SiO_2$ or Pt/Ti or Au/Cr on a metal substrate or non-piezoelectric layer. One or both of electrodes 2 may also be patterned.

Electrodes 2 may be a thin layer of conductive material with a thickness of less than about 150 nm, or less than about 130 nm, or less than about 110 nm, or less than about 100 nm, or less than about 90 nm, or less than about 80 nm.

Figure 2:
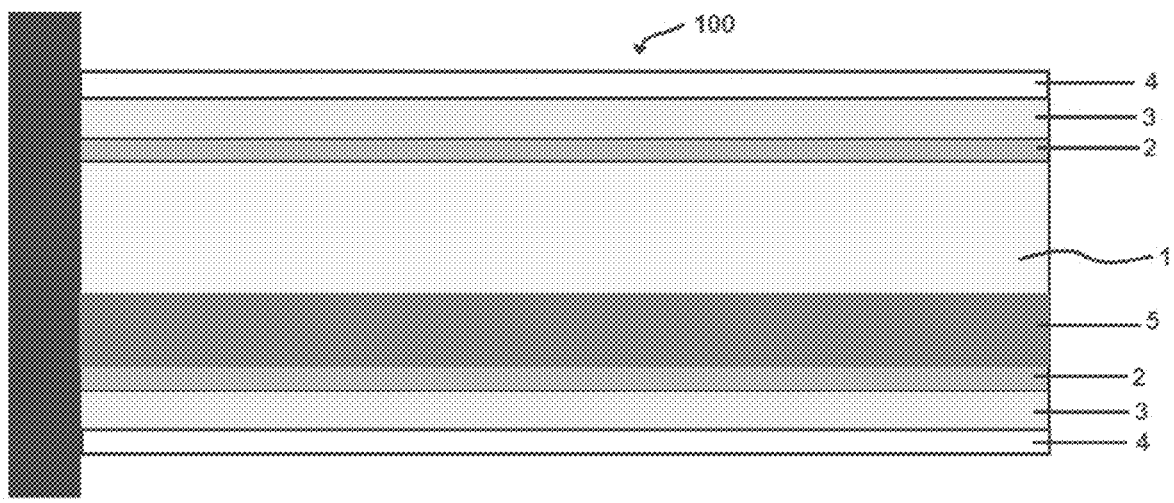
FIG. 2 shows a PEPS with a non-piezoelectric layer, according to an embodiment of the present invention.

In some embodiments, a non-piezoelectric layer 5 is included in the PEPS 100 as shown in FIG. 2. Non-piezoelectric layer 5 may be bonded to piezoelectric layer 1. Non-piezoelectric layer 5 may be made from any compatible material, including ceramic, polymeric, plastic, and/or metallic materials or any combination thereof. Non-piezoelectric layer 5 may be made from silicon dioxide ($SiO_2$), silicon nitride ($Si_3N_4$), a metal such as Cu, Sn, Ni, and Ti, or any combination thereof. Non-piezoelectric layer 5 may also have any structural configuration or dimension. Non-piezoelectric layer 5 may be rectangular, triangular, circular, elliptical, or have any other geometric shape. Non-piezoelectric layer 5 may have a length of from about 1 µm to about 5 mm, or from about 5 µm to about 5 mm, a width of from about 1 µm to about 5 mm, or from about 5 µm to about 5 mm, and a thickness of from about 0.05 µm to about 100 µm, or from about 0.1 µm to about 80 µm, or from about 1 µm to about 60 µm.

PEPS 100 may have a wide variety of structural configurations. Piezoelectric layer 1 may be bonded to a non-piezoelectric layer 5 that is shorter, longer or equal in length, or width.

Insulation layer 3 of the PEPS 100 may be made from mercaptopropyltrimethoxysilane (MPS). The insulation layer 3 can electrically insulate the PEPS 100 when the sensor is used for detection in a salty biological fluid such as a serum. In some embodiments, electrodes 2 may be patterned slightly smaller than piezoelectric layer 1 to ensure complete insulation of the edges and corners of electrodes 2.

Insulation layer 3 may be produced using a procedure called the MPS-W9 method, which involves soaking piezoelectric layer 1 and electrodes 2 in a MPS solution in ethanol with a minor amount of water. The MPS solution has a pH at from about pH 8 to about pH 10, or from about pH 8.5 to about pH 9.5, or from about pH 8.7 to about pH 9.3. In one embodiment, the pH of the MPS solution is about pH 9. The desired pH of the MPS solution may be achieved by adding an appropriate amount of, for example, acetic acid or potassium hydroxide.

To prepare piezoelectric layer 1 and electrodes 2 for receiving insulation layer 3, piezoelectric layer 1 and electrodes 2 are soaked in 1:100 diluted piranha solutions (about 3 parts sulfuric acid and about one part 30% hydrogen peroxide solution) for about 1 minute, and rinsed in deionized water and ethanol. Piezoelectric layer 1 and electrodes 2 are then soaked in transition MPS solution having a concentration of about 0.01 mM MPS with about 1% deionized water in ethanol for 30 minutes followed by rinsing in deionized water and ethanol.

The MPS solution for coating piezoelectric layer 1 and electrodes 2 to produce insulation layer 3 has a concentration of MPS at from about 0.01 v/v % to about 0.5 v/v %, or from about 0.02 v/v % to about 0.4 v/v %, or from about 0.04 v/v % to about 0.3 v/v %, or from about 0.06 v/v % to about 0.2 v/v %, or from 0.08 v/v % to about 0.15 v/v %, or from 0.08 v/v % to about 0.13 v/v %.

The solvent for the MPS solution may be ethanol with a minor amount water. The water in the solvent may be present in an amount of from about 0.1 v/v % to about 1 v/v %, or from 0.2 v/v % to about 0.9 v/v %, or from about 0.3 v/v % to about 0.8 v/v %, or from about 0.4 v/v % to about 0.6 v/v %.

Piezoelectric layer 1 and electrodes 2 are immersed in the MPS solution for from about 8 to about 150 hours, or from about 9 to about 120 hours, or from about 10 to about 100 hours, or from about 11 to about 80 hours, or from about 11 to about 50 hours, or from about 11 to about 20 hours, or about 30 hours. To minimize possible MPS cross-linking in the solution, piezoelectric layer 1 and electrodes 2 may be periodically taken out of the MPS solution and rinsed with deionized water and ethanol. This process may be repeated from about 1 to about 13 times, or from about 2 to about 10 times, or from about 2 to about 6 times, each with a fresh MPS solution.

In comparison with a coating method using an MPS solution with a lower pH (such as a pH from 4 to 5, as is used in the prior art MPS-5 method described in US 2011/0086368) and/or an ethanol solvent without water, the MPS-W9 method provides a higher coating rate in a range of from about 2 nm/hour to about 8 nm/hour. In addition, insulation layer 3 produced by the MPS-W9 method has a sufficiently smooth surface to define the detection surface area for quantitative detection. A smooth insulation layer 3 is important to the long term stability of the insulation layer 3 as well as providing a better controlled surface area for binding of a recognition molecule permitting more accurate quantitative detection. The MPS-W9 method also produces an insulation layer 3 with a higher density of silanol groups, which results in a denser MPS coating of greater than about 100 nm in thickness and excellent electrical insulation properties. Consequently, PEPS 100 has a stable resonance frequency over time and thus a stable base line resonance frequency which permits reuse of the sensor.

The denser MPS insulation layer 3 reduces current density of the PEPS 100 in a cyclic voltammetry test to less than about $10^{-7}$ $A/cm^2$. The electromechanical coupling coefficient $-k_{31}$ of the PEPS 100 is at least about 0.3, or at least about 0.31, or at least about 0.32, or at least about 0.33, or at least about 0.34, or at least about 0.5.

PEPS 100 has bound receptors 4 on at least one external surface of insulation layer 3. The recognition molecule, which can bind to a biomolecule of interest in a sample. The recognition molecule may be selected from an antibody, an antigen, a receptor, a ligand, or a nucleic acid, locked nucleic acid, peptide nucleic acid probe. More particularly, a bound antibody may bind to an antigen; a bound antigen may bind to an antibody; a bound receptor may bind to a ligand; a bound ligand may bind to a receptor; a bound nucleic acid (or locked nucleic acid, or peptide nucleic acid) probe may bind to a nucleic acid molecule comprising a sequence that is complementary to the sequence of the nucleic acid probe. The antibody may also bind to a protein, a metabolite, and a polynucleotide.

More than one recognition molecule can be bound to a particular sensor. Thus, for example, if two or more different biomarkers are known for diagnosing the same condition, recognition molecules for one or more of these different biomarkers can be bound to the same sensor to provide a cumulative measurement which could thereby further increase the sensitivity of the detection under certain circumstances. Alternatively, different recognition molecules for different biomarkers can be bound to different sensors to provide a sensor array that can detect multiple different biomarkers which can be for the same or different conditions.

Any means of binding a recognition molecule to the surface of the insulation layer 3 may be utilized. In some embodiments, recognition molecules are bound to insulation layer 3 using a bi-functional linker molecule.

The bi-functional linker molecule may be bound to insulation layer 3 using one of the two functional groups on the linker molecule. The recognition molecule may be bound to the bi-functional linker molecule using the other of the two functional groups of the linker molecule. An exemplary bi-functional linker molecule is sulfo-SMCC (sulfosuccinimidyl-4-(N-maleimidomethyl)cyclohexane-1-carboxylate), which through its maleimide functional group, forms a covalent link to the sulfhydro group of the MPS molecule in insulation layer 3. The linker molecule can also react with a protein such as an antibody or receptor, or an amine-activated nucleic acid probe that comprises an amine group via the sulfosuccinimidyl group of sulfo-SMCC. This reaction binds the antibody or nucleic acid probe on the surface of sensor 100.

In some other embodiments, the recognition molecule is bound to insulation layer 3 through biotin, such as Maleimide-PEG-Biotin (Pierce®). The biotin molecule is adhered to insulation layer 3 on one end, and bound to streptavidin on the other end.

The streptavidin may be further conjugated to an antibody that can bind to a biomolecule of interest in a sample. Alternatively, the streptavidin may have two biotin binding sites. One of the two biotin binding sites binds to the biotin on the surface of insulation layer 3. The other biotin binding site may be used to bind to a biotinylated antibody or a biotinylated nucleic acid probe.

The recognition molecule can be a nucleic acid probe for specifically detecting the genetic signature of one the DNA of a species of interest and can be used to provide a rapid, reliable test for the presence and concentration of a species of interest. Thus, any sequence fragment, especially a genomic DNA sequence fragment that is unique to the species of interest may be selected as a genetic signature of that species of interest. A nucleic acid probe complementary to one or more genetic signatures of the species of interest can be used for detecting these DNA fragments, thus indicating the presence of the species of interest.

Binding of a nucleic acid probe on insulation layer 3 may be accomplished, for example, by activating the nucleic acid probe by tagging the probe with an amine group, binding the bi-functional linker, Sulfo-SMCC, to insulation layer 3 by dipping it in a sulfo-SMCC solution for sufficient time (e.g., from about 10 to about 40 minutes) and reacting the amine group on the nucleic acid probe with the covalently bound Sulfo-SMCC on insulation layer 3 by dipping the sensor 100 in a solution of the activated nucleic acid robe for a sufficient time (e.g., from about 10 to about 40 minutes). The NHS (N-Hydroxysuccinimide) ester of the SMCC reacts with the amine group of the nucleic acid probe to form a covalent bond between the nucleic acid probe and the sulfo-SMCC linker. Optionally, functionalized sensor 100 may be coated with BSA or any other suitable material to block non-specific binding.

Also, an array of functionalized sensors 100 can be employed for detection. In such an array, each sensor 100 may be functionalized with a nucleic acid probe for specifically detecting the genetic signature of a different species of interest, and is then exposed to a sample. The species of interest, e.g. bacteria in the sample may be lysed (e.g., by sodium dodecyl sulfite, SDS) to release the genetic signature (DNA). The sample may be exposed to a temperature of about 90° C. to about 110° C. for denaturing the double strand DNA, then the temperature of the sample is lowered to from about 45° C. to about 70° C., preferably rapidly in less than 30 seconds, preferably less than 10 seconds. The array of piezoelectric plate sensors 100 may then be contacted with the sample for a time sufficient for the nucleic acid probe to bind to the genetic signature DNA fragments of the species of interest at the desired temperature in the range from about 45° C. to about 70° C. for specific binding to the target DNA or RNA.

The time for contacting the sample with the array of piezoelectric plate sensors 100 may be from about 10 minutes to about 30 minutes, or from about 15 minutes to about 25 minutes, or from about 18 minutes to about 22 minutes. The binding of the genetic signature DNA fragments on the surface of the piezoelectric plate sensors 100 causes a resonance frequency shift, which may be measured by a portable device such as an AIM 4170 impedance analyzer or an equivalent.

In one embodiment, the recognition molecule may be densely bound to the surface of PEPS 100. The recognition molecule may cover a major area of the surface of sensor 100. The functionalized sensor 100 may be further coated with fetal bovine serum albumin (BSA) or any other suitable material to block potential nonspecific binding of a protein or nucleic acid or other substances on the surface of sensor 100, in order to increase the detection specificity.

PEPS 100 may detect the presence of, or measure the concentration of a biomolecule in a sample. Sensor 100 is exposed to the sample for period from about 5 minutes to about 60 minutes, or from about 7 minutes to about 50 minutes, or from about 10 minutes to about 40 minutes, or from about 13 minutes to about 30 minutes, or about 15 minutes to about 25 minutes.

The resonance frequency shift caused by the binding of the biomolecule to the recognition molecules on the surface of the functionalized sensor 100 is measured to determine the presence and/or concentration of the biomolecule in the sample. The sensor 100 is capable of different modes, such as length extension mode, width extension mode, planar extension mode, or combinations thereof.

Two or more sensors 100 may be used in an array for simultaneously detecting plurality of different biomolecules in a sample.

The binding of the biomolecule to sensor 100 causes a change of effective mass and more importantly, a change in the effective spring constant of piezoelectric layer 1, which leads to a resonance frequency shift. By monitoring the resonance frequency shift biomolecules may be detect in a rapid, label-free, quantitative, direct, in situ manner.

In operation, an alternating voltage may be applied to one electrode 2 to drive piezoelectric layer 1 and the other electrode 2 may be used to detect the resonance frequency. Sensor 100 is capable of detecting shifts in resonance frequency by monitoring the $i^{th}$-mode flexural resonance frequency $f_i$, which is related to the effective spring constant, $K_e$, and effective mass, $M_e$, of the PEPS 100 as shown in Equation 1.

$$f_i = \frac{1}{2\pi}\sqrt{K_e/M_e} \quad \text{(Equation 1)}$$

The binding of the biomolecule of interest on the surface of the PEPS 100 changes the sensor mass and the sensor spring constant. The resonance frequency shift $\Delta f$, is expressed in Equation 2, $$\Delta f_i = f_i\left(-\frac{\Delta m}{2M_e} + \frac{\Delta k}{2K_e}\right) \quad \text{(Equation 2)}$$

where $\Delta m$ and $\Delta k$ denote the mass change and the effective spring constant. For a PMN-PT PEPS 100 having an 8 μm thickness and with a transverse electromechanical coupling coefficient, $-k_{31}$ of about 0.32, the contribution from the change in the effective spring constant to the resonance frequency shift was more than 1000 times larger than that from the change in the effective mass. This is in sharp contrast with piezoelectric sensors made of quartz or ZnO for which the resonance frequency shift due to binding of molecules is only a result of change in the effective mass. Thus, an 8 µm PMN-PT PEPS 100 with $-k_{31}$ of about 0.32 exhibits a detection relative resonance frequency shift, $-\Delta f/f$ more than 1000 times larger than could be achieved by a piezoelectric sensor made of, say, quartz or ZnO that cannot exhibit a molecular binding induced effective spring constant change. Here $\Delta f$ and f denote a sensor resonance frequency shift and resonance frequency of the PEPS 100, respectively.

This more than 1000 times enhancement in $-\Delta f/f$ in an 8 µm PMN-PT PEPS 100 with $-k_{31}$ of about 0.32 is attributed to the fact that binding of a biomolecule on the surface of the PEPS 100 causes changes to the elastic modulus of piezoelectric layer 1. The relative resonance frequency shift for the sensor 100, $-\Delta f/f$, is directly proportional to the binding-induced surface stress and inversely proportional to the sensor thickness. This indicates that under the same detection conditions, $\Delta f$ could be higher with a high-frequency resonance mode to provide a higher detection sensitivity. As non-flexural extension mode resonance occurs at a much higher frequency than flexural-mode resonance, detection using non-flexural resonance modes can potentially increase sensor sensitivity without size reduction. In addition, for a given f, $\Delta f$ may also be higher with a smaller thickness as $-\Delta f/f$ is inversely proportional to the thickness of PEPS 100. Finally, for a given f and PEPS thickness, the extent of the Young's modulus change is related to the transverse electromechanical coupling coefficient, $-k_{31}$, thus, $-\Delta f$ can also increase with an increasing $-k_{31}$.

Optionally, a positive or negative change in the Young's modulus of piezoelectric layer 1 may be induced by stress generated by the binding of the target molecules, which is preferably a substantial change in the Young's modulus of piezoelectric layer 1. The resonance frequency of piezoelectric layer 1 is proportional to the square root of its Young's modulus. The induced change in the Young's modulus may be up to about 10% and is preferably greater than about 1%, or from about 0.001% to about 10%, or from about 0.01% to about 5%, or from about 0.1% to about 4%.

The $\Delta f/f$ in the length extension mode (LEM) or width extension mode (WEM) due to the change in mass is normally about 0.001%, typical of piezoelectric sensors comprising quartz or zinc oxide that have a low piezoelectric coefficient of $-d_{31}<10$ pm/V and are incapable of changing their Young's modulus upon target molecule binding to their surface. In contrast, the $\Delta f/f$ of a thin PEPS 100 such as an 8 µm thick PMN-PT with a $-d_{31}$ piezoelectric coefficient much larger than 10 pm/V or 100 pm/V or 150 pm/V, which corresponding to a $-k_{31}$ much larger than 0.1, or 0.2, or 0.3, that is capable of substantial Young's modulus change upon binding of target molecules to its surface could be as high as 0.1%, or 1%, or 5% depending on the transverse electromechanical coupling coefficient, $-k_{31}$ of the piezoelectric layer 1, the thickness of the piezoelectric layer 1, and also the quality of the insulation layer 1 when the detection is conducted in a salty biological fluid.

The detection sensitivity, as defined by the relative resonance frequency shift, $\Delta f/f$, is governed by piezoelectric properties of piezoelectric layer 1, the thickness of piezoelectric layer 1, and the quality of the electrical insulation. The sensitivity may be improved by increasing the $-k_{31}$ of piezoelectric layer 1, by reducing the thickness of the piezoelectric layer 1, and by improving the insulation quality of the electrical insulation layer.

The $-k_{31}$ of the piezoelectric layer 1 can be increased by improving the sintering of the piezoelectric layer and by increasing the grain size of the piezoelectric layer 1. Preferably, the grain size of the piezoelectric layer 1 is larger than 6 µm, or larger than 5 µm, or larger than 4 µm, or larger than 3 µm, or larger than 2 µm. Grain boundaries are inhibitors for Young's modulus change in morphotropic phase boundary (MPB) piezoelectrics such as PMN-PT. Large grains reduce the presence of grain boundaries and enhances polarization switching and the Young's modulus change.

The quality of the electrical insulation may be improved by using the MPS-W9 method. The MPS-W9 method allows condensation of the silanol groups of the MPS to occur more effectively, which leads to a denser coating with >100 nm in thickness. The improved insulation layer 3 reduces the maximum current density of sensor 100 in a cyclic voltammetry test to less than about $10^{-7}$ A/cm$^2$, or less than about $5\times10^{-7}$ A/cm$^2$, or less than about $10^{-8}$ A/cm$^2$, which is more than two orders of magnitude lower than is achievable by an MPS coating produced by the prior art MPS-5 method. Consequently, the noise level of sensor 100 is reduced, which enhances the sensitivity of biomolecule detection by improving the signal-to-noise ratio.

Sensor 100 may be capable of electric actuation and electrical detection, be chemically inert, and thermally stable. Sensor 100 may have a high detection sensitivity of about $1\times10^{-11}$ g/Hz or better, or about $1\times10^{-13}$ g/Hz or better, or about $1\times10^{-16}$ g/Hz or better, or about $1\times10^{-17}$ g/Hz or better, or about $1\times10^{-18}$ g/Hz or better, or about $1\times10^{-19}$ g/Hz, or about $1\times10^{-20}$ g/Hz, or better. Sensor 100 is capable of detecting low levels of circulating proteins in human blood or serum and detecting a single cell in a liquid sample. Sensor 100 may be used in air, liquid or solid samples.

Sensor 100 may be used to determine the concentration of a substance in a sample, in addition to being able to detect the presence of such substance. The resonance frequency shift can be mathematically related to the concentration of the substance in the sample by calibration of sensor 100 with the substance of interest.

In some embodiments, a secondary antibody may be used to enhance the sensitivity of biomolecule detection. The secondary antibody also binds to the same biomolecule of interest in the sample, though on a separate, non-competing epitope of the biomolecule. Thus, the secondary antibody is also highly specific to the biomolecule, but does not compete with the first bound antibody or recognition molecule on insulation layer 3. The secondary antibody also binds to the biomolecule of interest thereby providing extra mass to the surface of sensor 100, in comparison with the biomolecule alone. The larger mass increase leads to an enhanced response. The secondary antibody or reporter DNA that is complementary to the target DNA but different from the probe DNA on the PEPS surface may be tagged with microspheres, microrods or microplates or nanospheres, nanorods, nanoplates, vesicles, to bring even more mass to the surface of sensor 100.

Secondary antibodies that do not compete with the bound antibodies may be identified from panels of single-chain variable fragment (scFv) antibodies isolated from combinatorial naive phage display libraries or from commercial sources. Additionally, the secondary antibodies may be formulated from new scFv antibodies that are isolated from other scFv phage display libraries in the presence of high concentrations of the primary antibodies to promote the isolation of non-competing clones.

Combinatorial naive phage display libraries are another source for non-competing secondary antibodies. These libraries are typically created through the random combination of human variable light and variable heavy chain domains, resulting in the creation of antibodies that are specific for regions, i.e. epitopes, on target antigens that are not normally immunogenic. The use of phage display therefore significantly increases the areas on the antigen that can be bound by a secondary antibody.

In some embodiments, the sensitivity of the PEPS 100 may be enhanced by using a receptor. One or more receptors may be included, which can specifically bind to the biomolecule of interest. The receptor binds to the biomolecule, and the receptor also binds to the recognition molecule on the surface of the PEPS 100. In this manner, extra stress is brought to the surface of sensor 100 by the receptor, in comparison with binding of the biomolecule alone. Detection sensitivity is thus enhanced since lower concentrations of biomolecule will generate an enhanced response due to the extra stress brought to the surface of sensor 100 by the receptor. The receptor may further be tagged by microsphere, microrod or microplate, nanopsheres, nanorods, nanoplates, or vesicles to bring even more mass to sensor 100. In one embodiment, use of microspheres is able to enhance detection sensitivity by a factor of 2. In another estimate, such embodiment could enhance the detection sensitivity by a factor from 2 to $10^6$, or 3 to $10^5$, 4 to $10^4$, or 5 to $10^3$, or 6 to $10^2$, or 7 to 10.

The receptor may be conjugated with one or more nanoparticles or nanomaterials, such as quantum dots. The nanoparticles or nanomaterials may be capable of fluorescing to further enable visualization and imaging of the captured substance of interest to confirm the presence of the biomolecule of interest in the sample. Therefore, it is possible to view a sample under a fluorescent microscope and determine the concentration of biomolecule of interest based on the photoluminescence of the quantum dot. Quantum dots are particularly useful in imaging proteins and cells in biological systems due to their stability against photobleaching and their ability to be conjugated to recognition molecules such as antibodies. Typically, clusters of quantum dots are able to better image biological organisms with brighter luminescence than single quantum dots; therefore, quantum dot-populated binding substrates are expected to significantly enhance molecular imaging.

Quantum dots may be synthesized using any standard fabrication techniques and may be of any suitable size. The environmentally friendly method for fabricating quantum dots disclosed in W. H. Shih, H. Li, M. Schillo, and W. Y. Shih, "Synthesis of Water Soluble Nanocrystalline Quantum Dots and Uses Thereof," U.S. Pat. No. 7,335,345, Feb. 26, 2008, is incorporated herein by reference in its entirety. In addition, nontoxic QDs disclosed in U.S. patent application Ser. No. 11/943,790, "Synthesis of Water Soluble Nanocrystalline ZnS Quantum Dots and Uses Thereof," filed on Nov. 21, 2007, and near-infrared QDs disclosed in U.S. provisional patent application No. 61/046,899, "Water-soluble Nanocrystalline Quantum Dots Capable of Near Infrared Emissions," filed on, Apr. 22, 2008 are also incorporated herein by reference in their entirety.

PEPS 100 may be refurbished for reuse. During the refurbishing process, the recognition molecule on the surface of the PEPS 100 may be removed, together with any substance bound to the recognition molecule. For this purpose, the used sensor 100 may be submersed in a 1:100 dilution of piranha solution (two parts of 98% sulfuric acid with one part of 30% hydrogen peroxide) for 30 seconds, rinsed with deionized water, then rinsed with 95% ethanol to completely remove water. Sensor 100 is then submerged in a sealed container of a 1% v/v MPS and ethanol titrated to a pH 4.5 with acetic acid for 8 hours, rinsed with ethanol and allowed to air dry. Sensor 100 is then ready for re-functionalization to bind a recognition molecule on the surface thereof.

PEPS 100 may be reused without being refurbished. For an antibody-functionalized PEPS 100, the bound antigen can be effectively removed by immersing in 2 M MgCl2 for 30 seconds, followed by immersing in 1.5 M Tris, pH 8.8 for an additional 30 seconds. The regenerated PEPS 100 is then blocked with BSA for a subsequent detection run. The −Δf/f of a reused PEPS 100 may be about 90-95% of a fresh or refurbished PEPS 100 when reused for the first time and about 87-90% of a fresh or refurbished PEPS 100 when reused for a second time. For a pDNA-functionalized PEPS 100, the bound DNA may be de-hybridized and removed in a flow of PBS maintained at 80-85° C. for 30 min. For DNA detection, the −Δf/f of a reused PEPS 100 may be about 98% of a fresh or refurbished PEPS 100 and that for a PEPS 100 reused for a third time may be about 95% of a fresh or refurbished PEPS 100.

PEPS 100 may be used for detection of biomarkers using any resonance frequency peak and may be operated a length, width or planar extension resonance mode or a combination thereof. Length extension mode and width extension mode enable more sensitive detection with higher peak frequency intensities and minimized damping effects. Sensor 100 may be used at resonance frequencies of from about 10 kHz to about 10 GHz.

When assessing the effectiveness of a therapeutic treatment, PEPS 100 may be used to quantitatively measure the concentration of one or more biomarkers prior to administering the therapeutic treatment to establish a baseline. The concentration of the same biomarkers may be subsequently measured at one or more points in time over the period when the therapeutic treatment is being administered and/or after the treatment has concluded. The concentration of the biomarkers may be measured as frequently as necessary to establish statistically significant and reliable results. The concentration levels measured during or after the completion of treatment may be compared to the patient's pre-treatment level or previously recorded levels obtained earlier in the treatment or post-treatment process to provide an indication of the effect of the treatment on that patient.

Additionally or alternatively, the measured concentration levels may be compared with established ranges indicative of normal and/or abnormal concentration levels. The trend in the concentration levels of the biomarker over time and the comparison with established normal and abnormal concentration ranges may be used to determine the effectiveness of a therapeutic treatment, whether there has been any change in the progress of a disease or condition, or even to provide early detection of potentially dangerous immunological responses to particular treatments such as a severe allergic reaction to a particular therapeutic agent.

PEPS 100 of the present invention is also an effective diagnostic tool that may be used for medical diagnosis of various diseases, e.g. breast cancer, lung cancer, colorectal cancer, pancreatic cancer, gastric cancer, liver cancer, ovarian cancer, prostate cancer, myocardial infarction, diarrhea, *Clostridium difficile* infection, HIV, and hepatitis B infection.

Diagnosis of Breast Cancer

Several biomarkers have been linked with breast cancer. Human epidermal growth factor receptor 2 (HER2) is over-expressed in 25-30% of breast cancer patients. Epidermal growth factor receptor (EGFR) is over expressed in 57% of breast tumor patients with negative to estrogen, progesterone, and HER2. Tn antigen is present in 90% of breast cancer patients. Tn antigen also elicits an immune response. Vascular endothelial growth factor (VEGF) is over-expressed in many breast cancer patients. Molecular imaging techniques such as positron emission tomography (PET) and gamma emitting radionuclide for single photon emission computed tomography (SPECT) are under development to image these biomarkers as an auxiliary test to mammography to improve the sensitivity and specificity of breast cancer screening and monitoring. However, these molecular imaging techniques are either radioactive or costly or both.

These breast cancer biomarkers over-expressed in the tumors also circulate in blood streams. For example, elevated circulating VEGF levels are found in 62% of breast cancer patients with 74% specificity. Normal individuals' blood VEGF levels are 50-160 pg/ml and breast cancer patients' levels are 160-450 pg/ml. HER2-positive breast cancer patients' HER2 levels are from 15 to 75 ng/ml while normal individuals' and HER2-negative patients' HER2 levels are between 2 and 15 ng/ml. These biomarkers present an excellent opportunity for simple, low cost breast cancer diagnostic method with high sensitivity and specificity.

The concentration of these breast cancer biomarkers are likely to be elevated years before the cancer is clinically diagnosed (tumor grow to sufficiently large to be detectable by mammography) as demonstrated by a recent study of serum levels of CA125, HE4, and mesothelin elevation in subjects before diagnosis of ovarian cancer. The present invention uses PEPS 100 to detect the breast cancer biomarkers in serum to aid diagnosis of breast cancer, especially at early stages.

Figure 3:
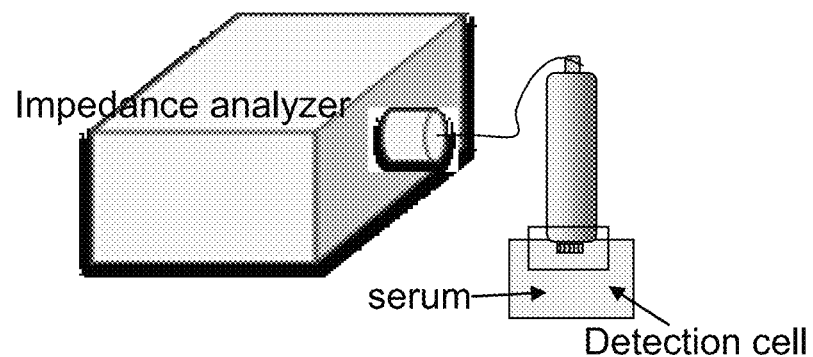
FIG. 3 is a diagram showing a system with a portable measurement device connected with an array of piezoelectric plate sensors in a detection cell.
Figure 4A:
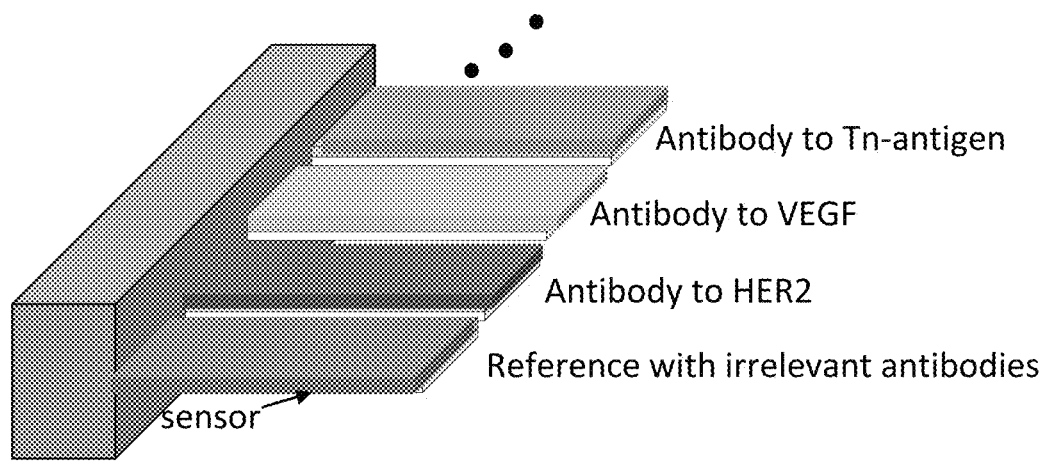
FIG. 4A is a diagram showing the array of piezoelectric plate sensors used in FIG. 4A. The piezoelectric plate sensors are functionalized with different antibodies.
Figure 4B:
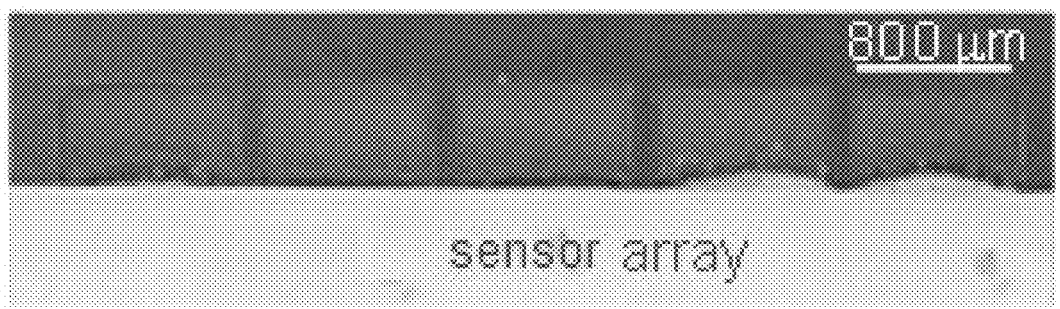
FIG. 4B shows a top view of the PEPS array of FIG. 4A.

In diagnosis of breast cancer, the present invention provides a system for detecting elevated breast cancer biomarkers such as HER2, EGFR, VEGFR, Tn and anti-Tn antibody in serum of patients. The system has a measurement device connected with an array of piezoelectric plate sensors 100 (FIG. 3). The measurement device may be a battery-powered portable device for convenience. Multiple breast cancer biomarkers may be detected simultaneously using the array of piezoelectric plate sensors 100, with each PEPS 100 in the array functionalized with an antibody specifically for one of these breast cancer biomarkers (FIGS. 4A and 4B). The sensor array is exposed to serum in a detection cell. The specific binding of a breast cancer biomarker to a PEPS 100 in the sensor array causes resonance frequency shift for the PEPS 100, which is measured by the measurement device (FIG. 3). In one embodiment, the measurement device is an AIM 4170 impedance analyzer for measuring resonance spectra of the PEPS 100.

Antibodies that bind with one or more of the breast cancer biomarkers are attached to insulation layer 3 by, for example, a sulfo-SMCC bi-functional linker. The functionalized piezoelectric plate sensors 100 are then coated with bovine serum albumin (BSA) to block non-specific binding on the surface of the sensors. In one embodiment, the BSA coating may be accomplished by treating the functionalized piezoelectric plate sensors 100 with a 30 mg/ml (5%) BSA solution for 2 hours, followed by rinsing with 10 mg/ml (1%) BSA and Tween 20 for 10 minutes.

In measuring the breast cancer biomarkers, the array of piezoelectric plate sensors 100 is exposed to a serum sample from a patient for about at least 20 minutes, or about at least 25 minutes, or about at least 30 minutes, to allow the breast cancer biomarkers to bind with respective antibodies on the piezoelectric plate sensors 100. The resonance frequency shift of each of the piezoelectric plate sensors 100 is measured for detection of breast cancer biomarkers in the serum. The invention is able to achieve high sensitivity of detecting <1 pg/ml of the breast cancer biomarker in serum.

This method of diagnosing breast cancer may be extended to other cancers that have known biomarkers in samples such as blood. For example, ovarian cancer can be detected by elevated levels of CA125, HE4, mesothelin, Tn antigen and anti-Tn antibody in blood. Detection of Tn antigen and anti-Tn antibody in serum can be extended to detect epithelial cancers such as lung cancer, pancreatic cancer, gastric cancer, colorectal cancer, prostate cancer, skin cancer, kidney cancer, and bladder cancer. Tn antigen and anti-Tn antibody may be detected in serum or in sputum as in the case of lung cancer, or in nipple aspirate as in the case of breast cancer, or in stool as in the case of colorectal cancer, or in urine as in the case of renal cancer or bladder cancer.

For diagnosis of lung cancer, EGFR may be used as a biomarker, in addition to Tn antigen. The EGFR in sputum from a patient may be measured using a piezoelectric plate sensor 100 functionalized with anti-EGFR antibody. This may be used as a screening step to help identify patients who need a further low-dose CT scanning screen. For colon cancer, the biomarkers may be Kras, PAC, and TP53 in stool. This may be a screening step for identify patients who need a further colonoscopy examination.

Diagnosis of Myocardial Infarction

Cardiac troponin, a structural protein unique to the heart, is a sensitive and specific biomarker of myocardial damage. Even slight damage to the heart causes the release of cardiac troponin into the blood. Since myocardial infarction causes damage to the heart it also causes cardiac troponin to be found in the blood.

Figure 5:
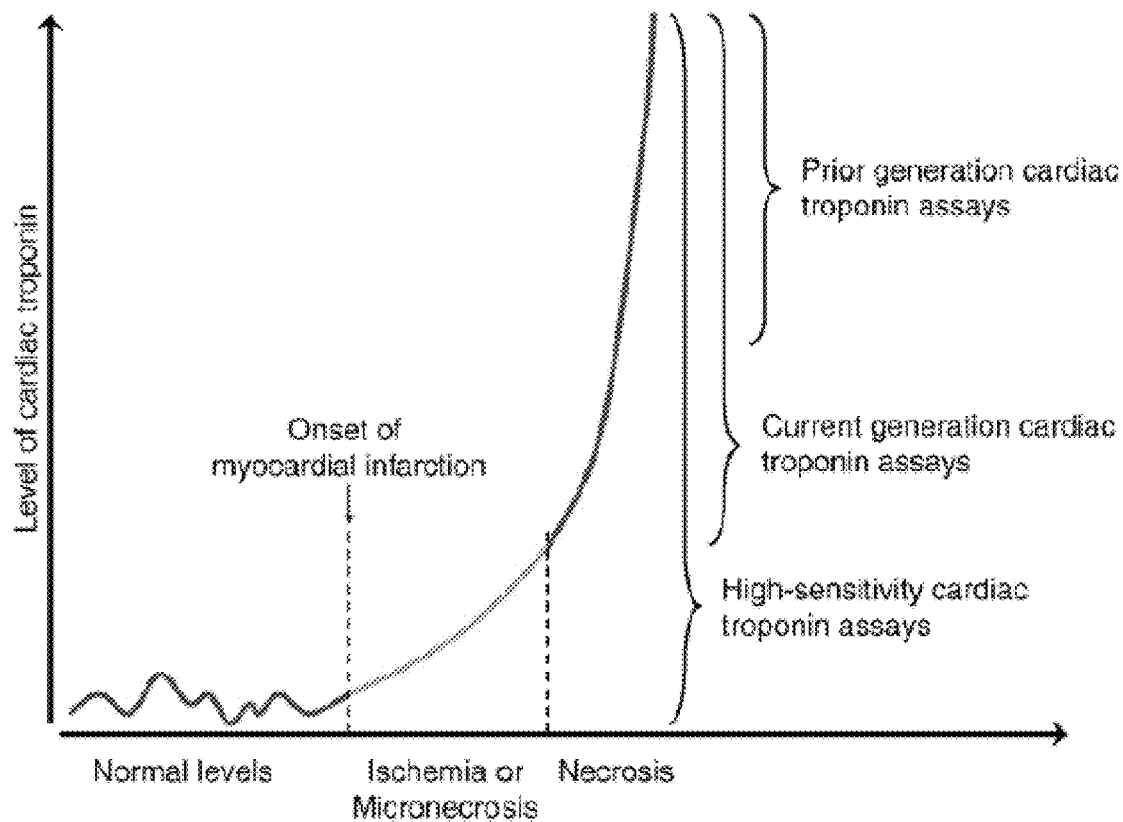
FIG. 5 is a plot showing cardiac troponin concentration in serum at different stages of myocardial infarction.

The serum cardiac troponin level closely tracks the progress of myocardial infarction, as illustrated by FIG. 5. For normal people, serum cardiac troponin is on the level of pg/ml or lower. This low serum cardiac troponin level is undetectable by the current immunoassays. At the onset of myocardial infarction, there is a slight rise in cardiac troponin that reflects either ischemia-induced release of cytosolic troponin or micronecrosis. 2 to 6 hours after onset, a steep increase in levels of cardiac troponin can be seen that reflects extensive myocardial necrosis. Thus, when a myocardial infarction event has occurred, the serum cardiac troponin level rises over time as shown in FIG. 5.

While high-sensitivity troponin assays are commercially available, they generally take 4-5 hours to complete. Therefore, they are not suitable for detecting early signs of myocardial infarction, since by the time the assay is complete, the MI event is well progressed and damage to the heart is already severe. Therefore, there is a need for an assay that can accurately and rapidly detect very low levels of serum cardiac troponin within the first hour of arrival at the emergency room. Such real-time, sensitive serum cardiac troponin level information would allow a physician to determine in real time if the patient's serum cardiac troponin level is rising, thereby providing a sufficiently early diagnosis of myocardial infarction to permit timely treatment.

A PEPS 100 functionalized with an antibody that binds to serum cardiac troponin can provide rapid, accurate detection of cardiac troponin in a patient's serum. The troponin antibody may be bound to sensor 100 using a sulfo-SMCC linker or a biotin. BSA may be used to coat the functionalized sensor 100 to block non-specific binding. The functionalized sensor 100 may be exposed to the serum for period from about 5 minutes to about 30 minutes, or from about 7 minutes to about 25 minutes, or from about 10 minutes to about 25 minutes, or from about 13 minutes to about 25 minutes, or about 15 minutes to about 25 minutes. A resonance frequency shift is caused by the binding of cardiac troponin on the surface of the functionalized sensor 100 and can be measured to determine the presence and/or concentration of troponin in the serum. Therefore, early diagnosis of myocardial infarction becomes possible.

This assay can achieve a very high detection sensitivity on the order of <0.05 pg/ml cardiac troponin in serum. In addition, the assay is simple to run and can generate a result rapidly, e.g. within 20-30 minutes, at low cost.

Diagnosis of Diarrheal Diseases

The most common causes of infectious diarrhea are viruses in developed countries, bacteria such as enteropathogenic *E. coli, S. enterica, V. cholerae, Shigella* spp and *C. jejuni* account for most diarrheal infections elsewhere. A diagnostic method capable of rapidly identifying these diarrheal pathogens is needed to allow timely treatment and prevention of the disease. Conventional methods for detecting pathogens involve days of bacteria culturing, microscopy observation, followed by biochemical identification, and serotyping, which is too time-consuming for a timely response to an outbreak or bioterrorist attack.

A PEPS 100, or an array of sensors 100, each functionalized with a nucleic acid probe for specifically detecting the genetic signature of one of these diarrheal pathogens can be used to provide a rapid, reliable test for the presence and concentration of these pathogens. Thus, any sequence fragment, especially a genomic DNA sequence fragment that is unique to a diarrheal pathogen may be used as a genetic signature of that diarrheal pathogen. A nucleic acid probe complementary to one or more genetic signatures of diarrheal pathogens can be used for detecting these DNA fragments, thus indicating the presence of diarrheal pathogen.

Binding of a nucleic acid probe on insulation layer 3 may be as discussed above.

An array of functionalized sensors 100 may also be used wherein each sensor 100 functionalized with a nucleic acid probe for specifically detecting the genetic signature of a diarrheal pathogen. The bacteria in the sample may be lysed and the double strand DNA may be denatured. The array of piezoelectric plate sensors 100 is then contacted with the sample for a time sufficient for the nucleic acid probe to bind to the genetic signature DNA fragments of the diarrheal pathogens. The time for incubating the sample with the array of piezoelectric plate sensors 100 may be from about 10 minutes to about 30 minutes, or from about 15 minutes to about 25 minutes, or from about 18 minutes to about 22 minutes.

This diagnosis method for diarrheal disease offers several advantages, such as no need for DNA isolation, concentration, or amplification. Also, the genetic signatures from multiple diarrheal pathogens may be detected directly from a single sample at a concentration as low as from about 10 to about 60 copies/ml in less than 30 minutes.

Diagnosis of *Clostridium Difficile* Infection

Infections caused by toxin-producing strains of *Clostridium difficile* (CD) cause diseases from mild diarrhea to fulminant sepsis, resulting in colectomy and even death. The present invention provides a method for diagnosing CD infection using a PEPS 100 functionalized with a nucleic acid probe for specifically detecting a genetic signature of CD. A genomic DNA sequence fragment of CD that is unique to CD may be used as genetic signature of CD. A person skilled in the art may thus design a nucleic acid probe that is complementary to one or more selected genetic signatures of CD for detecting these genomic DNA sequence fragments, thus enabling detection of CD in a sample. Binding of the nucleic acid probe on insulation layer 3 may be accomplished in the same manner as discussed above.

The PEPS 100, with the nucleic acid probe specifically for detecting the genetic signature of CD attached thereto, is then exposed to a sample such as a stool sample. The CD bacterial cells in the sample may be lysed (e.g., by sodium dodecyl sulfite) to release the genetic signature (DNA fragment) from the bacterial cells. The sample may also be treated at high temperature as discussed above.

This diagnosis method for CD infection may also comprise an assay for detecting the toxin produced by CD. For this assay, an antibody for the CD toxin may be bound to the surface of a PEPS 100. The binding of the antibody may be through, for example, a sulfo-SMCC linker or a biotin. BSA or another suitable material may be used to coat the functionalized PEPS 100 to block non-specific binding. The functionalized PEPS 100 may be exposed to the same for the same time periods as described above.

Using a combination of a PEPS 100 functionalized with a nucleic acid probe to detect CD genetic signature and a PEPS 100 functionalized with an antibody to detect CD toxin, the present invention is capable of detecting CD infections at early stages with high sensitivity at low cost. A CD concentration as low as from about 10 to about 60 copies/ml can be detected. A CD toxin can be detected at about 0.1 pg/ml or lower concentrations, or at a concentration of about 0.05 pg/ml or lower, in the sample.

Referring to FIG. 45, in one embodiment, the CD genetic signature may be two CD toxin genes: cdtB and tcdB. The array of PEPS 100 may have sensors each functionalized with a probe complementary to cdtB and tcdB respectively.

Diagnosis of Hepatitis B Infection

Hepatitis B is a viral infection caused by hepatitis B virus (HBV). Currently, chronic hepatitis B is the major etiological factor for cirrhosis and hepatocellular carcinoma (HCC) worldwide. Unlike liver cancer caused by hepatitis C viruses (HCV), liver cancer caused by HBV may not be preceded by cirrhosis, making HBV-related liver cancer difficult to diagnose and treat at an early stage of the malignancy. Early treatment of Hepatitis B infection with antiviral medications has been approved to reduce the rate of liver cancer. Therefore, it is important to identify people with chronic HBV infection at an early stage so that they can be treated timely.

The present invention provides a method for diagnosing HBV infection using a PEPS 100 functionalized with a nucleic acid probe for specifically detecting a genetic signature of HBV. A viral genomic DNA sequence fragment of HBV that is unique to HBV may be used as genetic signature of HBV. A person skilled in the art may thus design a nucleic acid probe that is complementary to one or more selected genetic signatures of HBV for detecting these viral genomic DNA sequence fragment(s), thus providing an indication of the presence of HBV in a serum sample.

Binding of the nucleic acid probe on insulation layer 3 and treatment to reduce non-specific binding may be carried out as discussed above. The functionalized sensor 100, with the nucleic acid probe for specifically detecting the genetic signature of HBV, is then exposed to a sample such as a serum sample of a subject. The HBV viral particles in the serum sample may be lysed (e.g., by sodium dodecyl sulfite) to release the genetic signature (DNA) from the viral particles and treated at high temperature to denature the DNA as discussed above. The same time periods discussed above for incubating the serum sample with the functionalized PEPS 100 may also be employed for this use.

The method is able to detect 30 copies/ml HBV viral DNA within 30 minutes at low cost, without the need for isolation of the viral particles or amplification of the viral DNA.

Because of the high sensitivity of PEPS 100 in detecting single-stranded DNA, it is now possible to incorporate PEPS 100 in a continuous flow and with sodium dodecyl sulfate (SDS) to detect DNA fragments which are double-stranded in a body fluid such as serum, sputum, urine, saliva, and stool in situ without the need of DNA to isolate the DNA or amplify the DNA. FIG. 46 is a schematic of a continuous flow which contains: (1) a high-temperature (such as 95° C.) chamber or reservoir where the sample is loaded with SDS and heated for 1-10 min to expose and denature the double stranded DNA, (2) a fast cooling module where the sample is cooled from 95° C. to the detection temperature in <30 sec, and (3) a detection flow chamber where the sample is held at the detection temperature and the PEPS 100 is held at the center of the flow to detect the denatured target DNA. With the same methodology, samples containing bacteria and or viruses can be loaded in the high-temperature reservoir with SDS to lyse the bacteria/viruses, release the DNA, and denature the DNA, fast-cool the sample through the cooling module and directly detect the genetic signatures of bacteria/viruses right in the detection cell chamber without the need of isolating the DNA or amplifying the DNA. Such a rapid, continuous, and in situ detection scheme is only possible due to the high detection sensitivity of the PEPS 100. The current invention of the highly sensitive PEPS 100 coupled with a continuous flow system is unique in that it can detect DNA at concentrations that otherwise can only be detected by PCR or LAMP (loop-mediated isothermal amplification), which both require DNA isolation and amplification. PCR and LAMP also require expensive fluorescent probes while PEPS does not.

The present invention is also suitable for detecting genetic mutations in a DNA. These genetic mutations may include, for example, a point mutation, a multiple-point mutation, an insertion, and a deletion. Detection of genetic mutations may be used for diagnosis of cancer or a genetic disorder.

In detecting genetic mutations, the DNA molecules in a sample may be heated or treated with sodium dodecyl sulfide under conditions sufficient to expose the DNA and denature the DNA. The recognition molecule is a nucleic acid probe for specifically detecting the genetic mutation.

For example, the K-ras codon 12 mutation is a marker for detection of colorectal cancer (CRC). The sample may be blood (serum and plasma) stool, and urine. The K-ras mutation has a low incidence in cancer of the urinary tract. Thus, mutated K-ras DNA can be used as a representative of a mutation occurring at a tumor site outside of the urinary tract.

The present invention is also suitable in detecting genetic hypermethylation in a DNA, which may be suitable for diagnosis of cancer or a genetic disorder. In detecting genetic hypermethylation, the sample may be treated with bisulfate to convert unmethylated cytosines in the DNA to uracils to create point differences between the DNA comprising hypermethylation and the wild type of the DNA. The sample may also be heated or treated with sodium dodecyl sulfide under conditions sufficient to expose the DNA and denature the DNA. The recognition molecule is a nucleic acid probe for specifically detecting the genetic hypermethylation in the DNA.

Nucleic acid probes on PEPS 100 may be used to detect Hepatocellular carcinoma (HCC) associated nucleic acid markers (including genetic and epigenetic DNA markers and microRNAs) for the early detection of liver cancer.

EXAMPLES

The following examples are illustrative, but not limiting, of the methods and compositions of the present disclosure. Other suitable modifications and adaptations of the variety of conditions and parameters normally encountered in the field, and which are obvious to those skilled in the art, are within the scope of the disclosure.

Example 1

Glass slides were coated with a 100 nm thick gold electrode with a 10 nm thick chromium bonding layer by thermal evaporation (Thermionics VE 90). These gold coated glass slides were then cut into 3 mm by 4 mm strips. A gold wire was then attached to each gold strip with a conductive glue (8331, MG Chemicals) and the rear end of the strip with the gold wire was then attached to a glass substrate and cover with non-conductive glue (LOCTITE™) to form a "cantilever" shape. After soaking in 1:100 diluted piranha solutions (3 parts sulfuric acid and one part 30% hydrogen peroxide solution) for 1 min, rinsed in deionized (DI) water and ethanol, the gold-coated glass cantilever were then soaked in 0.01 mM MPS solution with 1% DI water in ethanol for 30 min followed by rinsing in DI water and ethanol. Afterward, each gold-coated glass cantilever was soaked in a MPS solution with DI water in ethanol at different pH values ranging from pH=4.5 to 9 for 12 hr three times. For comparison, coatings made with 1% (by volume) MPS with 1% (by volume) water and without water as well as 0.1% MPS (by volume) with 0.5% (by volume) water were also prepared. Note that all percentages in the examples were by volume. To achieve the desired pH value, an appropriate amount of acetic acid (99%, Sigma-Aldrich) or potassium hydroxide (100%, Fisher) was added to the MPS solutions. For example, to achieve pH=4.5, 5.5, 6.5, 228 μl, 46 μl, and 8 μl of acetic acid were added to 50 ml of MPS solution, respectively, and for pH=8.0 and 9.0, 77 mg and 117 mg of potassium hydroxide were added to 50 ml of MPS solution, respectively. To minimize the possible MPS cross-linking in the solution, after the initial 12 hr MPS solution soaking period, the gold-coated cantilever was rinsed with DI water and ethanol and then placed in a new MPS solution of the same pH for 12 hr two more times. Each time, the cantilever was rinsed with DI water and ethanol before immersing it in a fresh MPS solution.

Example 2

Cyclic voltammetry (CV) in 10 mM $K_3Fe(CN)_6$ and 0.1M KCl solution in DI water was measured with a potentiostat (283, EG&G Instruments) to characterize the insulation quality of the MPS coating layer fabricated in Example 1. To determine the capacitive effect of insulation layers at different scan rates, a CV scan in 0.1M KCl solution in DI water was used. To characterize the rate of coating thickness increase in situ, MPS coating on the gold electrode of a 5 MHz quartz crystal microbalance (QCM) was carried out in an enclosed flow cell which was connected to the MPS solution reservoir by tubing and the flow was driven by a peristaltic pump (7710-62, Masterflex C/L) at 1.5 ml/min. The resonance frequency of the QCM was monitored using an impedance analyzer (AIM4170C, Array Solutions). The increase in the coating thickness, $\Delta t$, is related to the QCM's resonance frequency shift, $\Delta f$, as defined by equation:

$$\Delta t = -\frac{c}{2f^2}\Delta f, \quad \text{(Equation 3)}$$

where f was the resonance frequency of the QCM, $c=\sqrt{\mu/\rho}$ was the sound velocity in quartz with $\mu=2.947\times10^{11}$ g/cm·s$^2$ and $\rho=2.648$ g/cm$^3$ being the shear modulus and density of quartz, respectively. By monitoring the resonance frequency shift, a real-time increase in coating rate over time was obtained. In addition to QCM coating rate measurements, scanning electron microscopy (SEM) (XL30, FEI) was also used to examine a cross section and top surface of the coating layer.

Figure 6:
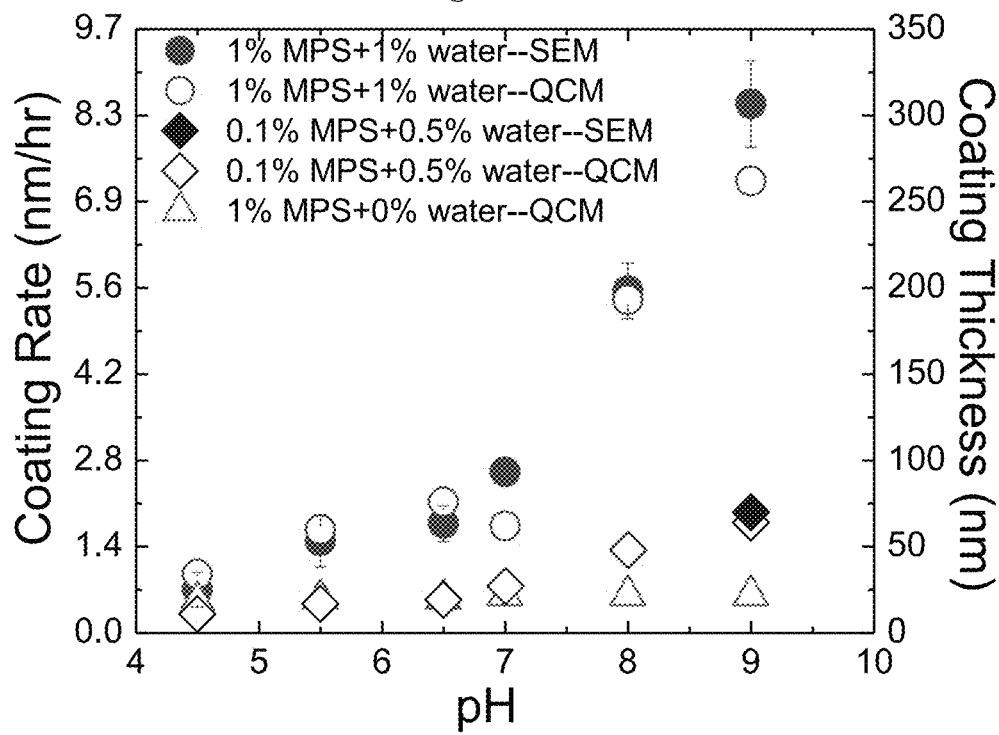
FIG. 6 is a plot showing coating rate and coating thickness versus pH using different coating methods.

The coating rate versus pH is plotted in FIG. 6. Also plotted in FIG. 6 is the coating thickness of an MPS coating applied over 36 hr (3×12 hr) as determined from available scanning electronic microscope (SEM) micrographs. With 0% water, the coating rate remained at about 0.5 to 0.6 nm/hr for all pH values whereas with 1% water, the coating rate increased with an increasing pH from about 0.8 nm/hr at pH=4.5 to about 8 nm/hr at pH=9.0, indicating that both the presence of water and a high pH were important for the MPS coating layer to grow. It was observed that the coating thickness at 36 hr, as estimated by multiplying the coating rate determined by QCM by 36 hours, generally agrees with that determined by SEM. The results in FIG. 6 suggest that thicker MPS coating layers can be obtained in the presence of water at a higher pH.

Example 3

To test the performance of the insulation layers, the width mode resonance frequency of piezoelectric plate sensors coated using various MPS coating processes was monitored. The sensors used were made of 8 μm thick PMN-PT film, and were 1070 μm long and 670 μm wide with one of the long ends fixed on a substrate in a cantilever shape. A 100 nm thick gold electrode was deposited on both sides of the PMN-PT film with a 10 nm chromium bonding layer by a thermal evaporator (Thermionics VE 90). The gold-coated PMN-PT films were then cut into 600-1000×2300 μm rectangular strips using a wire saw (Princeton Scientific Precision, Princeton, N.J.). Gold wires of 10 μm in diameter were then attached to the top and bottom electrodes using conductive glue (8331, MG Chemicals). The rear end of the strip was then glued to a glass slide to form plate geometry. The strips were poled at 15 kV/cm and 80° C. for 30 min on a hotplate. The strips were then insulated with various coating processes (as used in Example 1) for resonance frequency stability testing in phosphate buffer saline (PBS) solution.

Figures 7A, 7B, 7C:
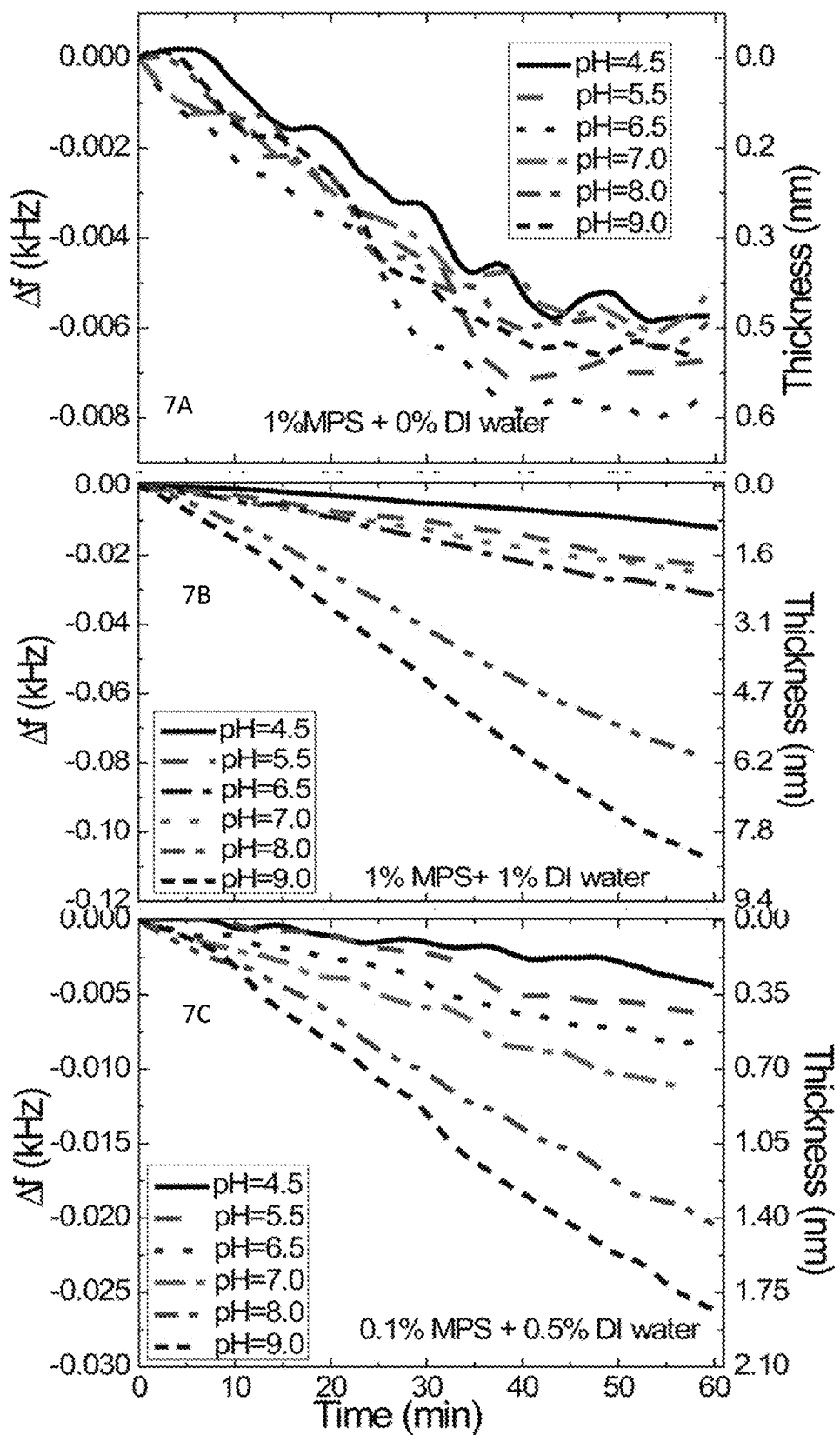
FIG. 7A shows the resonance frequency shift (Δf) of piezoelectric plate sensors with an insulation layer fabricated with a 1% MPS solution in ethanol with 0% deionized (DI) water at different pH's. The thickness of the insulation layer is shown on right y-axis.
FIG. 7B shows the resonance frequency shift (Δf) of piezoelectric plate sensors with an insulation layer fabricated with a 1% MPS solution in ethanol with 1% DI water at different pH's. The thickness of the insulation layer is shown on right y-axis.
FIG. 7C shows the resonance frequency shift (Δf) of piezoelectric plate sensors with an insulation layer fabricated with a 0.1% MPS solution in ethanol with 0.5% DI water at different pH's. The thickness of the insulation layer is shown on right y-axis

In FIGS. 7A-7B, the resonance frequency shift, $\Delta f$, versus time of a QCM coated with a 1% MPS solution in ethanol at various pH values with 0% DI water (FIG. 7A) or with 1% DI water (FIG. 7B) is shown. Also depicted on the right y-axis is the coating thickness as calculated using Equation 3. The coating rate in nm/hr is the least-square fit of the slopes of the curves in FIGS. 7A-7B.

Figure 8A:
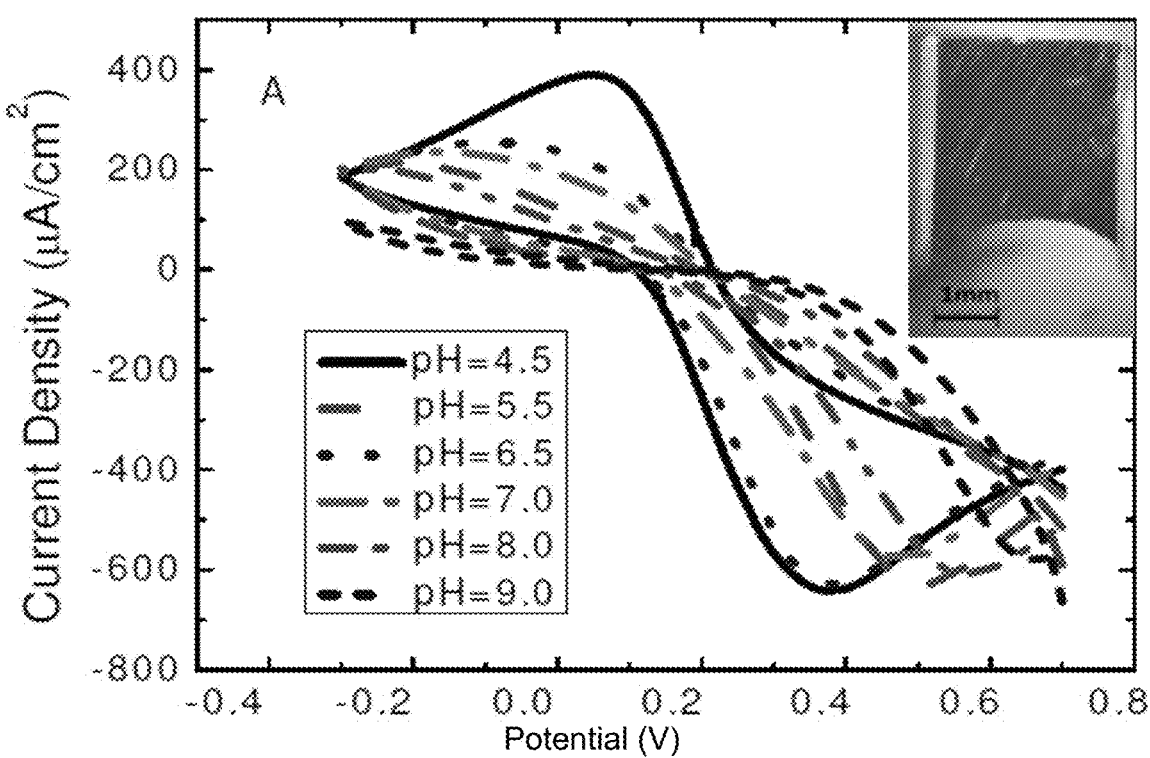
FIG. 8A shows current density versus potential for piezoelectric plate sensors with an insulation layer fabricated with a 1% MPS solution in ethanol with 0% DI water at different pH's. The insert shows an optical micrograph of one of the gold-coated glass slides used for the experiments.
Figure 8B:
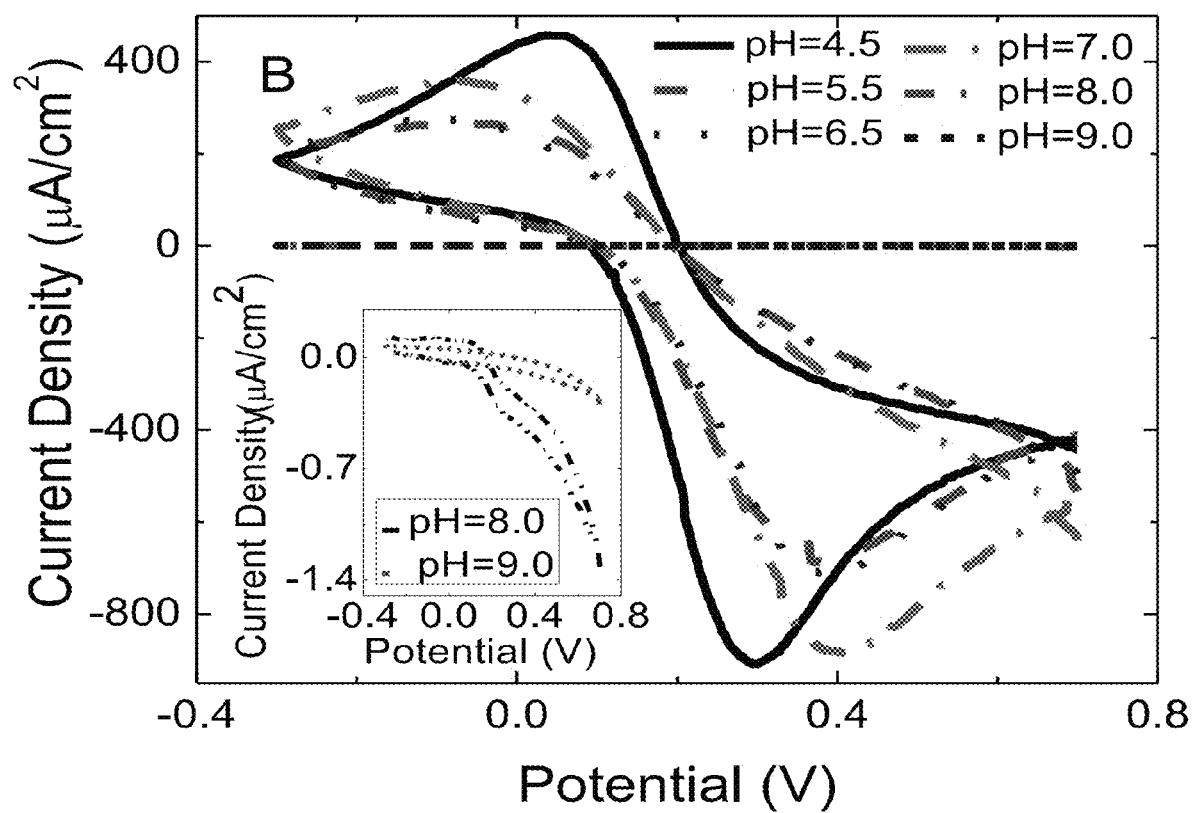
FIG. 8B shows current density versus potential for piezoelectric plate sensors with an insulation layer fabricated with a 1% MPS solution in ethanol with 1% DI water at different pH's. The insert shows the piezoelectric plate sensors coated at a pH of 8.0 and a pH of 9.0.

The insulating performance of the MPS coating layers on a gold surface after 36 hr (3×12 hr) of coating was examined by cyclic-voltammetry (CV) with 100 mV/s of scan rate. The current density, J, versus the potential of gold electrodes was plotted. The results for the 36 hr MPS coating made using 1% MPS in ethanol with 0% water are shown in FIG. 8A and the results for the MPS coating made using 1% MPS in ethanol with 1% water are shown in FIG. 8B, at various pH values in the range of 4.5 to 9.0. The current density was obtained by dividing the current passing through the MPS-coated gold electrode by the contact area with the liquid.

The insert in FIG. 8A is an optical micrograph of a gold-coated glass slide used for the CV tests. It was observed that in these CV plots, the maximum amplitude of current density ($J_{max}$), occurred at around a potential=0.4 V. FIG. 8A shows that for coatings made with 0% water, $J_{max}$ remained at around 600 μA/cm$^2$ whereas for coatings made with 1% water, $J_{max}$ decreased dramatically from 400-800 μA/cm$^2$ for pH≤7 to 1.2 and 0.2 μA/cm$^2$ at pH=8.0 and 9.0, respectively (see the insert of FIG. 8B). This represented a three-orders-of-magnitude decrease in $J_{max}$ due to the combined effects of 1% water and the pH of 9.0. The decrease of $J_{max}$ was also consistent with the rapid increase in coating rate at pH=8.0 and 9.0 shown in FIG. 6.

While the above result indicate that MPS coatings obtained at pH=8.0 and 9.0 exhibited excellent electrical insulation properties, microscopic examination of the coating morphology indicated that the coating surface was rough. As an example, the cross-section and the top-view SEM micrographs of a 36 hr MPS coating in 1% MPS in ethanol with 1% water are shown in FIGS. 9A-9B. From FIG. 9A, it is observed that there is an MPS coating of about 300 nm thick that was consistent with the coating rate of 8 nm/hr measured by QCM as shown in FIG. 6. However, on top of the smooth 300 nm thick MPS coating, there were large spherical particles. These large spheres were formed in the solution due to high hydrolysis and condensation rates for forming silica spheres in the solution at pH 9. FIG. 9C shows a cross-section SEM micrograph of a 36 hr MPS coating obtained from 1% MPS in ethanol and 1% water at pH=8.0. At this pH, fewer spheres were formed in the solution, though such spheres still deposited on the coating surface, causing surface roughness.

To minimize the formation of large spheres on the surface of the insulation layer at pH=9.0, an MPS coating was prepared with 0.1% MPS in ethanol and 0.5% water at various pH values. The QCM resonance frequency shifts versus time due to the MPS coating on the gold electrode surface are shown in FIG. 7C where the corresponding coating thickness is labeled on the right y-axis. The least-square fit of the slope of each of the curves shown in FIG. 7C was taken as the coating rate, which was plotted versus pH as diamonds in FIG. 6. This plot shows that at pH=9.0, the coating rate increased with an increasing pH from about 0.35 nm/hr at pH=4.5 to about 2 nm/hr at pH=9.0.

Figure 8C:
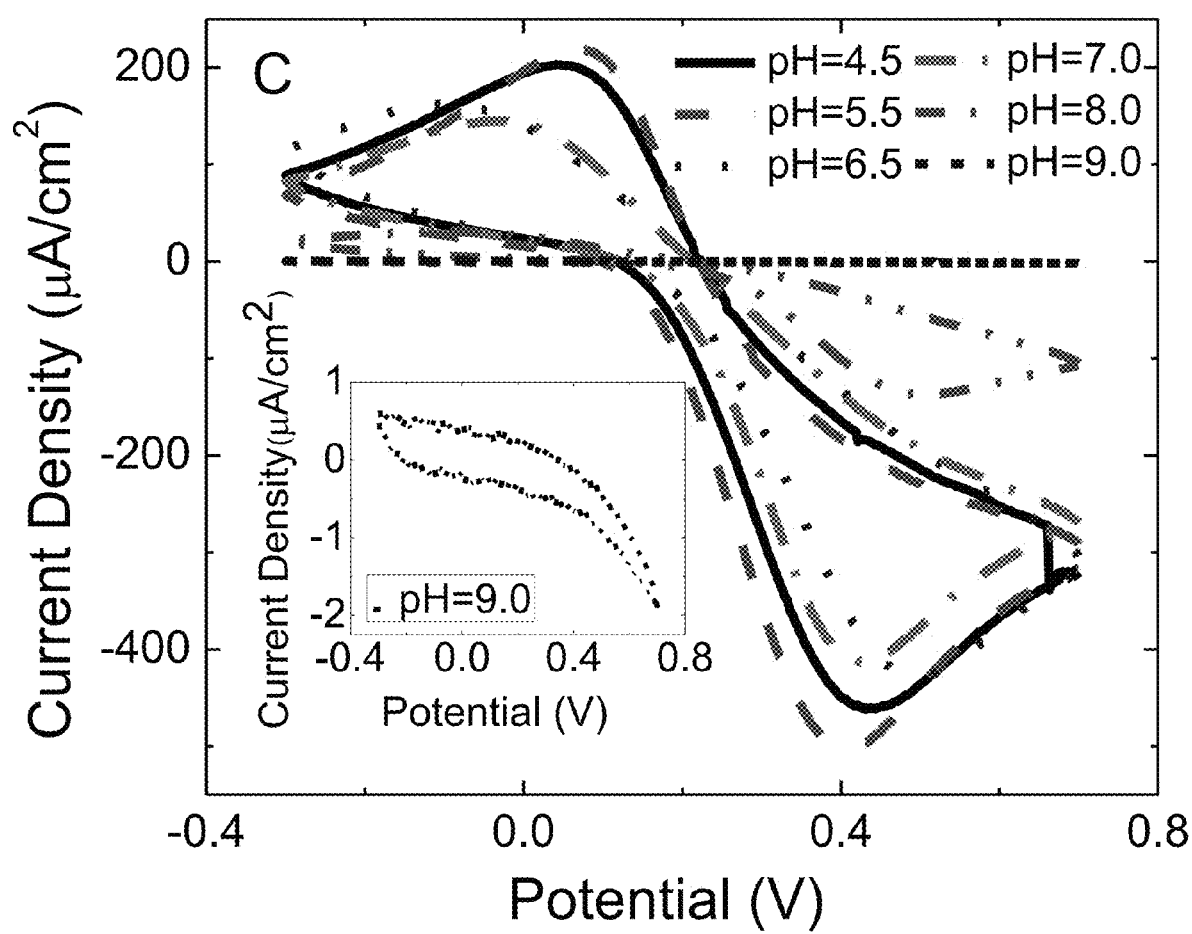
FIG. 8C shows current density versus potential for piezoelectric plate sensors with an insulation layer fabricated with a 0.1% MPS solution in ethanol with 0.5% DI water at different pH's. The insert shows the PEPS coated at pH=9.0.

The current density versus potential CV curve of the gold electrodes at various pH values are shown in FIG. 8C. For pH≤7.0, the maximal amplitude of current density, $J_{max}$, was about 400-600 μA/cm$^2$, whereas at pH=9.0 the maximal amplitude of current density was reduced to about 2 μA/cm$^2$, a more than two orders of magnitude improvement from those obtained at or below pH=7.0. FIGS. 10A-10B show the SEM cross-section micrograph and top-view micrograph, respectively, of the MPS coating on a gold surface made at pH=9.0. Unlike the microspheres-covered MPS coating obtained with 1% MPS in ethanol and 1% water at pH=9.0, the MPS coating obtained in 0.1% MPS in ethanol with 0.5% water at pH=9.0 looked smooth and no spherical particles were observed (FIGS. 10A-10B).

Figure 11:
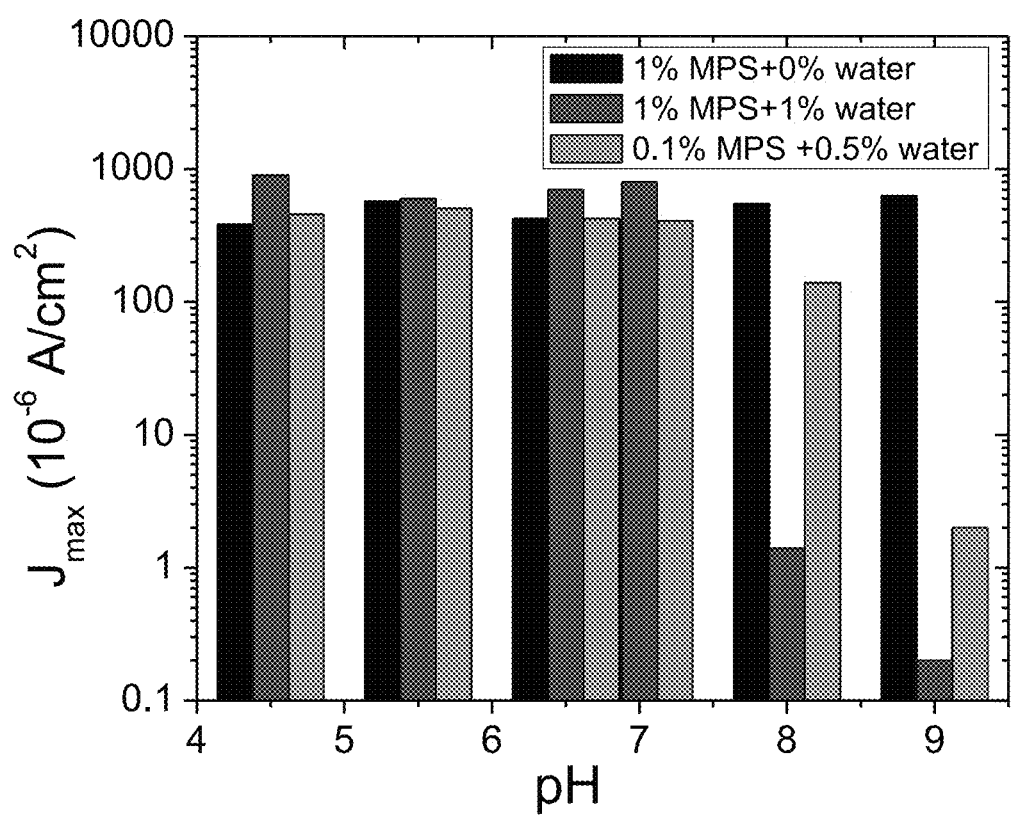
FIG. 11 shows the maximal amplitude of current density ($J_{max}$) versus pH for piezoelectric plate sensors with an insulation layer fabricated with different MPS ethanol solution.

FIG. 11 shows a plot of $J_{max}$ versus pH for gold electrodes coated with three different MPS solutions: 1% MPS in ethanol with 0% water, 1% MPS in ethanol with 1% water, and 0.1% MPS in ethanol with 0.5% water. Clearly, adding water and increasing the pH of the MPS solution to around 9.0 reduced the maximal current density by two to three orders of magnitude depending on the MPS concentration and water content. The smooth coating achieved by using 0.1% MPS in ethanol with 0.5% water at pH=9 is important for the long term insulation stability of the coating as well as providing a better controlled surface area for receptor binding thereby allowing accurate quantitative measurements to be taken.

Example 4

Figures 12A, 12B, 12C:
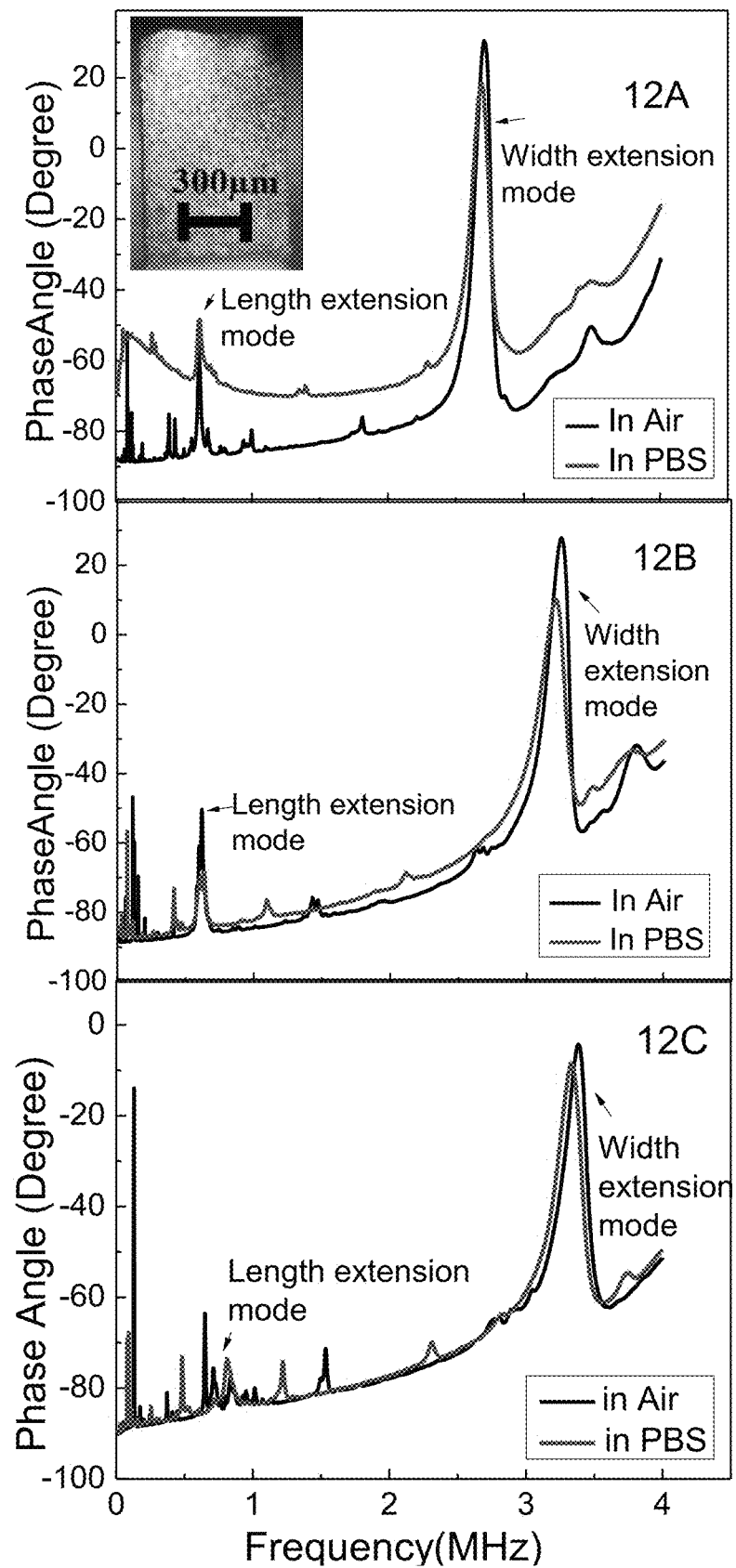
FIG. 12A shows phase angle versus frequency resonance spectra in-air and in phosphate buffer saline (PBS) for piezoelectric plate sensors with an insulation layer fabricated with a 1% MPS solution in ethanol with 0% water at pH=4.5. The insert shows an optical micrograph of a PEPS used in the experiment.
FIG. 12B shows phase angle versus frequency resonance spectra in-air and in-PBS for piezoelectric plate sensors with an insulation layer fabricated with a 1% MPS solution in ethanol with 1% water at pH=9.0.
FIG. 12C shows phase angle versus frequency resonance spectra in-air and in-PBS for piezoelectric plate sensors with an insulation layer fabricated with a 0.1% MPS solution in ethanol with 0.5% water at pH=9.0.

To examine the impact of coating conditions on the stability and reliability of the insulation layer fabricated under various coating conditions, piezoelectric plate sensors (PEPSs) were tested in-air and in-PBS to prepare phase angle versus frequency resonance spectra. The MPS solutions used for producing the insulation layer were: 1% MPS in ethanol with 0% water at pH=4.5 (FIG. 12A), 1% MPS in ethanol with 1% water at pH=9.0 (FIG. 12B), and 0.1% MPS in ethanol with 0.5% water at pH=9.0 (FIG. 12C). An optical micrograph of an example sensor is shown in the insert of FIG. 12A.

FIG. 12A shows that the baseline of the in-PBS spectrum of the PEPS was 20 degrees higher than that of the in-air spectrum, indicating that the insulation coating was still conductive. In comparison, the baseline of the in-PBS resonance spectra of FIGS. 12B and 12C were both fairly close to that of their respective in-air spectrum, indicating that MPS coatings were much less conductive.

Example 5

Figure 13:
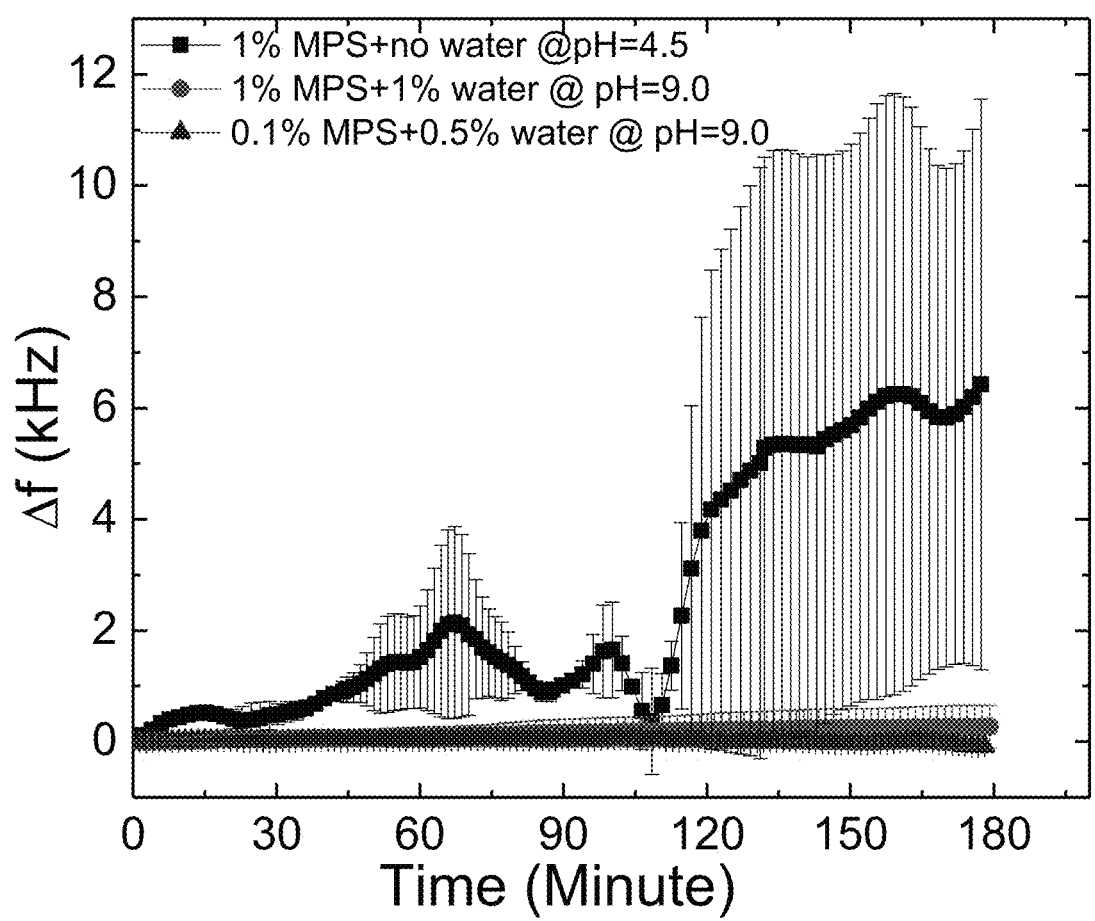
FIG. 13 shows resonance frequency shift versus time in PBS for piezoelectric plate sensors with an insulation layer fabricated with a different MPS ethanol solutions: 1% MPS with no water at pH=4.5 (squares), 1% MPS with 1% water at pH=9.0 (circles), and 0.1% MPS+0.5% water at pH=9.0 (triangles).

The stability of PEPSs with insulation layers fabricated using different MPS solutions was tested. The sensors were repeatedly immersed in PBS for 3 hr and the stability of the frequency of the width extension mode (WEM) resonance peak at around 3 MHz was measured. FIG. 13 shows the WEM resonance frequency shift, $\Delta f$, versus time for these sensors in PBS for up to 3 hr. The data shown in FIG. 13 represents the average of two independent runs. FIG. 13 shows that a coating made from an MPS solution without water at pH=4.5 not only had large frequency shifts within each run but also large differences between two runs, indicating that the insulation layer was unstable and unreliable in PBS. In contrast, both coatings obtained from MPS solutions with water at pH=9.0 showed negligible resonance frequency shifts over the course of 3 hr and negligible differences between two runs, indicating a much better stability and reliability of the MPS coating obtained at pH=9.0 and with water.

Example 6

The MPS-W9 insulation method of the present invention was compared with the prior art MPS-5 method described above. The MPS-5 method was carried out using a 1% MPS in ethanol solution without water for fabricating the insulation layer, and compared to an insulation layer fabricated by immersion in a 0.1% MPS solution in ethanol with 0.5% of water at pH=9 for 12 hr three times (the MPS-W9 method). A denser MPS coating was obtained from the MPS-W9 method and the MPS-W9 coating has a thickness >100 nm, which reduced the maximum current density of the sensor in a CV test to less than $10^{-7}$ A/cm$^2$. The reduced maximum current density results in a significant reduction in the noise level of the sensor as shown by the baseline difference between the spectrum of a sensor in a phosphate buffer saline (PBS) solution and that of the same senor in air.

Figures 14A, 14B:
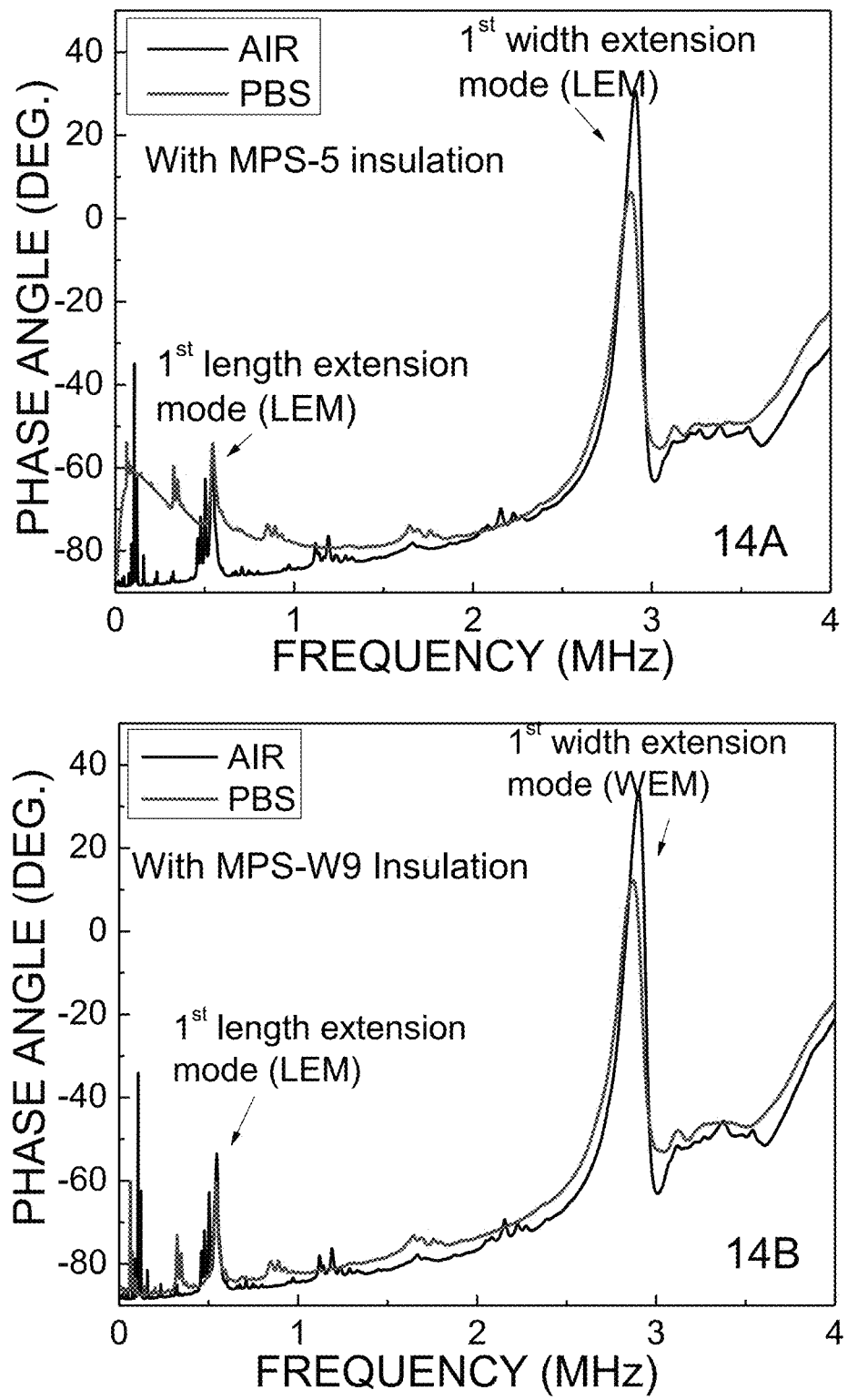
FIG. 14A shows phase angle versus frequency resonance spectra in-air and in PBS for piezoelectric plate sensors with an insulation layer fabricated with the MPS-5 method, as described in US 2011/0086368.
FIG. 14B shows phase angle versus frequency resonance spectra in-air and in PBS for piezoelectric plate sensors with an insulation layer fabricated with the MPS-W9 method of the present invention, described in detail below.

The in-air and in-PBS resonance spectra of two similar piezoelectric plate sensors—one electrically insulated using the MPS-5 method and the other electrically insulated using the MPS-W9 method, are shown in FIGS. 14A-14B, respectively. Both sensors exhibit a first length extension mode (LEM) peak around 500-600 kHz and a first WEM peak at around 3 MHz. There is little damping effect on the LEM and WEM peak frequencies of the sensor due to the much smaller vibration amplitude as compared to the bending modes. As a result, both sensors in FIGS. 14A-14B exhibited LEM and WEM peaks that showed minimal change in the peak height intensity and a negligible change in peak frequencies when in PBS as compared to in air. However, for the sensor coated using the MPS-5 method, the in-PBS baseline was about 13 degrees higher than the in-air baseline at the base of the first LEM resonance peak (FIG. 14A). In contrast, for the sensor coated using the MPS-W9 method, the in-PBS baseline was only 2 degrees higher than the in-air baseline at the base of the first LEM resonance peak (FIG. 14B). The higher in-PBS baseline of the MPS-5 PEPS insulation layer indicates a much higher noise level, which, in turn, reduces the sensitivity of the PEPS.

Example 7

Figures 15A, 15B:
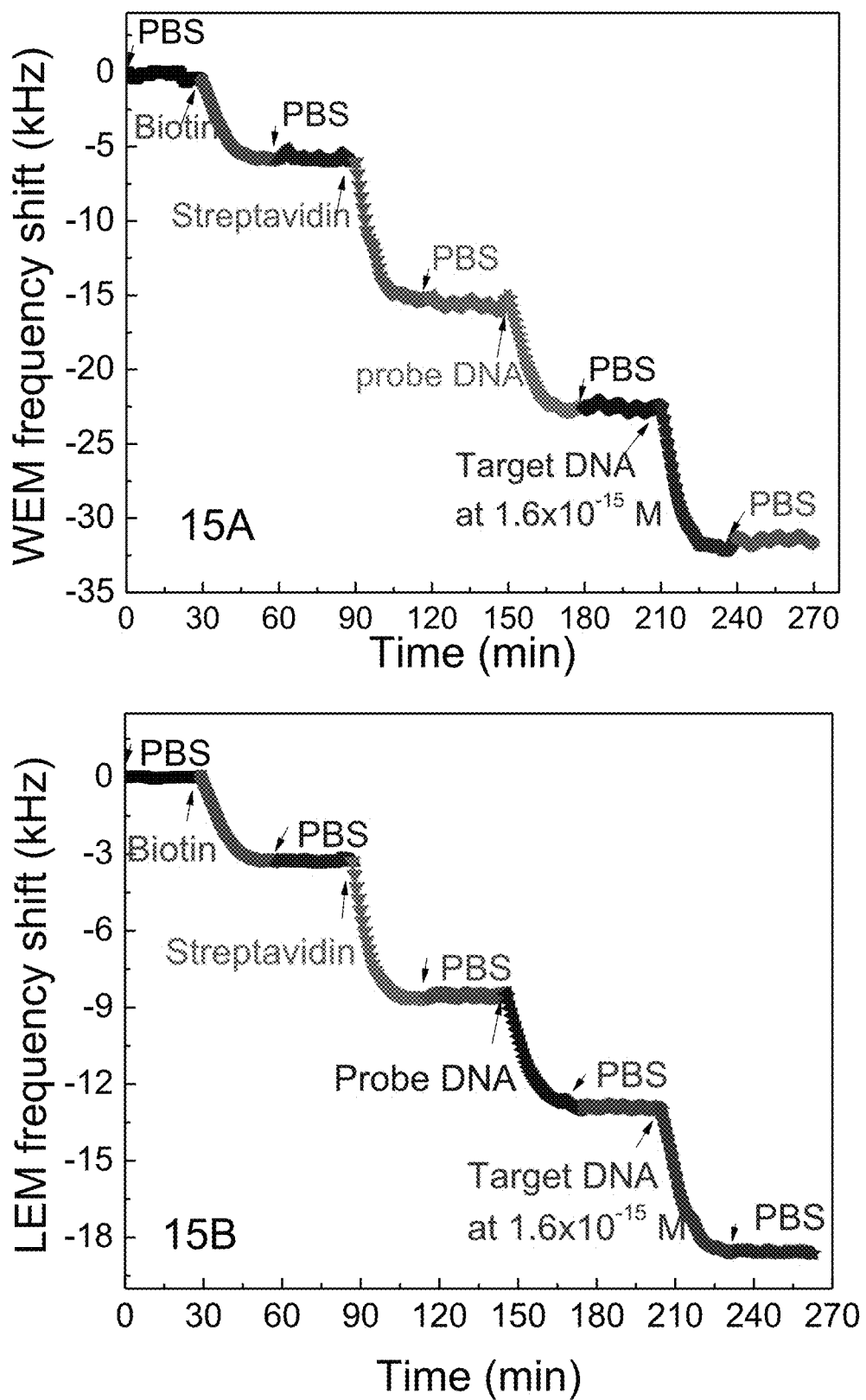
FIG. 15A shows resonance frequency shift versus time in width extension mode (WEM) for a PEPS with an insulation layer fabricated with that MPS-W9 method using various surface modification steps for detection of target DNA at a concentration of $1.6 \times 10^{-15}$ M.
FIG. 15B shows resonance frequency shift versus time in length extension mode (LEM) for a PEPS with an insulation layer fabricated with the MPS-W9 method at various surface modification steps for detection of target DNA at a concentration of $1.6 \times 10^{-15}$ M.

The LEM and WEM resonance peak frequencies in PBS were determined for a PEPS with an insulation layer fabricated using the MPS-W9 method. The results showed that both the LEM and WEM resonance peak frequencies of the sensor may be used for biological detection in liquid. In FIGS. 15A-15B, the $\Delta f$ versus time fir the MPS-W9-insulated sensor is shown during the various steps of steps of DNA probe binding to the insulation layer and final target DNA binding using the WEM (hollow symbols) and the LEM (solid symbols) peaks, respectively. The LEM resonance frequency shifts and the WEM resonance frequency shifts during the various steps of surface modification and target DNA binding at $1.6 \times 10^{-15}$ M are similar except that the magnitude of the WEM resonance frequency shifts was larger than the magnitude of the LEM resonance frequency shifts due to the higher WEM resonance frequency.

Figures 16A, 16B:
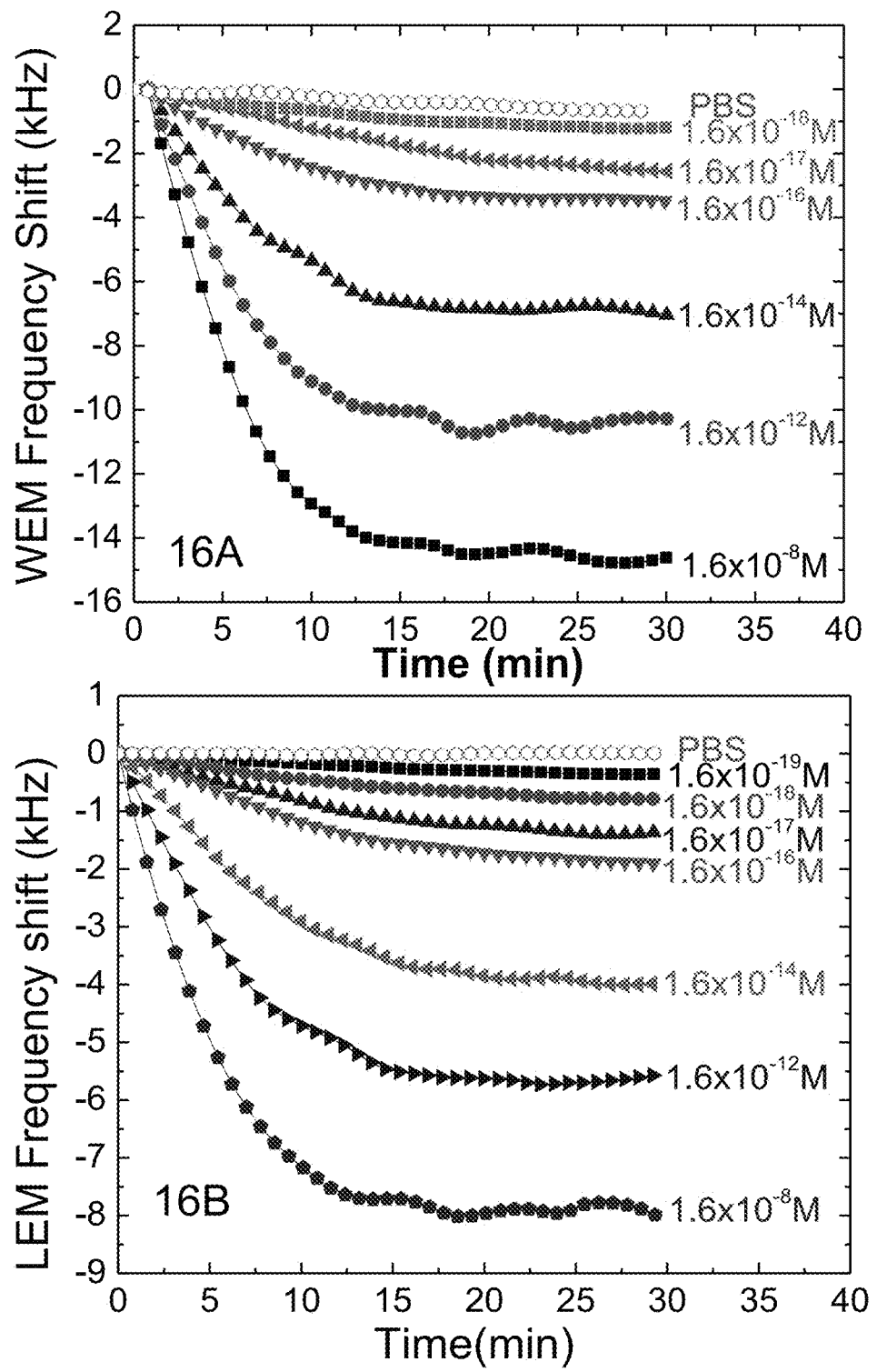
FIG. 16A shows resonance frequency shift versus time in width extension mode (WEM) for a PEPS with an insulation layer fabricated with the MPS-W9 method for detecting target DNA at various concentrations.
FIG. 16B shows resonance frequency shift versus time in length extension mode (LEM) for a piezoelectric plate sensor with an insulation layer fabricated with the MPS-W9 method for detecting target DNA at various concentrations.

FIGS. 16A-16B show the $\Delta f$ versus time for target DNA detection at various target DNA concentrations using the WEM and LEM resonance frequency peaks of the MPS-W9 insulated PEPS. Both the LEM and WEM peak positively and directly detected the target DNA at a concentration of $1.6 \times 10^{-19}$ M (10 copies/100 µl) in less than 30 min. This approaches the sensitivity of polymerase chain reaction (PCR) without the amplification steps required in PCR.

Figures 17A, 17B:
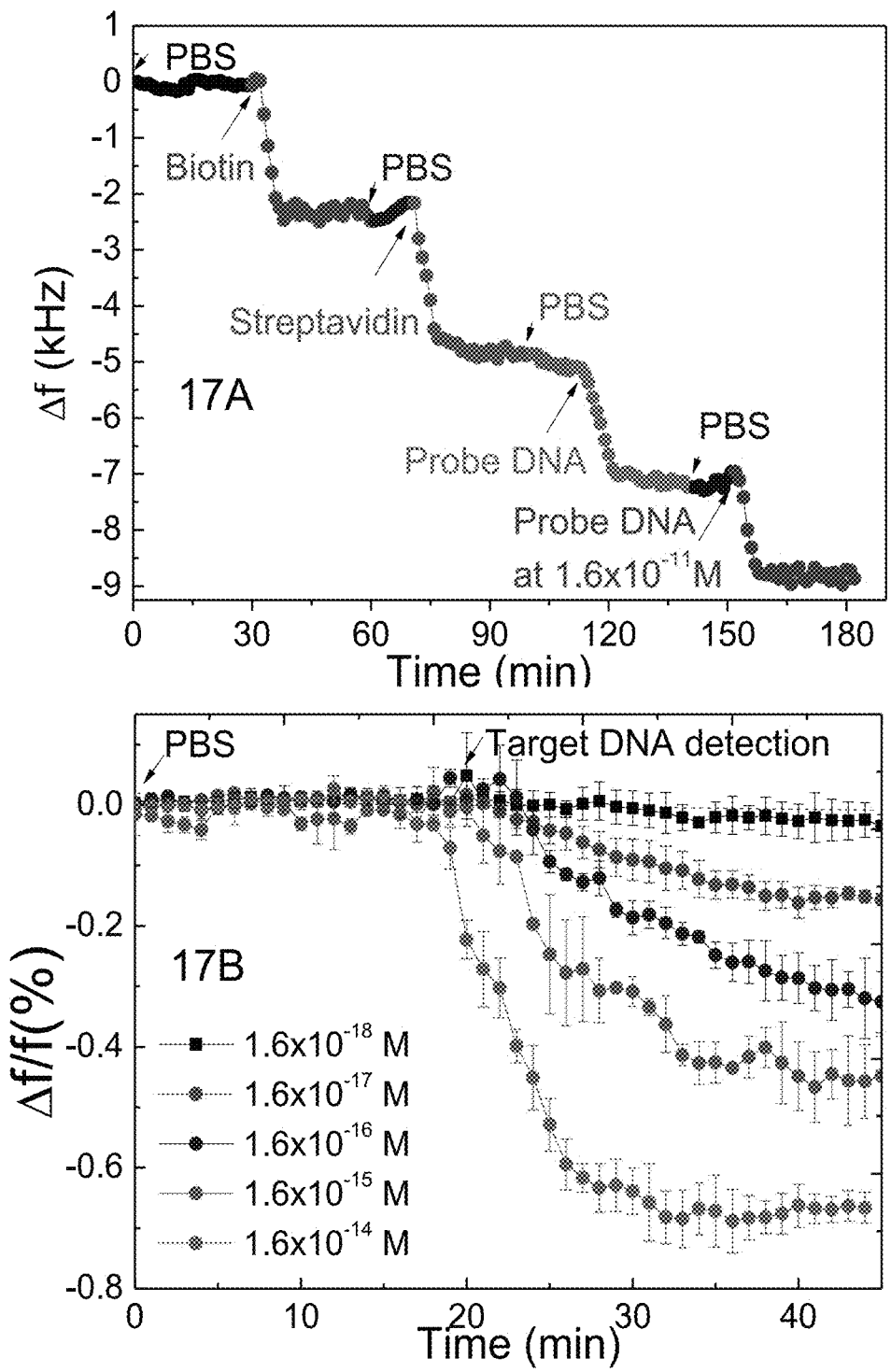
FIG. 17A shows resonance frequency shift versus time for a PEPS with an insulation layer fabricated with the MPS-5 method using various surface modification steps for detection of the target DNA at a concentration of $1.6 \times 10^{-15}$ M.
FIG. 17B shows relative resonance frequency shift versus time for a PEPS with an insulation layer fabricated with the MPS-5 method for detecting target DNA at various concentrations.

In comparison, <50% of PEPSs with an insulation layer produced by the MPS-5 method could be used for detection. For these PEPSs, only the LEM peak was reliable for detection and the sensitivity of the MPS-5 insulated PEPSs was significantly less than that of the MPS-W9 insulated PEPSs with similar attributes. The $\Delta f$ versus time of the MPS-5-insulated sensors during the various steps of DNA probe binding and final target DNA detection using the LEM peak (hollow symbols) is shown in FIG. 17A. In FIG. 17B, the $\Delta f$ versus time of target DNA detection at various target DNA concentrations using the LEM peaks of the MPS-5 insulated sensor is shown. The curves shown in FIG. 17B were the average of 3-4 independent runs. The MPS-5 insulated sensor exhibited a much higher noise level as compared to the PEPS insulated with MPS-W9 insulation (see FIG. 15B). Due to a higher noise level, the sensor insulated with MPS-5 insulation layer could only detect target DNA at $1.6 \times 10^{-17}$ M or above, and thus the MPS-5 insulated PEPS was two orders of magnitude less sensitive than the MPS-W9 insulated PEPS.

Example 8

Figure 18:
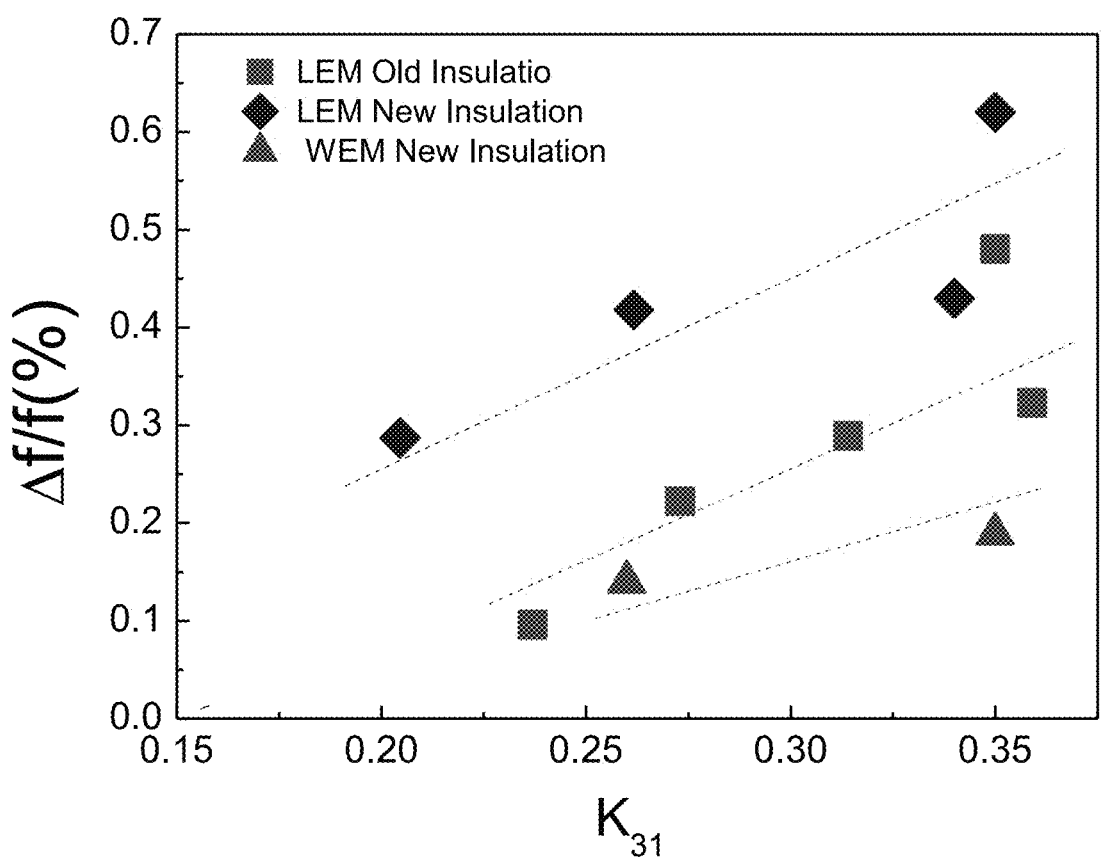
FIG. 18 shows relative resonance frequency shift Δf/f (%) versus $k_{31}$ for piezoelectric plate sensors with an insulation layer fabricated with the MPS-5 method and MPS-W9 method, using either length extension mode (LEM) or width extension mode (WEM).

Piezoelectric plate sensors with an insulation layer fabricated by either the MPS-W9 method or the MPS-5 method with different $k_{31}$ (the electromechanical coupling constant) values were tested in this Example. FIG. 18 shows the combined effect of the piezoelectric performance and the insulation performance by plotting $-\Delta f/f$ versus $k_{31}$ using the same biotin binding step. By improving both $k_{31}$ and insulation quality using the MPS-W9 insulation method, the $-\Delta f/f$ for the sensors having biotin bound thereto with the same $k_{31}$ values were increased 2-3 fold. It was observed that, although the WEM $\Delta f$ was higher than the LEM $\Delta f$ for the same detection (see FIGS. 15A-15B and FIGS. 16A-16B) due to the higher frequency of the WEM peak, the $\Delta f/f$ obtained from the WEM resonance frequency peaks was lower than those obtained from the LEM resonance frequency peaks of the same sensors.

Example 9

In this example, PEPSs insulated with the MPS-W9 method with $k_{31}=0.21$-$0.23$ and $k_{31}=0.32$ were used to detect HER2 antigen in solution. PEPSs were functionalized with a recombinant anti-HER2 antibody, L26, using the bi-functional linker, sulfosuccinimidyl-4-(N-maleimidomethyl) cyclohexane-1-carboxylate (Sulfo-SMCC). The sensor with antibody bound to the surface was further treated with a 30 mg/ml (3%) bovine serum albumin (BSA) solution for 2 hr followed by rinsing with 10 mg/ml (1%) BSA and Tween 20 for 10 min to block nonspecific binding. The functionalized PEPSs were used to detect HER2 in diluted human serum spiked with a various known concentration of HER2 antigen.

Figures 19A, 19B:
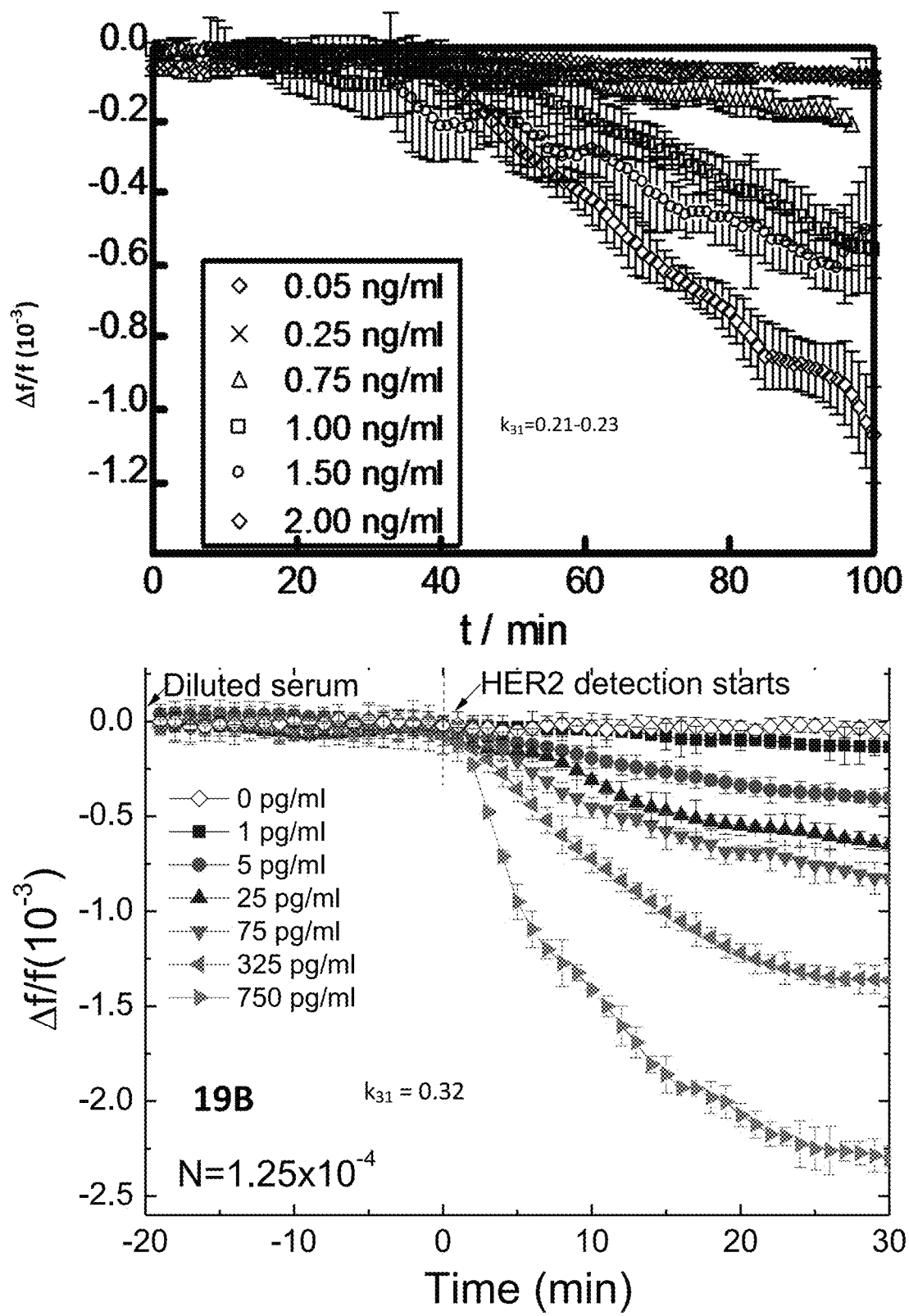
FIG. 19A shows $\Delta f/f(10^{-3})$ versus time for piezoelectric plate sensors with $k_{31}$=0.21-0.23 in detecting HER2 at various concentrations.
FIG. 19B shows $\Delta f/f(10^{-3})$ versus time for piezoelectric plate sensors with $k_{31}$=0.32 at various HER2 concentrations.

The relative resonance frequency shift, $\Delta f/f$ versus time at various HER2 concentrations is shown for sensors with $k_{31}=0.21$-$0.23$ in FIG. 19A and for sensors with $k_{31}=0.32$ in FIG. 19B. In the figures, f denotes the sensor initial resonance frequency and $\Delta f$ denotes the resonance frequency change. Note that each data point in FIG. 19A was the adjacent average of nine detections and the curve of each concentration was the average of three independent detections. The first 20 min, the sensors were only exposed to diluted serum. Only after $t=20$ min, HER2 containing diluted sera started to flow in the detection chamber. The data from sensors with $k_{31}=0.32$ were significantly less noisy than those from the sensors with $k_{31}=0.21$-$0.23$. The sensors with $k_{31}=0.32$ could clearly detect HER2 at far lower concentrations, namely, concentrations as low as 5 pg/ml, with a $\Delta f/f=0.4 \times 10^{-3}$ at $t=30$ min. The noise level, N, was defined as the standard deviation of $\Delta f/f$ in background serum with no HER2. The signal (S) to noise ratio (S/N) was >3 at this concentration. In comparison, sensors with $k_{31}=0.21$-$0.23$ could only detect HER2 at 0.75 ng/ml with an average $\Delta f/f=0.25 \times 10^{-3}$ with a comparable N at $t=80$-$100$ min.

Figure 20:
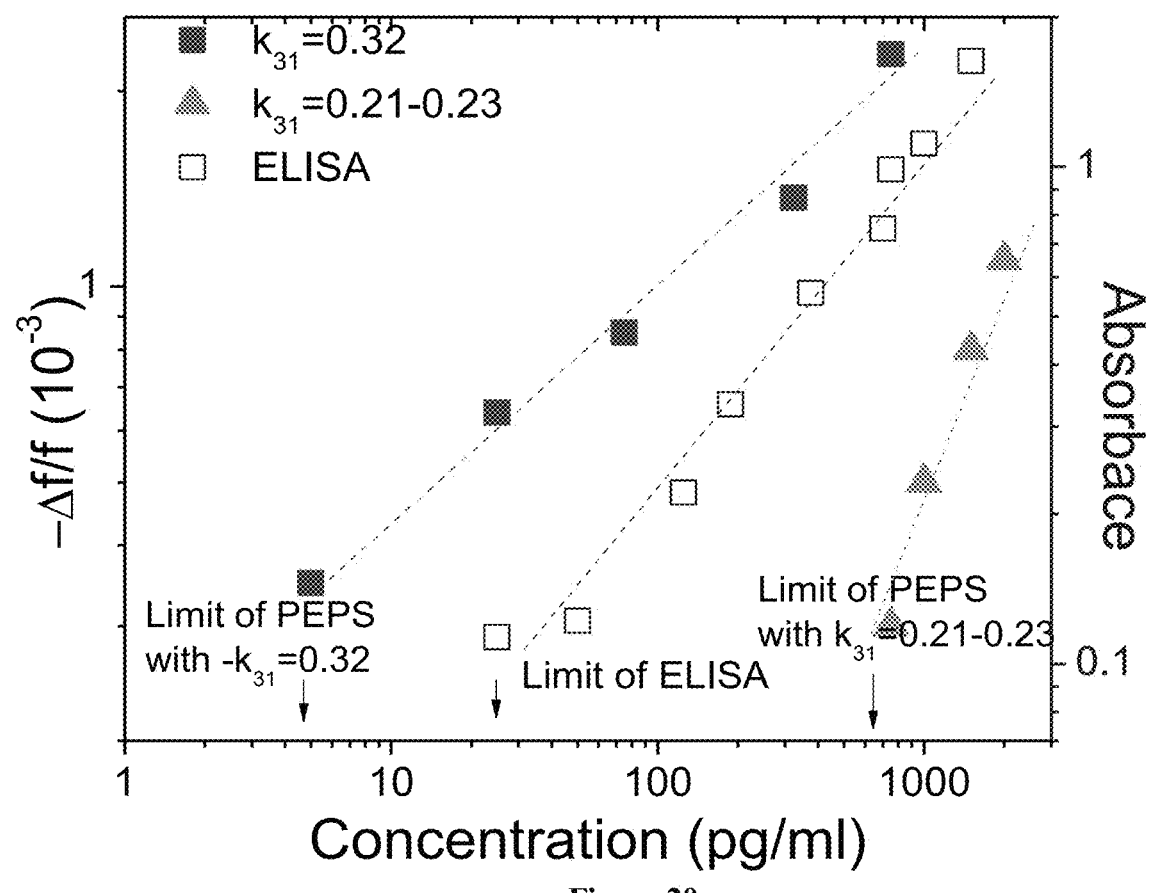
FIG. 20 shows $-\Delta f/f(10^{-3})$ versus HER2 concentration for piezoelectric plate sensors with $k_{31}$=0.32 (full circles)

Detection using a commercial ELISA kit (Cat #QIA10-1EA, Calbiochem) was carried out in HER2 PBS solution with the same antibody. The ELISA signal versus HER2 concentration in PBS measured by an Infinite 200 Pro (Tecan, San Jose, Calif.) is shown as hollow squares in FIG. 20. For comparison, the average $\Delta f/f$ over $t=80$-$100$ min for PEPSs with $k_{31}=0.21$-$0.23$ versus concentration is also shown in FIG. 20. Also shown in FIG. 20 is the average $\Delta f/f$ over $t=25$-$30$ min versus HER2 concentration for PEPSs with $k_{31}=0.32$. The concentration limit for the PEPS with $k_{31}=0.32$ was 5 pg/ml, 150 times better than the 750 pg/ml concentration limit of the sensors with $k_{31}=0.21$-$0.23$. Although $-\Delta f/f$ versus c (concentration) was not linear, these curves were quantitative and thus can be used as standard curves for quantification of HER2 concentration.

The sensitivity enhancement of the PEPS with $k_{31}=0.32$ over the PEPS $k_{31}=0.21$-$23$ may be understood as follows. As can be seen from FIG. 20, $-\Delta f/f$ was roughly $\propto c^{1/3}$ for sensors with $k_{32}=0.32$. Improving $k_{31}$ from 0.21-23 to 0.32 increased $-\Delta f/f$ by about 3.5 times, which would lower the concentration limit by 42 times according to the $-\Delta f/f \propto c^{1/3}$ rule. Furthermore, in addition to increasing the detection signal $-\Delta f/f$, the improved $k_{31}$ also reduced the noise level due to the provision of a much higher resonance peak. From FIGS. 19A and 19B, it can be observed that the noise level was reduced by about 3 times by improving $k_{31}$ to 0.32. As a result, S/N was increased by a factor of about 120 when $k_{31}$ was increased from 0.21-23 to 0.32. The additive value of these two effects is consistent with the 150 times sensitivity enhancement evidenced in FIG. 20.

The 5 pg/ml concentration detection limit obtained by the PEP with $k_{31}=0.32$ was 5 times lower than the 25 pg/ml concentration detection limit obtained using the commercial ELISA kit, when using the same antibody for detection.

Example 10

Detection of HER2 in the sera of breast cancer patients (patient #'s 4-10) and healthy controls (patient #'s 1-3) by HER2 ELISA and anti-HER2 a PEPS with $k_{31}=0.21$-$0.23$ are shown in FIG. 21. Negative control serum samples (patient #'s 1-3, underlined) and serum samples from patients with HER2 positive breast cancer (patient #'s 4-10) were assayed head-to-head by ELISA and anti-HER2 PEPS in triplicate. HER2 positive breast cancer patient serum samples were obtained under an Institutional Review Board (IRB) approved protocol from the Fox Chase Cancer Center Biosample Repository.

Anti-HER2 antibody functionalized sensors were equilibrated in the flow cell until a stable baseline was obtained for a period of at least 20 minutes. Patient serum was injected into the flow cell in order to obtain a final dilution of 1:40. The resonance frequency shift was recorded for 90 minutes. Data values were plotted as the average±the standard deviation. P values for the paired analysis are indicated in FIG. 21 with values greater than 0.05 indicating a lack of a significant difference between the PEPS and ELISA measurements. Measurements in which a significant difference was observed are indicated by an asterisk. The results shows that the PEPS with $k_{31}=0.21$-$23$ could correctly determine if a breast cancer patient's serum HER2 level was elevated.

Example 11

The sensitivity of the PEPS in detecting HER2 in serum was compared for a PEPS functionalized via biotin and a PEPS functionalized with SMCC. As shown in FIG. 22, $\Delta f/f$ versus time in full serum (hollow circles) of an antibody-functionalized and BSA blocked PEPS insulated the by MPS-W9 method indicated that the noise level in full serum was less than $5 \times 10^{-5}$ which was 2.5 times smaller than that of a PEPS insulated by the MPS-5 insulation method, as shown in FIGS. 19A and 19B.

Example 12

The $\Delta f/f$ versus time during the antibody binding step using biotin scheme (full squares) or SMCC scheme (full circles) were shown in FIG. 23 for comparison. Also shown in FIG. 23 are the $\Delta f/f$ versus time of sensors functionalized only with SMCC (open circles) and streptavidin (open squares) in PBS. It was observed, within 30 min of antibody binding, the $\Delta f/f$ of the sensors by the biotin scheme was 1.5 times that of the same sensor by the SMCC scheme, indicating that there were more 50% antibodies bound to the sensor surface using the biotin scheme (see the bar chart in the insert). Note the noise level of this sensors in PBS was less than $5 \times 10^{-5}$ due to the new insulation as consistent with the noise level shown in FIG. 22.

Detection of HER2 spiked in full bovine serum with PEPSS functionalized by either the biotin scheme or by the SMCC scheme was tested. The results are shown in FIG. 22 where the hollow squares represent the SMCC functionalized PEPS at 5 pg/ml of HER2 and the solid circles and solid squares represent a PEPS functionalized by the biotin scheme at 1 and 5 pg/ml HER2 in full serum. The $-\Delta f/f$ at t=30 min is plotted as a bar chart shown in the insert of FIG. 22. At 5 pg/ml, the $-\Delta f/f$ of the biotin-functionalized PEPS was about 1.6 times that of a similar PEPS functionalized by the SMCC scheme, consistent with the $-\Delta f/f$ of the antibody binding shown in FIG. 23. Due to this enhancement, the $-\Delta f/f$ of the biotin functionalized PEPS at 1 pg/ml of HER2 was almost the same as that of the same PEPS functionalized by SMCC at 5 pg/ml of HER2. The S/N was 5 and 11 for sensors functionalized by the biotin scheme at 1 and 5 pg/ml of HER2 in full serum, respectively, and 7 for sensors functionalized by the SMCC scheme at 5 pg/ml of HER2 in full serum. The increase of about 5-fold in the concentration sensitivity is consistent with the result for $-\Delta f/f \propto c^{1/3}$ shown in FIG. 20.

A summary plot of $-\Delta f/f$ versus various HER2 concentrations of tests using PEPSs made using various insulation methods, using various antibody binding schemes, and carried in various different sera, are shown in FIG. 24. Also shown in the insert of FIG. 24 is the corresponding S/N versus HER2 concentration. It was shown that both $-\Delta f/f$ and S/N are $\propto c^{1/3}$. Furthermore, improving the binding shifts the S/N versus concentration upwards and lowering noise shifted the S/N versus concentration to the left, both of which lower the detection concentration limit. The enhancement of $\Delta f/f$ by improving the density of the bound antibody on the PEPS surface and noise reduction by insulation improvement further reduced the detection concentration limit for sensor serum protein assays.

Example 13

Detection of 75 pg/ml of HER2 in bovine serum using a PEPS was conducted and the results are shown in FIG. 25. The HER2 containing sera had various dilution factors (full serum, ¼ diluted serum, and ½₀ diluted serum). The PEPS was blocked by 5% BSA and functionalized with an antibody for HER2. Also shown in FIG. 25 are the results of control examples 1 and 2, which respectively show the results of detection with an antibody-coated PEPS in full serum that contained no HER2 and detection at 75 pg/ml HER2 with a PEPS with no antibody in full serum (see the schematics in FIG. 25). Both control 1 and control 2 showed negligible changes in $\Delta f/f$ with a noise level of $<5 \times 10^{-5}$ indicating that the 5% BSA blocking was effective and there was no non-specific binding of the content of the serum to the PEPS as well as no nonspecific binding of HER2 to the PEPS surface with no antibody.

It was observed that the $\Delta f/f$ in various diluted sera converged toward a single value at about $1 \times 10^{-3}$ after a long time, which supported that the observed $\Delta f/f$ was indeed due to specific HER2 binding since, after a certain time, all bound antibody would bind to HER2. The increasingly slower change of $\Delta f/f$ with time with a decreasing degree of dilution suggests that after proper surface blocking the only effect of the serum was a crowding effect by other serum proteins such as albumin that hindered movement of the target antigens.

Example 14

In this example, secondary antibody-coated reporter microspheres were used to detect HER2 in serum. The binding of secondary antibody-coated reporter microspheres to the PEPS is depicted in FIG. 26A. After the target protein HER2 bound to the primary antibody bound to the sensor, it was immersed in a suspension of microspheres coated with a secondary antibody to the HER2. The secondary antibody including the microspheres then bonded to the HER2 protein on the sensor surface resulting in a resonance frequency decrease, providing in situ validation. Thus, detection of bound secondary antibody-coated microspheres following positive target protein HER2 binding can serve as a real-time validation of the detection. FIG. 26A shows the $\Delta f/f$ of HER2 detection in 1-in-40 diluted serum at concentrations of 0-75 pg/ml followed by detection of microspheres coated with the same secondary antibody used in the ELISA in 1-in-40 diluted serum. The positive microsphere detection confirmed the positive HER2 detection that preceded it.

The microspheres conjugated to the secondary antibody were photo-luminescent microspheres. Therefore, after binding of the secondary antibody and microspheres to the HER2, the microspheres were visible using a fluorescent microscope. Observation of fluorescence on the PEPS surface further confirms the presence of the target protein in the serum. The fluorescent images are shown in FIG. 26B. The number of fluorescent microspheres on the PEPS surface increased with an increasing HER2 concentration and there were no microspheres found on the surface of the PEPS that was exposed to 0 pg/ml HER2 serum, validating that the HER2 detection was indeed specific.

Example 15

The PEPSs of the present invention were used to detect cardiac troponin in serum. Human cardiac troponin I (T8665-18Q, US Biological—hereinafter "Troponin I") was spiked in full bovine serum at various concentrations. Troponin I detection in full bovine serum was carried out in a flow system with the PEPS situated at the center of the detection cell and using a flow rate of 1 ml/min. In each detection experiment, for the first 20 min (t=−20 to 0 min) the detection cell was connected to reservoir A which contained only bovine serum for the purpose of illustrating the stability of the PEPS with time in full serum and the specificity of the detection. At t=0 to 30 min, the detection cell was connected to reservoir B which contained the troponin sample for troponin detection. Switching between the bovine serum and the troponin sample was realized by simultaneously turning the two valves between the reservoirs and the detection cell.

The results of detection at various troponin I concentrations from 0.05 pg/ml to 100 pg/ml are shown in FIG. 27. There was no resonance frequency shift when the sensors were exposed to pure bovine serum, i.e., all curves at t=−20 to 0 min had negligible Δf/f with a standard deviation of Δf/f about 0.0037%, indicating that the blocking of the PEPS surface using 5% BSA was sufficient and that there was negligible non-specific binding on the PEPS by the serum. In all troponin I samples including the sample with 0.05 pg/ml troponin I, Δf/f increased with time. Furthermore, Δf/f was higher with a higher troponin concentration.

In contrast to the standard deviation of Δf/f of about 0.0037% in blank bovine serum, the values of the standard deviations Δf/f at t=30 min are 0.028%, 0.059%, 0.089%, 0.133%, and 0.18% at 0.05 pg/ml, 0.1 pg/ml, 1 pg/ml, 10 pg/ml, and 100 pg/ml of troponin I, respectively. Using the standard deviation in the blank serum as the noise level (0.0037%), the corresponding signal/noise (S/N) ratios were 8, 16, 24, 36, and 48 for 0.05 pg/ml, 0.1 pg/ml, 1 pg/ml, 10 pg/ml, and 100 pg/ml troponin I concentration at t=30 min, respectively.

FIG. 28 shows the Δf/f at 30 min (solid circles) and 20 min (hollow squares) versus troponin I concentration. Also shown os the S/N ratio as labeled on the right y-axis with the noise being the standard deviation of Δf/f in pure bovine serum, 0.0037%. The S/N ratio at 0.05 pg/ml was 6 and 8 at t=20 min and 30 min, respectively. The S/N at 0.05 pg/ml at both t=20 min and t=30 min were well over the commonly accepted detection limit of S/N=3, indicating that the detection of troponin I at 0.05 pg/ml was reliable even after 20 min and that likely the detection of limit (LOD) PEPS is actually below the lowest concentration tested, 0.05 pg/ml.

Example 16

An amine-activated DNA probe was covalently bound to piezoelectric plate sensors via sulfosuccinimidyl-4-(N-maleimidomethyl)cyclohexane-1-carboxylate (Sulfo-SMCC) (Pierce). Specifically, the sensors were dipped in 300 μl of 3 mg/ml sulfo-SMCC in phosphate buffer saline solution for 30 min. The maleimide of the SMCC reacted with the sulhydro of the MPS coating on the sensor surface to covalently bond the SMCC on the sensor surface. The senor was then dipped in a $10^{-8}$ M amine-activated DNA probe solution in PBS for 30 min. The NHS ester the SMCC reacted with the amine on the DNA probe to covalently bond the DNA probe on the sensor surface. There were about 3 amine-activated DNA probe molecules per 100 $nm^2$ of the sensor surface.

To prevent nonspecific binding on the sensor surface, after DNA probe binding, the sensor surface was further treated with a flow of 5% bovine serum albumin (BSA) at room temperature for 30 min. To further prevent stool from binding to the sensor surface, the BSA solution was also spiked in stool samples. FIG. 29 shows Δf/f versus time of the sensors after 5% BSA blocking in stool with no BSA blocking (diamonds), stool with 1% BSA blocking (squares), stool with 3% BSA blocking (circles), and stool with 5% BSA blocking. In stool with 0%, 1%, 3% and 5% BSA, at t=30 min, the sensors exhibited Δf/f of $-0.8 \times 10^{-3}$ $-0.3 \times 10^{-3}$, $-0.7 \times 10^{-4}$ and $-1.2 \times 10^{-6}$, respectively, indicating that a combination of 5% BSA sensor blocking and 5% BSA stool blocking was sufficient for the initial bacterial DNA detection studies.

Example 17

To optimize de-hybridization efficiency, stool samples spiked with 600 copies/ml of bacterial DNA and 5% BSA were heated at 97° C. for 10 min and cooled to room temperature (RT) in different schemes before entering the detection cell: (1) slow cool in a beaker (which took 20 minutes), (2) medium fast cool in 2-m long narrow air-cooled tubing (which took 2 min), and (3) fast cool in a 50-cm long water-cooled narrow tubing (which took about 30 seconds). The cooling in narrow tubing had two benefits: (1) at low concentrations, the newly de-hybridized DNA passed the narrow tubing in single file due to the narrowness of the tubing (~2 mm in diameter), thereby reducing the chance of re-hybridization, (2) the narrow tubing reduced the cooling time by allowing a much smaller amount of the sample to be cooled at a given time and also reduced the chance of re-hybridization before the stool entered the detection cell.

To further reduce the chance of re-hybridization, a 3 mm square glass plate coated with 25-nt long capture DNA (cDNA) was provided to the flow cell to capture the complementary strand of the bacterial DNA. The positive control was detection of 100-nt long ssDNA (Sigma). The $\Delta f_{bacterial\ DNA}/\Delta f_{ssDNA}$ is plotted in FIG. 30. $\Delta f_{bacterial\ DNA}/\Delta f_{ssDNA}$ increased from about 9.5% with slow cool, to 60% and 80% with medium fast cool and fast cool, respectively. With the complementary DNA capturing plate, $\Delta f_{bacterial\ DNA}/\Delta f_{ssDNA}$ were further increased to 11%, 80%, and 90% for slow cool, medium fast cool and fast cool, respectively. These results indicate that fast cooling coupled with complementary DNA capturing could achieve 90% efficiency in de-hybridizing the double stranded bacterial DNA for detection.

Example 18

PEPSs with a nucleic acid probe were used to detect bacterial DNA in stool samples. The stool samples were spiked with 0, 60, 180, 600, 1800, 6000, 60,000, and 600,000 copies/ml of bacterial DNA with 5% BSA. The stool samples were heated at 97° C. for 10 min to denature the double stranded bacterial DNA, and then were fast cooled without the capturing plate. The Δf/f versus time and −Δf/f at t=30 min are shown in FIGS. 31A and 31B, respectively. At t=30 min, the −Δf/f were $1 \times 10^{-6}$, $-1.4 \times 10^{-5}$, $-2.1 \times 10^{-5}$, $-3.2 \times 10^{-5}$, $-4.8 \times 10^{-5}$, $-7.1 \times 10^{-5}$, $-1.85 \times 10^{-4}$, $-7.1 \times 10^{-5}$, $-3.75 \times 10^{-4}$ at 0, 60, 180, 600, 1800, 6000, 60,000, and 600,000 copies/ml, respectively. Also shown is the detection result for negative controls (stool spiked with $6 \times 10^7$ copies/ml E. coli ATCC29522 DNA and $6 \times 10^5$ copies/ml of a human gene). There was no observable Δf/f for the negative controls even at these high concentrations. Using the standard deviation at 0 copies/ml ($1.2 \times 10^{-6}$) as the noise level (N) and the average Δf/f at t=30 min for each concentration as the signal (S), the S/N ratios=11, 24, 56, and 139 at 60, 600, 6000, and 60000 copies/ml, respectively.

Example 19

PEPSs were used to detect E. coli bacteria spiked in stool samples. The bacterial cells were lysed by either heating at 97° C. for 10 min, or adding sodium dodecyl sulfite (SDS) at 3% or 5% to the stool samples. It was found that adding SDS in the stool desorbed BSA from the sensor surface during the measurement. As a result, BSA must also be added with SDS to the stool samples. Simply heating the stool with 5% BSA was insufficient to lyse the bacteria and expose the DNA (FIG. 32A). The effect of various combinations of BSA and SDS on lysing bacterial cells spiking concentrations on the normalized $\Delta f_{bacteria}/\Delta f_{DNA}$ at 0 (control), 600, 6000, and 60,000 CFU/ml is summarized in FIG. 32A. With 5% BSA spiking, more SDS greatly improved the exposure of DNA and $\Delta f_{bacteria}/\Delta f_{DNA}$. However, with 5% SDS and 5% BSA blocking and 5% SDS and 5% BSA spiking in stool, the control tended to have an upshift of $\Delta f/f$ of about $5 \times 10^{-6}$ while with 5% BSA and 3% SDS blocking and 3% BSA and 3% SDS spiking in the stool there was no $\Delta f/f$ upshift.

Example 20

PEPSs were used to detect *E. coli* bacteria spiked in stool samples. The blocking of the sensor surface was carried out using stool samples with 5% BSA and 3% SDS. Separate stool samples were spiked with *E. coli* at various concentrations, which were lysed with 3% BSA and 3% SDS. The results are summarized in FIG. 32B. There was clear positive detection of bacteria down to 150 CFU/ml. $\Delta f/f$ obtained from bacteria spiked in stool closely followed that from purified DNA down to 150 CFU/ml. The S/N at 150 CFU/ml was still larger than 10, indicating that the PEPSs could detect the genetic signature of bacteria spiked in stool with great sensitivity without DNA isolation, concentration, and amplification.

Example 21

In this example, a reporter single-strand (ss) DNA coated fluorescent microsphere was used, in addition to the bound recognition molecule (DNA probe). The fluorescent microsphere was 6 µm in diameter (Polysciences™), coated with a reporter ssDNA with 25-30 bases long that is complementary to the target DNA in stool, as schematically shown FIG. 33. After allowing 30 minutes for binding of the target DNA on the PEPS, a suspension of $10^5$ microspheres/ml in PBS with appropriate blocking agents is flowed to the PEPS. FIG. 34 shows $\Delta f/f$ versus time for a 30 min detection of spiked bacteria at 600, 6,000, and 60,000 CFU/ml in stool with 3% BSA and 3% SDS at 50° C. for 30 min, followed by introducing fluorescent microspheres in PBS with 3% BSA and 3% SDS at room temperature. The microspheres significantly increased the $\Delta f/f$ values for all bacteria concentrations, while having only negligible effects on the control sample.

Example 22

This example shows that the PEPSs are capable of detecting *E coli* O157:H7 in stool by its genetic signature at 150 copies/ml in less than 40 min, with 10 min heating at >96° C. to lyse the bacterial cells and 30 min to detect the target DNA at 50° C. without the need of DNA isolation, concentration, and amplification. FIG. 35A shows $\Delta f/f$ versus time for detecting the genetic signature of *E. coli* spiked in stool and FIG. 35B plots the $-\Delta f/f$ at t=30 min versus *E. coli* concentration (circles). Also shown in FIG. 35B is the $-\Delta f/f$ at t=30 min in stool samples directly spiked with *E. coli* DNA (squares) for comparison. Clearly, the PEPSs could detect the genetic signature of *E. coli* in stool with 150 copies/ml sensitivity. Note such sensitivity was comparable or better than that of the polymerase chain reaction (PCR) except that the PEPS does not require DNA isolation, concentration and amplification required by PCR.

Example 23

Resonance frequency shift, $\Delta f$, of PEPSs was measured at various stages of sensor surface preparation that led to the final double-stranded HBV viral DNA detection in a simulated serum (FIG. 36). The steps included binding of sulfo-SMCC to the sensor surface followed by binding the DNA probe, followed by 5% BSA blocking, which was followed by testing in the negative control, blank simulated serum (or 5% BSA solution), and finally the detection of the double-stranded target viral DNA at $1 \times 10^{-18}$ M in the simulated serum. The sulfo-SMCC binding and DNA probe binding were done without flow whereas the BSA blocking and viral DNA detection were carried out with flow at a flow rate of 1.5 ml/min.

A substantial resonance frequency shift was observed in the sulfo-SMCC binding and DNA probe binding steps, indicating that sulfo-SMCC, and subsequently the DNA probe were indeed bound to the PEPS surface. In addition, the BSA blocking step also resulted in a significant resonance frequency shift indicating BSA adsorption on the PEPS surface. In the following negative control step (blank simulated serum), there was negligible further resonance frequency shift, indicating the previous BSA blocking step indeed saturated the sensor surface and that further exposure of the sensor surface to a high concentration of BSA such as 5% in the simulated serum did not result in addition BSA binding to the sensor surface.

Example 24

PEPSs functionalized with a nucleic acid probe were used to detect HBV viral DNA in simulated serum. The resonance frequency shift, $\Delta f$, of the PEPSs at various viral DNA concentrations over time is plotted in FIG. 37A. There was no discernible $\Delta f$ with the control, whereas there was a significant $\Delta f$ that increased with increasing viral DNA concentration. At the end of 30 min of detection, the $\Delta f$ was about 216 Hz, 500 Hz, and 840 Hz, for concentrations of 30, 60, and 600 copies/ml, respectively. Using the standard deviation of $\Delta f$ in the negative control as the noise level of the detection (27 Hz), the signal-to-noise ratio, S/N, was about 7, 18, and 32 for viral concentrations of 30, 60, and 600 copies/ml, respectively (FIG. 37B).

Example 25

Piezoelectric plate sensors with either 3 insulation layers (3×12 hours MPS coating) or 5 insulation layers (5×12 hours MPS coating) were used to detect HBV viral DNA in serum (FIG. 38). More details on the MPS coating method are given in Example 6. As a result of increasing the insulation layers on the sensor from 3 to 5, the noise level was substantially reduced from 27 Hz to 10 Hz. In addition, a large magnitude of $\Delta f$ was generated for the detection of the same viral DNA concentration. In other words, sensitivity of the sensors was enhanced by increasing the number of insulation layers from 3 to 5.

The increase in $\Delta f/f$ for detection at t=30 min of various viral DNA concentrations is shown in FIG. 39A. The $\Delta f/f$ was increased by about 20% at each of the three concentrations tested. For comparison, the S/N versus the viral DNA concentration is shown in FIG. 39B. Because the noise level was reduced from 27 Hz to 10 Hz and the Δf/f was increased with 5 insulation layers and the S/N for the 5-layer sensor was more than three times higher than those of comparable sensor with 3-layer insulation. This shows that the concentration limit for detection can be lower than the 30 copies/ml shown in example.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

Example 26

The $-k_{31}$ of a PMN-PT PEPS is function of whether the PMN-PT is fully sintered and the grain size of the PMN-PT layer as grain boundaries act to restrict crystalline orientation (which correlates with polarization orientation) switching within the grains. FIG. 40 shows scanning electron micrographs of 8-μm thick PMN-PT PEPS of different grain sizes. FIG. 41 shows the $-k_{31}$ value versus the grain size. Clearly, fully-sintered PMN-PT with large grains corresponds to a larger $-k_{31}$ value.

Example 27

FIGS. 42A-42C show the -Δf/f versus time of an 8-μm thick PMN-PT PEPS with $-k_{31}$=0.32 during the biotin-streptavidin (SA)-biotinylated probe DNA (pDNA) immobilization steps as described above. Also shown is the -Δf/f versus time of a 5-MHz QCM for the same immobilization steps. As can be seen, while the PEPS exhibited a -Δf/f of more than 1.2% at the end of the pDNA immobilization, the QCM's -Δf/f was too small to show on this scale. In fact, the -Δf/f of this PMN-PT PEPS was about 1300 times larger than can be accounted for by the mass change alone—the mechanism by which QCM generated its resonance frequency shift.

X-ray diffraction patterns of an 8-μm thick PMN-PT surrogate of about 1 cm×1 cm following each step of the immobilization scheme are shown in FIGS. 43A-43C. As can be seen, the height of the (002) peak decreased while the height of the (200) peak increased in each molecular binding step, clearly indicating that the crystalline orientation of the PMN-PT layer switched from the (002) to the (200) direction as a result of the molecular binding on the sensor surface. The crystalline orientation switching led to a Young's modulus change that provides the more than 1300 times enhancement in the -Δf/f of the PMN-PT PEPS over what could be accounted for by the mass change alone.

The dielectric constant, ε, of PMN-PT is known to depend on the crystalline orientation. In FIGS. 44A-44C, the relative dielectric constant change, Δε/ε versus time is shown for the PEPS during the same molecular binding steps. As can be seen, the PEPS clearly exhibits a positive Δε/ε indicating the crystalline orientation in the PEPS was indeed switching from the (002) orientation to the (200) orientation, consistent with the X-ray diffraction pattern change in the PMN-PT surrogate. Note that the QCM, on the other hand exhibited no appreciable Δε/ε.

Example 28

Hepatitis B (HB) is an infection of the liver caused by the HB virus (HBV). HBV basal core promoter double mutation (HBV DM) at nt 1762/1764, is a genetic marker associated with HCC risk. More than 60% of HCC patients carry HBV DM.

In this example, detection of HBV was conducted by using a continuous flow detecting system as depicted in FIG. 46. The PEPS in the detection cell is exposed to a sample at a temperature between the melting temperature of the mutant and that of the wild type. In addition, the flow rate was adjusted to a flow rate where the mutated gene HBV DM was detected by a PEPS coated with a 16-nt pDNA complementary to the 16-nt sequence of the mutant centered around the 1762/1764 mutations in urine at 60 copies/ml sensitivity in 30 min in a background of 200 times more wild type tDNA in a flow cell held at 30° C. and a flow rate of 4 ml/min. The study was carried out using single-stranded synthetic DNA probes.

The probes for mutant tDNA (MT tDNA, SEQ ID NO: 1) and the wild type tDNA (WT Tdna, SEQ ID NO: 2) were designed to contain different sequences so that fluorescent microspheres with different fluorescent colors could be used to report the presence of MT tDNA versus that of the WT tDNA. The MT tDNA had the sequence upstream of the mutated sites while the WT tDNA had the sequence downstream of the mutated sties as illustrated in FIG. 47, which shows the relationship between the MT tDNA, the WT tDNA, the probe DNA (pDNA, SEQ ID NO: 3), the MT reporter DNA (MT rDNA) that was complementary to the MT tDNA but different from the pDNA, and the WT rDNA that was complementary to the WT tDNA but different from MT tDNA. The MT tDNA and the WT tDNA were both 50-nt long and the MT rDNA (SEQ ID NO: 4) and WT rDNA (SEQ ID NO: 5) were both 30-nt long. By conjugating the MT rDNA on a blue fluorescent reporter microsphere (FRM) (see FIG. 47), binding of blue FRMs on the PEPS surface following tDNA detection would indicate the presence of bound MT tDNA on the PEPS surface thus validating the MT tDNA detection. Likewise, by conjugating the WT rDNA on an orange fluorescent reporter microsphere (FRM) (see FIG. 47), binding of orange FRMs on the PEPS surface following tDNA detection would indicate the presence of bound WT tDNA on the PEPS surface to permit the assessment of the specificity of the PEPS MT tDNA detection with respect to WT tDNA. The sequences of the various DNAs and the melting temperatures of the MT tDNA with pDNA, that of WT tDNA with pDNA, that of MT rDNA with MT tDNA, and that of WT rDNA with WT tDNA adjusted for salt concentration in PBS are listed in Table 1. Note the pDNA was amine-activated and had a 12-polethyleneglycol (PEG) spacer at the 5' end. The MT rDNA was amine-activated with a 12-PEG spacer at the 5' end and the WT rDNA was also amine-activated but with a 7-PEG spacer at the 3' end.

TABLE 1

The sequences and corresponding melting temperatures ($T_m$) for MT tDNA (with pDNA), WT tDNA (with pDNA), MT rDNA (with MT tDNA), and WT rDNA (with WT tDNA) adjusted for salt concentration in PBS. Note the mutated sites of the MT tDNA is underlined.

| Type of DNA | Sequence (5' to 3') | $T_m$ (° C.) |
|---|---|---|
| MT tDNA | 5'- . . . GGTTAA<u>TGA</u>TCTT TGT . . . -3' (SEQ ID NO: 1) | 47 |
| WT tDNA | 5'- . . . GGTTAAAGGTCTT TGT . . . -3' (SEQ ID NO: 2) | 23 |

TABLE 1-continued

The sequences and corresponding melting temperatures ($T_m$) for MT tDNA (with pDNA), WT tDNA (with pDNA), MT rDNA (with MT tDNA), and WT rDNA (with WT tDNA) adjusted for salt concentration in PBS. Note the mutated sites of the MT tDNA is underlined.

| Type of DNA | Sequence (5' to 3') | $T_m$ (° C.) |
|---|---|---|
| pDNA | Biotin-5'-ACAAAGATCATTA ACC-3' (SEQ ID NO: 3) | |
| MT rDNA | Amine-5'-ACAGACCAATTTAT GCCTACAGCCTCCTAG-3' (SEQ ID NO: 4) | 76.3 |
| WT rDNA | Amine-5'-AATCTCCTCCCCCA ACTCCTCCCAGTCTTT-3' (SEQ ID NO: 5) | 77.4 |

A detection temperature of 30° C. and a flow rate of 4 ml/min were found to provide the optimal detection sensitivity and specificity of the MT tDNA against WT tDNA. The schematics in FIGS. 48A-48B illustrate the MT tDNA detection in urine followed by detection of the blue MT FRMs at $1 \times 10^5$ FRMs/ml in PBS at 30° C. and at 4 ml/min while the detection $\Delta f/f$ versus time at various MT tDNA concentrations followed with the MT FRMs detection is shown in FIG. 48C.

The detection $\Delta f/f$ versus time at various WT tDNA concentrations followed by the orange WT FRMs detection at $1 \times 10^5$ FRMs/ml in PBS at 30° C. and at 4 ml/min is shown at FIG. 49. Clearly, at 30° C. and at a flow rate of 4 ml/min, the detection $-\Delta f/f$ of MT tDNA at 5 aM and t=30 min was $-\Delta f/f=0.2 \times 10^{-3}$, which was still much larger than that of WT tDNA at 100 fM and t=30 min which was $-\Delta f/f<0.1 \times 10^{-3}$, indicating the specificity of the MT tDNA detection at the chosen detection conditions.

In another experiment, PEPS was used for HBV DM detection in urine containing a mixture of MT tDNA with 200 times more WT tDNA at various MT tDNA concentrations followed with detection in an equal mixture of MT FRMs and WT FRMs of $10^5$ FRMs/ml concentrations in PBS. FIG. 50 shows the MN versus time of PEPS detection. In comparison with the detection of pure MT tDNA detection in urine in FIG. 48C, it can seen that the values of the $\Delta f/f$ in both figures were similar for the same MT tDNA concentrations, indicating that the presence of 200 times more WT tDNA did not significantly affect the detection of the MT tDNA.

Since two types of FRMs (MT FRMs and WT FRMs) are used for binding to mutant and wild type HBV viral DNA, respectively, different fluorescence of these FRMs may be observed using a fluorescent microscope. After detection in the mixture of MT FRMs and WT FRMs and washing, the PEPS was examined using a fluorescent microscope and fluorescent images were obtained from detection at various MT concentrations. The MT FRMs and WT FRMs emit fluorescence of different colors (MT FRMs emitting blue fluorescence and WT FRMs emitting orange fluorescence), thus the number of MT FRMs and WT FRMs bound on the surface of the sensor was easily determined. It was observed that the blue FRMs increased with an increasing MT concentration in the samples. The number of MT FRMs and that of WT FRMs versus $-\Delta f/f$ of tDNA detection at t=30 min is shown in FIG. 51. Clearly, the majority of the FRMs (about 75%) are blue MT FRMs and the number of the blue MT FMRs increased with an increasing detection $-\Delta f/f$ in the tDNA mixture, validating that the $\Delta f/f$ obtained in the tDNA mixture was mostly due to the binding of MT tDNA on the PEPS surface such that the bound FRMs were mostly MT FRMs.

Example 29

Kras point mutation is prevalent in many cancers including colorectal cancer and pancreatic cancer. A majority of Kras mutations involve a point mutation at codon 12. For a point mutation, the difference between the melting temperature of the mutant with a regular pDNA and that of the wild type with a regular pDNA is not wide enough for sufficient specificity. To widen the melting temperature difference for better mutation detection specificity, we used a 17-nucleotide DNA-locked nucleic acid (LNA) pDNA (Exiqon, Inc) to detect the Kras codon 12 mutation (Gene ID: 3845) centered around the point mutation (GGT→GTT). The pDNA had three LNA bases centered around the mutation site and the rest of the pDNA sequence consisted of DNA bases. FIG. 52 shows the relationship between the MT tDNA, the WT tDNA, pDNA, the MT rDNA, and the WT rDNA. Both targets of the MT tDNA and the WT tDNA were 50-nucleitides long. Both the MT rDNA probe and the WT rDNA probe were 30-nuelceotides long. The melting temperature for the MT tDNA binding to the pDNA was 70° C. and that for the WT tDNA binding to the pDNA of 54° C. The detection was carried out using a flow detection system of FIG. 46 at a flow rate of 4 ml/min and at 63° C. which was lower than the melting temperature of the Mt tDNA with the pDNA but higher than that for the WT tDNA with the pDNA.

The resultant $\Delta f/f$ of the MT tDNA detection in urine at various MT tDNA concentrations and the following MT FRMs detection at $1 \times 10^5$ FRMs/ml concentration at 63° C. and 4 ml/min is shown in FIG. 53. For comparison, the detection $\Delta f/f$ versus time at various WT tDNA concentrations followed with the WT FRMs detection at $1 \times 10^5$ FRMs/ml in PBS at 63° C. and at 4 ml/min is shown at FIG. 54. Clearly, at 63° C. and at a flow rate of 4 ml/min, the detection $-\Delta f/f$ of MT tDNA at 1 aM at t=30 min ($-\Delta f/f=0.6 \times 10^{-3}$) was still much larger than that of WT tDNA at 1 pM at t=30 min, ($-\Delta f/f<0.15 \times 10^{-3}$), indicating the specificity of the MT tDNA detection at the chosen detection conditions.

In another experiment, Kras MT tDNA was detected in a mixture with WT tDNA at a concentration 1000 times higher than that of MT tDNA. The MN was measured over time for PEPS detection in urine containing a mixture of MT tDNA with 1000 times more WT tDNA at various MT tDNA concentrations followed with detection in an equal mixture of MT FRMs and WT FRMs of $10^5$ FRMs/ml concentrations in PBS is shown in FIG. 55. Comparing the results in FIG. 55 with the detection of pure MT tDNA detection in urine in FIG. 53C, one can see that the values of the $\Delta f/f$ in both figures were similar for the same MT tDNA concentrations, indicating that the presence of 1000 times more WT tDNA did not significantly affect the detection of the MT tDNA.

Since two types of FRMs (MT FRMs and WT FRMs) are used for binding to mutant and wide type DNA respectively, different fluorescence of these FRMs may be observed using a fluorescent microscope. After the detection in the mixture of MT FRMs and WT FRMs and washing, the PEPS was examined using a fluorescent microscope and the obtained fluorescent images obtained from detection at various MT concentrations. The number of MT FRMs and that of WT FRMs versus $-\Delta f/f$ of tDNA detection at t=30 min is shown in FIG. 56. Clearly, the majority of the FRMs (about 75%) are blue MT FRMs and that the number of the blue MT FMRs increased with an increasing detection $-\Delta f/f$ in the tDNA mixture, validating that the MN obtained in the tDNA mixture was mostly due to the binding of MT tDNA on the PEPS surface such that the bound FRMs were mostly MT FRMs.

Example 30

PEPS detection of *Clostridium difficile* (CD) in 40 blinded patient stool samples was performed along with clinical qPCR as comparison. Using PEPS for detection of CD was carried out using the detection system shown in FIG. 46 by targeting the tcdB gene of CD. The patient stool samples were obtained from the archive of the Clinical Microbiology Laboratory of Hahnemann University Hospital. Amine-5'-CCAAAATGGAGTGTTACAAACAGGTG-3' (SEQ ID NO: 6) was used as the pDNA to target toxin B gene of CD, which has a melting temperature, $T_m=-68°$ C. for the binding of the pDNA to tcdB and a $T_m=50°$ C. for the binding of the pDNA to the human genome. There is no binding of the pDNA with the genomes of common gut-flora bacteria. The PEPS detection temperature was set to be at 58° C. to avoid potential non-specific binding of the pDNA to human genes.

The patient stool samples were first strained with a sieve with mm-size holes to remove large chunks. The PEPS detection was carried out with a stool volume of 10 ml and with 10% SDS and 3% BSA. The resonance frequency shift of the PEPS was measured using the width extension mode. In this example, a cutoff of $-\Delta f=20$ Hz was used as determining a CD positive sample. The comparison of the PEPS detection with results of the clinical qPCR from the microbiology lab of Hahnemann University Hospital is shown in FIG. 57. The PEPS correctly identified 17/19 (circles) CDI positive samples and 19/21 (squares) CDI negative samples. Using qPCR results as the gold standard, PEPS exhibited 90% (17/19) sensitivity and 90% specificity (19/21). This example indicates that PEPS exhibited similar sensitivity and specificity compared to qPCR except that PEPS did not require DNA isolation or DNA amplification. It was also observed that false positives and false negatives were repeatable and that the false positives were also toxin positive. Since both the sensitivity and specificity of qPCR are not 100%, this may suggest that PEPS has better sensitivity and specificity than qPCR Example 31

In this example, a PEPS was used to detect CD toxin A spiked in stool samples. An array of three PEPS was used. One PEPS was not functionalized with any antibody but was treated with 5% BSA for blocking nonspecific binding. The second and third PEPS were both functionalized with anti-toxin A antibody. An example of relative resonance frequency shift in detection of a stool sample spiked with 25 pg/ml toxin A is shown in FIG. 58A. The average $\Delta f/f$ at 25-30 min of detecting stool samples spiked with toxin A at different concentrations using an array of three PEPS is summarized in FIG. 58B. This example demonstrates that PEPS can detect toxin A spiked in stool with 10 pg/ml analytical sensitivity, more than 100 times more sensitivity than toxin enzyme immunoassay (EIA).

Example 32

In this example, PEPS was used to detect purified Tn antigen spiked in serum. Tn antigen is known to be an O-linked abnormal glycan on mucin 1 (MUC1). Therefore, the purified Tn molecules are glycoproteins that can bind specifically to both anti-Tn antibody and anti-MUC1 antibody. In FIG. 59, a 3-PEPS array was used to detect purified Tn spiked in serum. PEPS A of the array was not functionalized with an antibody, PEPS B was functionalized with anti-Tn antibody, and PEPS C was functionalized with anti-MUC1 antibody. The hollow symbols and the solid symbols in FIG. 59 represent the results obtained at 100 pg/ml and 1000 pg/ml of the spiked Tn glycoprotein in serum, respectively. Both PEPS B and PEPS C detected the same glycoprotein, indicating that Tn antigen is indeed on MUC1, though not all MUC1 contains Tn antigens. Only the MUC1 on the membrane of cancer cells contains Tn antigens. In FIG. 60, the $-\Delta f/f$ of a 3-PEPS array at 25-30 min is plotted against Tn concentration spiked in serum. This example indicated that PEPS can detect Tn antigen with an analytical sensitivity of 1 pg/ml.

Example 33

In this example, an array of three PEPS was used to detect Tn antigen, anti-Tn antibody, and legumain in 10 patient serum samples. One PEPS was functionalized with monoclonal anti-Tn antibody to detect Tn antigen. The second PEPS was functionalized with synthetic Tn antigen (Sigma) to detect anti-Tn antibody generated by the patient's immune system. The third PEPS was functionalized with an antibody to detect legumain, an asparaginyl endopeptidase (AEP) present in the tumor microenvironment and also on the membrane of cancer cells. Detection of legumain along with Tn antigen and anti-Tn antibody would make the molecular detection of cancer more sensitive and specific: Tn antigen would indicate the presence of cancerous epithelial cells, anti-Tn antibody would confirm the presence Tn antigen and hence the presence of the cancerous epithelial cancer cells, and legumain would indicate the presence of the tumor microenvironment. In FIG. 61, the average detection $-\Delta f/f$ at 25-30 minutes is shown for all 10 blinded patient sera with four-fold dilution using the 3-PEPS array. The solid symbols represent detection results from cancer patients and hollow symbols from non-cancer patients. It was observed that the PEPS could detect Tn antigen, anti-Tn antibody, and legumain at a few tens to a few hundreds pg/ml concentrations.

Example 34

In this example, a PEPS was used to detect the DNA of hepatitis B viruses spiked in a simulated serum. The simulated serum was prepared by first spiking 5% of bovine serum albumin (BSA) in PBS as the most abundant protein in the serum. Human DNA was also added to the simulated serum to mimic that real human sera containing human DNA. The probe DNA (pDNA) had 24 nt functionalized on the PEPS, which binds to the HBsAg coding region of HBV DNA (long curved line in FIG. 62). The HBV DNA also can bind to blue fluorescent microspheres (FRM in FIG. 62).

The $\Delta f$ was measured over time for detection of spiked viral DNA in simulated sera (FIG. 63A) and detection of the viral DNA of spiked HB viral particles in simulated serum (FIG. 63B). The concentration of SDS used was 5% for detecting viral DNA (denaturing DNA) and 10% for detecting viral particles (lysing and denaturing DNA). Comparison of $-\Delta f$ at 25-30 min of viral DNA detection and HB viral particles detection is shown in FIG. 64. Based on FIG. 64, with 10% SDS, the −Δf for detecting the viral particles was comparable with detecting spiked viral DNA.

Example 35

In this example, the FRMs shown in FIG. 62 were used to bind to the viral DNA. The amount of FRMs in PBS was 1×10$^5$ FRMs/ml. In FIG. 65, the Δf was measured over time for detecting viral particles at 300, 600, and 30,000 viruses/ml, respectively, followed by FRM binding. The Δf of FRMs detection increased in proportion to the Δf of the viral particle detection, indicating that there was an increasing amount of the viral DNA captured on the PEPS surface with increasing viral particle concentrations. In FIGS. 66A-66C, the fluorescent images of the PEPS are shown after the FRM binding following detection at 300 (FIG. 66A), 600 (FIG. 66B), and 3,000 (FIG. 66C) viral particles/ml. The light spots are fluorescence from bound FRMs on the PEPS surface. The number of FRMs on the PEPS indeed increased with an increasing viral particle concentration.

Example 36

In this example, an array of PEPS was used for simultaneous detection of all of the six possible mutation sites of the codon-12 Kras mutation. Table 2 shows the melting temperatures of the six LNA probe DNAs (pDNAs) each targeting one of the six possible mutation sites within codon 12. The melting temperatures of the LNA pDNAs with the wild type are also shown in Table 2. The melting temperature for the MT tDNA ranged from 68° C. to 72° C. and those of the WT tDNA ranged 50.1° C. to 54.3° C. with melting temperature differences ranging from 15.3° C. to 20.9° C. To facilitate simultaneous detection of all six possible mutation sites, an array of six PEPSs was used, each functionalized with one of the LNA pDNA. The detection of each of the target MT tDNAs using an array of 6 PEPSs each functionalized with one of the six pDNAs was carried out at 63° C., a temperature midway between all melting temperatures of the MT and those of the WT.

In each detection event, the urine was spiked with only one of the MT tDNAs. Therefore, only one of the PEPSs had the pDNA complementary to the MT tDNA that could detect the tNDA. The measured Δf versus time for the six detection events is plotted in FIG. 67. Each probe only detected one mutation site but not the others. This example clearly illustrates that the array of PEPS coupled with the flow system illustrated in FIG. 46 could detect multiple mutation sites at the same time from the same sample without the need for DNA isolation or amplification, an advantage over the current PCR- or LAMP-based technologies that do not have the capability of multiplexing.

TABLE 2

List of the melting temperature of each of the six LNA probe DNA with its corresponding MT tDNA and that with the WT tDNA for the codon-12 Kras mutation.

| Mutation | $T_m$ of MT (° C.) | $T_m$ of WT (° C.) | $\Delta T_m$ (° C.) |
| --- | --- | --- | --- |
| GGT → AGT | 68 | 52.7 | 15.3 |
| GGT → CGT | 71 | 50.1 | 20.9 |
| GGT → TGT | 69 | 53.3 | 15.7 |
| GGT → GAT | 70 | 54.7 | 15.3 |
| GGT → GCT | 72 | 51.1 | 20.9 |
| GGT → GTT | 70 | 54.3 | 15.7 |

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An insulated piezoelectric plate sensor comprising, a piezoelectric layer comprising a piezoelectric material with a $-d_{31}$ coefficient of from about 20 pm/V to about 5000 pm/V, at least two electrodes operatively associated with the piezoelectric layer, and an insulation layer, wherein the piezoelectric plate sensor has a transverse electromechanical coupling coefficient $-k_{31}$ of at least about 0.3 and a maximum current density of less than about $10^{-7}$ A/cm$^2$.

2. The insulated piezoelectric plate sensor of claim 1, wherein transverse electromechanical coupling coefficient $-k_{31}$ is at least about 0.31.

3. The insulated piezoelectric plate sensor of claim 1, wherein the maximum current density is measured by cyclic voltammetry.

4. The insulated piezoelectric plate sensor of claim 1, wherein the piezoelectric plate sensor has a mass detection sensitivity of $1\times10^{-13}$ g/Hz or less.

5. The insulated piezoelectric plate sensor of claim 1, wherein the insulation layer comprises mercaptopropyltrimethoxysilane.

6. The insulated piezoelectric plate sensor of claim 1, further comprising at least one recognition molecule bound to a surface of the insulation layer.

7. The insulated piezoelectric plate sensor of claim 6, wherein the at least one recognition molecule is bound to the surface of the insulation layer by a linker selected from the group consisting of sulfosuccinimidyl-4-(N-maleimidomethyl)cyclohexane-1-carboxylate and biotin.

8. The insulated piezoelectric plate sensor of claim 6, wherein the recognition molecule is selected from the group consisting of an antibody, an antigen, a receptor, a ligand and a nucleic acid probe.

9. The insulated piezoelectric plate sensor of claim 1, further comprising a blocking agent on said insulation layer to block non-specific binding to the insulation layer.

10. The insulated piezoelectric plate sensor of claim 1, wherein the piezoelectric material has a $-d_{31}$ coefficient of from about 500 pm/V to about 5000 pm/V.

11. The insulated piezoelectric plate sensor of claim 1, wherein the piezoelectric material has a $-d_{31}$ coefficient of from about 2000 pm/V to about 5000 pm/V.

12. The insulated piezoelectric plate sensor of claim 1, wherein the piezoelectric layer has a thickness of from about 0.5 μm to about 127 μm.

13. The insulated piezoelectric plate sensor of claim 1, wherein the piezoelectric layer has a thickness of from about 0.5 μm to about 100 μm.

14. The insulated piezoelectric plate sensor of claim 1, wherein the piezoelectric layer has a thickness of from about 0.5 μm to about 50 μm.

15. The insulated piezoelectric plate sensor of claim 1, wherein the piezoelectric layer has a thickness of from about 0.5 μm to about 10 μm.

16. The insulated piezoelectric plate sensor of claim 1, further comprising a non-piezoelectric layer having a thickness of from about 0.05 μm to about 100 μm bonded to the piezoelectric layer.

17. The insulated piezoelectric plate sensor of claim 16, wherein the non-piezoelectric layer comprises a non-piezoelectric material selected from the group consisting of ceramic, polymeric, plastic, metallic material or combinations thereof.

18. The insulated piezoelectric plate sensor of claim 6, wherein the recognition molecule is anti-Tn antigen antibody or an antibody against an antigen selected from the group consisting of HER2, EGFR, VEGF Tn.

19. The insulated piezoelectric plate sensor of claim 6, wherein the recognition molecule is a nucleic acid probe for detecting a genetic signature of a condition selected from the group consisting of acute myocardial infarction, diarrheal disease, a *Clostridium difficile* infection, Hepatitis B viral infection.

* * * * *